United States Patent
Du Bois

(10) Patent No.: US 6,576,653 B2
(45) Date of Patent: Jun. 10, 2003

(54) BICYCLIC PYRROLYL AMIDES AS GLYCOGEN PHOSPHORYLASE INHIBITORS

(75) Inventor: Daisy Joe Du Bois, Palo Alto, CA (US)

(73) Assignee: Pfizer Inc., New York, NY (US)

(*) Notice: Subject to any disclaimer, the term of this patent is extended or adjusted under 35 U.S.C. 154(b) by 0 days.

(21) Appl. No.: 10/117,370

(22) Filed: Apr. 5, 2002

(65) Prior Publication Data

US 2002/0183369 A1 Dec. 5, 2002

Related U.S. Application Data

(62) Division of application No. 09/670,759, filed on Sep. 27, 2000, now Pat. No. 6,399,601.
(60) Provisional application No. 60/157,148, filed on Sep. 30, 1999.

(51) Int. Cl.[7] .................. A61K 31/407; C07D 491/048
(52) U.S. Cl. .................... 514/414; 514/237.2; 514/318; 544/111; 546/198; 548/406; 548/453
(58) Field of Search ................. 548/406, 453; 544/111; 546/198; 514/237.2, 318, 414

(56) References Cited

U.S. PATENT DOCUMENTS 4,325,963 A  4/1982  Hitzel, et al.

FOREIGN PATENT DOCUMENTS

| EP | 0846464 | 6/1998 |
|---|---|---|
| ES | 2081747 | 3/1996 |

OTHER PUBLICATIONS

Martin, W.H. et al., "Discovery of a Human Liver Glycogen Phosphorylase Inhibitor that Lowers Blood Glucose In Vitro", Proc. Na Acad. Sci. USA, 95: 1776=1781, [Feb. 1988].

Hoover. D.J. et al., "Indole–20carboxamide Inhibitors of Human Liver Glycogen Phospholylase", Journal of Medicinal Chemistry, 16,2934–2938, 1988.

Primary Examiner—Joseph K. McKane
Assistant Examiner—Sonya Wright
(74) Attorney, Agent, or Firm—Peter C. Richardson; Gregg C. Benson; Carl J. Goddard

(57) ABSTRACT

This invention relates to compounds of Formula I

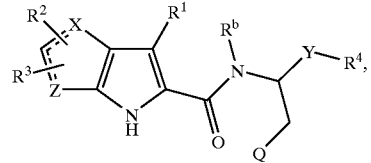

or stereoisomers, pharmaceutically acceptable salts or prodrugs thereof or a pharmaceutically acceptable salts of the prodrugs. This invention also relates to pharmaceutical compositions comprising a compound of Formula I, and to methods of treatment of diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, or tissue ischemia.

15 Claims, No Drawings

BICYCLIC PYRROLYL AMIDES AS GLYCOGEN PHOSPHORYLASE INHIBITORS

CROSS REFERENCE TO RELATED APPLICATION

This application is a divisional of U.S. application Ser. No. 09/670,759, filed Sep. 27, 2000, now allowed as U.S. Pat. No. 6,399,601. This application also claims priority of U.S. provisional application No. 60/157,148, filed Sep. 30, 1999.

FIELD OF THE INVENTION

This invention relates to bicyclic pyrrolyl amides and pharmaceutical compositions comprising bicyclic pyrrolyl amides. This invention also relates to the treatment of diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, and tissue ischemia, particularly myocardial ischemia, using the bicyclic pyrrolyl amides.

BACKGROUND OF THE INVENTION

In spite of the early discovery of insulin and its subsequent widespread use in the treatment of diabetes, and the later discovery of and use of sulfonylureas, biguanides and thiazolidenediones, such as troglitazone, rosiglitazone or pioglitazone, as oral hypoglycemic agents, the treatment of diabetes remains less than satisfactory.

The use of insulin requires multiple daily doses, usually by self injection. Determination of the proper dosage of insulin requires frequent estimations of the sugar in urine or blood. The administration of an excess dose of insulin causes hypoglycemia, with effects ranging from mild abnormalities in blood glucose to coma, or even death. Treatment of non-insulin dependent diabetes mellitus (Type II diabetes, NIDDM) usually consists of a combination of diet, exercise, oral hypoglycemic agents, e.g., thiazolidenediones, and in more severe cases, insulin. However, the clinically available hypoglycemic agents can have side effects that limit their use, or an agent may not be effective with a particular patient. In the case of insulin dependent diabetes mellitus (Type I), insulin is usually the primary course of therapy. Hypoglycemic agents that have fewer side effects or succeed where others fail are needed. leading to atherosclerosis and occlusive heart disease is well known. The earliest stage in this sequence is the formation of "fatty streaks" in the carotid, coronary and cerebral arteries and in the aorta. These lesions are yellow in color due to the presence of lipid deposits found principally within smooth-muscle cells and in macrophages of the intima layer of the arteries and aorta. Further, it is postulated that most of the cholesterol found within the fatty streaks, in turn, give rise to development of the "fibrous plaque," which consists of accumulated intimal smooth muscle cells laden with lipid and surrounded by extra-cellular lipid, collagen, elastin and proteoglycans. The cells plus matrix form a fibrous cap that covers a deeper deposit of cell debris and more extra cellular lipid. The lipid is primarily free and esterified cholesterol. The fibrous plaque forms slowly, and is likely in time to become calcified and necrotic, advancing to the "complicated lesion," which accounts for the arterial occlusion and tendency toward mural thrombosis and arterial muscle spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at particularly high risk. Such independent risk factors include glucose intolerance, left ventricular hypertrophy, hypertension, and being of the male sex. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

Hypertension (or high blood pressure) is a condition which occurs in the human population as a secondary symptom to various other disorders such as renal artery stenosis, pheochromocytoma or endocrine disorders. However, hypertension is also evidenced in many patients in whom the causative agent or disorder is unknown. While such "essential" hypertension is often associated with disorders such as obesity, diabetes and hypertriglyceridemia, the relationship between these disorders has not been elucidated. Additionally, many patients display the symptoms of high blood pressure in the complete absence of any other signs of disease or disorder.

It is known that hypertension can directly lead to heart failure, renal failure and stroke (brain hemorrhaging). These conditions are capable of causing death in a patient. Hypertension can also contribute to the development of atherosclerosis and coronary disease. These conditions gradually weaken a patient and can lead to death.

The exact cause of essential hypertension is unknown, though a number of factors are believed to contribute to the onset of the disease. Among such factors are stress, uncontrolled emotions, unregulated hormone release (the renin, angiotensin, aldosterone system), excessive salt and water due to kidney malfunction, wall thickening and hypertrophy of the vasculature resulting in constricted blood vessels and genetic factors.

The treatment of essential hypertension has been undertaken bearing the foregoing factors in mind. Thus, a broad range of beta-blockers, vasoconstrictors, angiotensin converting enzyme inhibitors and the like have been developed and marketed as antihypertensives. The treatment of hypertension utilizing these compounds has proven beneficial in the prevention of short-interval deaths such as heart failure, renal failure and brain hemorrhaging. However, the development of atherosclerosis or heart disease due to hypertension over a long period of time remains a problem. This implies that although high blood pressure is being reduced, the underlying cause of essential hypertension is not responding to this treatment.

Hypertension has been associated with elevated blood insulin levels, a condition known as hyperinsulinemia. Insulin, a peptide hormone whose primary actions are to promote glucose utilization, protein synthesis and the formation and storage of neutral lipids, also acts to promote vascular cell growth and increase renal sodium retention, among other things. These latter functions can be accomplished without affecting glucose levels and are known causes of hypertension. Peripheral vasculature growth, for example, can cause constriction of peripheral capillaries while sodium retention increases blood volume. Thus, the lowering of insulin levels in hyperinsulinemics can prevent abnormal vascular growth and renal sodium retention caused by high insulin levels and thereby alleviate hypertension.

Cardiac hypertrophy is a significant risk factor in the development of sudden death, myocardial infarction, and congestive heart failure. These cardiac events are due, at least in part, to increased susceptibility to myocardial injury after ischemia and reperfusion that can occur in out-patient as well as perioperative settings. There is an unmet medical need to prevent or minimize adverse myocardial perioperative outcomes, particularly perioperative myocardial infarction. Both non-cardiac and cardiac surgery are associated with substantial risks for myocardial infarction or death. Some 7 million patients undergoing non-cardiac surgery are considered to be at risk, with incidences of perioperative death and serious cardiac complications as high as 20–25% in some series. In addition, of the 400,000 patients undergoing coronary by-pass surgery annually, perioperative myocardial infarction is estimated to occur in 5% and death in 1–2%. There is currently no marketed drug therapy in this area which reduces damage to cardiac tissue from perioperative myocardial ischemia or enhances cardiac resistance to ischemic episodes. Such a therapy is anticipated to be life-saving and reduce hospitalizations, enhance quality of life and reduce overall health care costs of high risk patients. The mechanism(s) responsible for the myocardial injury observed after ischemia and reperfusion is not fully understood. It has been reported (M. F. Allard, et al., *Am. J. Physiol.*, 267: H66-H74 (1994)) that "pre ischemic glycogen reduction . . . is associated with improved post ischemic left ventricular functional recovery in hypertrophied rat hearts".

In addition to myocardial ischemia, other tissues can undergo ischemia and be damaged resulting in serious problems for the patient. Examples of such tissues include cardiac, brain, liver, kidney, lung, gut, skeletal muscle, spleen, pancreas, nerve, spinal cord, retina tissue, the vasculature, or intestinal tissue.

Hepatic glucose production is an important target for NIDDM therapy. The liver is the major regulator of plasma glucose levels in the post absorptive (fasted) state, and the rate of hepatic glucose production in NIDDM patients is significantly elevated relative to normal individuals. Likewise, in the postprandial (fed) state, where the liver has a proportionately smaller role in the total plasma glucose supply, hepatic glucose production is abnormally high in NIDDM patients.

Glycogenolysis is an important target for interruption of hepatic glucose production. The liver produces glucose by glycogenolysis (breakdown of the glucose polymer glycogen) and gluconeogenesis (synthesis of glucose from 2- and 3-Carbon precursors). Several lines of evidence indicate that glycogenolysis may make an important contribution to hepatic glucose output in NIDDM. First, in normal post absorptive man, up to 75% of hepatic glucose production is estimated to result from glycogenolysis. Second, patients having liver glycogen storage diseases, including Hers' disease (glycogen phosphorylase deficiency), display episodic hypoglycemia. These observations suggest that glycogenolysis may be a significant process for hepatic glucose production.

Glycogenolysis is catalyzed in liver, muscle, and brain by tissue-specific isoforms of the enzyme glycogen phosphorylase. This enzyme cleaves the glycogen macromolecule to release glucose-1-phosphate and a new shortened glycogen macromolecule. Several types of glycogen phosphorylase inhibitors have been reported to date: glucose and glucose analogs [Martin, J. L. et al., *Biochemistry*, 30:10101 (1991)]; caffeine and other purine analogs [Kasvinsky, P. J. et al., *J. Biol. Chem.*, 253: 3343–3351 and 9102–9106 (1978)]; substituted N-(indole-2–Carbonyl)-amides [PCT Publication Number WO 96/39385]; and substituted N-(indole-2-carbonyl)-glycinamides [PCT Publication Number WO 96/39384]. These compounds and glycogen phosphorylase inhibitors in general, have been postulated to be of use for the treatment of NIDDM by decreasing hepatic glucose production and lowering glycemia. [Blundell, T. B. et al., *Diabetologia*, 35: Suppl. 2, 569–576 (1992) and Martin et al., *Biochemistry*, 30: 10101 (1991)].

Myocardial ischemic injury can occur in outpatient as well as in perioperative settings and can lead to the development of sudden death, myocardial infarction or congestive heart failure. There is an unmet medical need to prevent or minimize myocardial ischemic injury, particularly perioperative myocardial infarction. Such a therapy is anticipated to be life-saving and reduce hospitalizations, enhance quality of life and reduce overall health care costs of high risk patients.

Although there are a variety of hyperglycemia, hypercholesterolemia, hypertension, hyperlipidemia, atherosclerosis and tissue ischemia therapies, there is a continuing need and a continuing search in this field of art for alternative therapies.

SUMMARY OF THE INVENTION

The present invention provides compounds of Formula I:

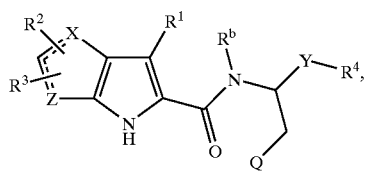

I stereoisomers, pharmaceutically acceptable salts and prodrugs thereof, and pharmaceutically acceptable salts of the prodrugs, wherein Q is aryl, substituted aryl, heteroaryl, or substitued heteroaryl;

each Z and X are independently (C, CH or $CH_2$), N, O or S;

$X^1$ is $NR^a$, $-CH_2-$, O or S;

each ———— is independently a bond or is absent, provided that both ———— are not simultaneously bonds;

$R^1$ is hydrogen, halogen, $-OC_1-C_8$alkyl, $-SC_1-C_8$alkyl, $-C_1-C_8$alkyl, $-CF_3$, $-NH_2$, $-NHC_1-C_8$alkyl, $-N(C_1-C_8\text{alkyl})_2$, $-NO_2$, $-CN$, $-CO_2H$, $-CO_2C_1-C_8$alkyl, $-C_2-C_8$alkenyl, or $-C_2-C_8$alkynyl;

each $R^a$ and $R^b$ is independently hydrogen or $-C_1-C_8$alkyl;

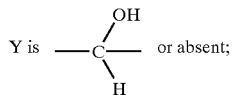

Y is ——C—— or absent;

$R^2$ and $R^3$ are independently hydrogen, halogen, $-C_1-C_8$alkyl, $-CN$, $-C\equiv C-Si(CH_3)_3$, $-OC_1-C_8$alkyl, $-SC_1-C_8$alkyl, $-CF_3$, $-NH_2$, $-NHC_1-C_8$alkyl, $-N(C_1-C_8\text{alkyl})_2$, $-NO_2$, —$CO_2H$, —$CO_2C_1$–$C_8$alkyl, —$C_2$–$C_8$alkenyl, or —$C_2$–$C_8$alkynyl, or $R^2$ and $R^3$ together with the atoms on the ring to which they are attached form a five or six membered ring containing from 0 to 3 heteroatoms and from 0 to 2 double bonds;

$R^4$ is —C(=O)—A;

A is —$NR^dR^d$, —$NR^aCH_2CH_2OR^a$,

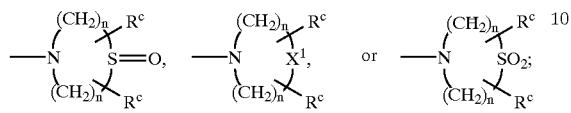

each $R^d$ is independently hydrogen, $C_1$–$C_8$alkyl, $C_1$–$C_8$alkoxy, aryl, substituted aryl, heteroaryl, or substituted heteroaryl;

each $R^c$ is independently hydrogen, —C(=O)$OR^a$, —$OR^a$, —$SR^a$, or —$NR^aR^a$; and each n is independently 1–3.

In a preferred embodiment of the compounds of Formula I, $R^b$ and $R^1$ are hydrogen.

In another preferred embodiment of the compounds of Formula I, $R^b$ is hydrogen;

$R^1$ is hydrogen;

Y is 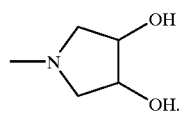 ; and A is 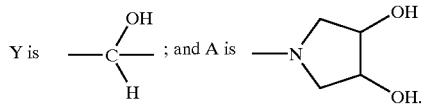

In another preferred embodiment of the compounds of Formula I, $R^b$ is hydrogen;

$R^1$ is hydrogen;

Y is absent; and

A is

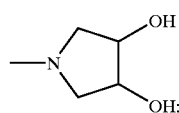

In another preferred embodiment of the compounds of Formula I, $R^b$ is hydrogen;

$R^1$ is hydrogen;

Z is C;

X is O or S;

Y is absent;

A is

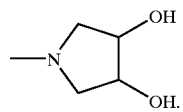

$R^2$ is hydrogen; and $R^3$ is hydrogen, halogen or methyl.

In another preferred embodiment of the compounds of Formula I,

Q is phenyl and A is

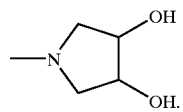

In another preferred embodiment, the invention provides compounds of Formula I

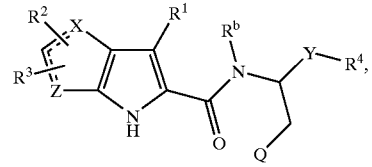

stereoisomers, pharmaceutically acceptable salts and prodrugs thereof, and pharmaceutically acceptable salts of the prodrugs, wherein Q is phenyl;

(Z is S and X is C), (Z is C and X is S), or (Z is C and X is O);

each ——— is independently a bond or is absent, provided that both ——— are not simultaneously bonds;

$R^1$ is hydrogen or halogen, each $R^a$ and $R^b$ is independently hydrogen or $C_1$–$C_8$alkyl;

Y is 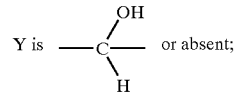 or absent;

$R^2$ and $R^3$ are independently hydrogen, halogen, $C_1$–$C_8$alkyl, —CN, —C≡CSi($CH_3$)$_3$, or $C_2$–$C_8$alkynyl, or $R^2$ and $R^3$ together with the atoms on the ring to which they are attached form a five or six membered ring containing from 0 to 3 heteroatoms and from 0 to 2 double bonds;

$R^4$ is —C(=O)—A;

A is —$NR^dR^d$,

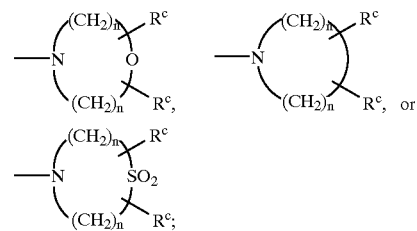

each $R^d$ is independently $C_1$–$C_8$alkyl;

each $R^c$ is independently hydrogen, —OH, or —C(=O)) $C_1$–$C_8$alkyl;

each n is independently 1–3.

In another preferred embodiment of the compounds of Formula I,

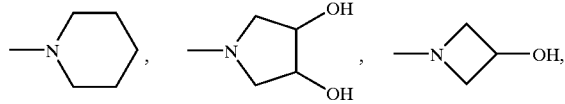

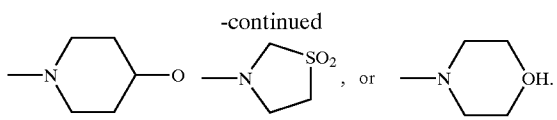

Also provided are pharmaceutical compositions comprising a compound of Formula I, stereoisomers, pharmaceutically acceptable salts and prodrugs thereof, and pharmaceutically acceptable salts of the prodrugs.

Also provided are methods of treating or preventing atherosclerosis, the methods comprising the step of administering to a patient having atherosclerosis or at risk of having atherosclerosis a therapeutically effective amount of a compound of Formula I, stereoisomers, pharmaceutically acceptable salts and prodrugs thereof, and pharmaceutically acceptable salts of the prodrugs.

Also provided are methods of treating diabetes, the methods comprising the step of administering to a patient having diabetes a therapeutically effective amount of a compound of Formula I, stereoisomers, pharmaceutically acceptable salts and prodrugs thereof, and pharmaceutically acceptable salts of the prodrug.

In a preferred embodiment of the methods of treating diabetes, the diabetes is non-insulin dependent diabetes mellitus (Type II).

In another preferred embodiment of the methods of treating diabetes, the diabetes is insulin dependent diabetes mellitus (Type I).

Also provided are methods of treating insulin resistance, the methods comprising the step of administering to a patient having insulin resistance a therapeutically effective amount of a compound of Formula I, stereoisomers, pharmaceutically acceptable salts and prodrugs thereof, and pharmaceutically acceptable salts of the prodrugs.

Also provided are methods of treating diabetic neuropathy, the methods comprising the step of administering to a patient having diabetic neuropathy a therapeutically effective amount of a compound of Formula I, stereoisomers, pharmaceutically acceptable salts and prodrugs thereof, and pharmaceutically acceptable salts of the prodrugs.

Also provided are methods of treating diabetic nephropathy, the methods comprising the step of administering to a patient having diabetic nephropathy a therapeutically effective amount of a compound of Formula I, stereoisomers, pharmaceutically acceptable salts and prodrugs thereof, and pharmaceutically acceptable salts of the prodrugs.

Also provided are methods of treating diabetic retinopathy, the methods comprising the step of administering to a patient having diabetic retinopathy a therapeutically effective amount of a compound of Formula I, stereoisomers, pharmaceutically acceptable salts and prodrugs thereof, and pharmaceutically acceptable salts of the prodrugs.

Also provided are methods of treating cataracts, the methods comprising the step of administering to a patient having cataracts a therapeutically effective amount of a compound of Formula I, stereoisomers, pharmaceutically acceptable salts and prodrugs thereof, and pharmaceutically acceptable salts of the prodrugs.

Also provided are methods of treating or preventing hypercholesterolemia, the methods comprising the step of administering to a patient having hypercholesterolemia or at risk of having hypercholesterolemia a therapeutically effective amount of a compound of Formula I, stereoisomers, pharmaceutically acceptable salts and prodrugs thereof, and pharmaceutically acceptable salts of the prodrugs.

Also provided are methods of treating or preventing hypertriglyceridemia, the methods comprising the step of administering to a patient having hypertriglyceridemia or at risk of having hypertriglyceridemia a therapeutically effective amount of a compound of Formula I, stereoisomers, pharmaceutically acceptable salts and prodrugs thereof, and pharmaceutically acceptable salts of the prodrugs.

Also provided are methods of treating or preventing hyperlipidemia, the methods comprising the step of administering to a patient having hyperlipidemia or at risk of having hyperlipidemia a therapeutically effective amount of a compound of Formula I, stereoisomers, pharmaceutically acceptable salts and prodrugs thereof, and pharmaceutically acceptable salts of the prodrugs.

Also provided are methods of treating hyperglycemia, the methods comprising the step of administering to a patient having hyperglycemia or at risk of having hyperglycemia therapeutically effective amount of a compound of Formula I, stereoisomers, pharmaceutically acceptable salts and prodrugs thereof, and pharmaceutically acceptable salts of the prodrugs.

Also provided are methods of treating hypertension, the methods comprising the step of administering to a patient having hypertension or at risk of having hypertension a therapeutically effective amount of a compound of Formula I, stereoisomers, pharmaceutically acceptable salts and prodrugs thereof, and pharmaceutically acceptable salts of the prodrugs.

Also provided are methods of treating or preventing tissue ischemia, the methods comprising the step of administering to a patient having tissue ischemia or at risk of having tissue ischemia a therapeutically effective amount of a compound of Formula I, stereoisomers, pharmaceutically acceptable salts and prodrugs thereof, and pharmaceutically acceptable salts of the prodrugs.

Also provided are methods of treating or preventing myocardial ischemia, the methods comprising the step of administering to a patient having myocardial ischemia or at risk of having myocardial ischemia a therapeutically effective amount of a compound of Formula I, stereoisomers, pharmaceutically acceptable salts and prodrugs thereof, and pharmaceutically acceptable salts of the prodrugs.

Also provided are methods of inhibiting glycogen phosphorylase, the methods comprising the step of administering to a patient in need of glycogen phosphorylase inhibition, a glycogen phosphorylase inhibiting amount of a compound of Formula I, stereoisomers, pharmaceutically acceptable salts and prodrugs thereof, and pharmaceutically acceptable salts of the prodrugs.

The present invention provides the compounds:

6H-thieno[2,3-b]pyrrole-5-carboxylic acid [(1S)-benzyl-3-((3R,4S)-dihydroxy-pyrrolidin-1-yl)-(2R)-hydroxy-3-oxo-propyl]-amide;

2-bromo-6H-thieno[2,3-b]pyrrole-5-carboxylic acid [(1S)-benzyl-3-((3R,4S)-dihydroxy-pyrrolidin-1-yl)-(2R)-hydroxy-3-oxo-propyl]-amide;

2-methyl-6H-thieno[2,3-b]pyrrole-5-carboxylic acid [(1S)-benzyl-3-((3R,4S)-dihydroxy-pyrrolidin-1-yl)-(2R)-hydroxy-3-oxo-propyl]-amide;

(±)-2-methyl-6H-thieno[2,3-b]pyrrole-5-carboxylic acid [1-benzyl-2-((3R,4S)-dihydroxy-pyrrolidin-1-yl)-2-oxo-ethyl]-amide;

2-bromo-6H-thieno[2,3-b]pyrrole-5-carboxylic acid [(1S)-benzyl-2-((3R,4S)-dihydroxy-pyrrolidin-1-yl)-2-oxo-ethyl]-amide;

2-Chloro-6H-thieno[2,3-b]pyrrole-5-carboxylic acid [(1S)-benzyl-3-((3R,4S)-dihydroxy-pyrrolidin-1-yl)-(2R)-hydroxy-3-oxo-propyl]-amide;

2-Chloro-6H-thieno[2,3-b]pyrrole-5-carboxylic acid [(1S)-benzyl-2-((3R,4S)-dihydroxy-pyrrolidin-1-yl)-2-oxo-ethyl]-amide;

2,4-dichloro-6H-thieno[2,3-b]pyrrole-5-carboxylic acid [(1S)-benzyl-3-((3R,4S)-dihydroxy-pyrrolidin-1-yl)-(2R)-hydroxy-3-oxo-propyl]-amide;

(±)-4H-thieno[3,2-b]pyrrole-5-carboxylic acid [1-benzyl-2-((3R,4S)-dihydroxy-pyrrolidin-1-yl)-2-oxo-ethyl]-amide;

2-bromo-4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

(±)-2-bromo-4H-furo[3,2-b]pyrrole-5-carboxylic acid [1-benzyl-2-((3R,4S)-dihydroxy-pyrrolidin-1-yl)-2-oxo-ethyl]-amide;

2-bromo-4H-furo[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

6H-thieno[2,3-b]pyrrole-5-carboxylic acid [(1S)-benzyl-2-((3R,4S)-dihydroxy-pyrrolidin-1-yl)-2-oxo-ethyl]-amide;

2-bromo-4H-thieno[3,2-b]pyrrole-5-carboxylic acid [(1S)-benzyl-2-((3R,4S)-dihydroxy-pyrrolidin-1-yl)-2-oxo-ethyl]-amide;

2-methyl-4H-thieno[3,2-b]pyrrole-5-carboxylic acid [(1S)-benzyl-2-((3R,4S)-dihydroxy-pyrrolidin-1-yl)-2-oxo-ethyl]-amide;

2,4-dichloro-6H-thieno[2,3-b]pyrrole-5-carboxylic acid [(1S)-benzyl-2-((3R,4S)-dihydroxy-pyrrolidin-1-yl)-2-oxo-ethyl]-amide;

2-Cyano-6H-thieno[2,3-b]pyrrole-5-carboxylic acid [(1S)-benzyl-2-(3-hydroxy-azetidin-1-yl)-2-oxo-ethyl]-amide;

2–Chloro-6H-thieno[2,3-b]pyrrole-5-carboxylic acid [(1S)-benzyl-2-morpholin-4-yl-2-oxo-ethyl]-amide;

2–Chloro-6H-thieno[2,3-b]pyrrole-5-carboxylic acid [(1S)-dimethylcarbamoyl-2-phenyl-ethyl]-amide;

2–Chloro-6H-thieno[2,3-b]pyrrole-5-carboxylic acid [(1S)-benzyl-2-(1,1-dioxo-1-thiazolidin-3-yl)-2-oxo-ethyl]-amide;

1-{(2S)-[(2–Chloro-6H-thieno[2,3-b]pyrrole-5-carbonyl)-amino]-3-phenyl-propionyl}-piperidine-4-carboxylic acid ethyl ester;

2-bromo-6H-thieno[2,3-b]pyrrole-5-carboxylic acid [(1S)-benzyl-2-(3-hydroxy-azetidin-1-yl)-2-oxo-ethyl]-amide;

2-methyl-4H-furo[3,2-b]pyrrole-5-carboxylic acid [(1S)-benzyl-2-((3R,4S)-dihydroxy-pyrrolidin-1-yl)-2-oxo-ethyl]-amide;

2-trimethylsilanylethynyl-6H-thieno[2,3-b]pyrrole-5-carboxylic acid [(1S)-benzyl-2-(3-hydroxy-azetidin-1-yl)-2-oxo-ethyl]-amide;

2-ethynyl-6H-thieno[2,3-b]pyrrole-5-carboxylic acid [(1S)-benzyl-2-(3-hydroxy-azetidin-1-yl)-2-oxo-ethyl]-amide;

2-fluoro-4H-thieno[3,2-b]pyrrole-5-carboxylic acid [(1S)-benzyl-2-((3R,4S)-dihydroxy-pyrrolidin-1-yl)-2-oxo-ethyl]-amide;

2-Cyano-4H-furo[3,2-b]pyrrole-5-carboxylic acid [(1S)-benzyl-2-(3-hydroxy-azetidin-1-yl)-2-oxo-ethyl]-amide;

2–Chloro-4H-furo[3,2-b]pyrrole-5-carboxylic acid [(1S)-benzyl-2-((3R,4S)-dihydroxy-pyrrolidin-1-yl)-2-oxo-ethyl]-amide;

2-chloro-4H-furo[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

1-{(2S)-[(2-chloro-6H-thieno[2,3-b]pyrrole-5-carbonyl)-amino]-3-phenyl-propionyl}-piperidine-4-carboxylic acid;

3-chloro-4H-thieno[3,2-b]pyrrole-5-carboxylic acid [(1S)-benzyl-2-((3R,4S)-dihydroxy-pyrrolidin-1-yl)-2-oxo-ethyl]-amide;

3-chloro-4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

3-bromo-4H-thieno[3,2-b]pyrrole-5-carboxylic acid [(1S)-benzyl-2-((3R,4S)-dihydroxy-pyrrolidin-1-yl)-2-oxo-ethyl]-amide;

3-bromo-4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

2-chloro-4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

2-chloro-4H-thieno[3,2-b]pyrrole-5-carboxylic acid [(1S)-benzyl-2-((3R,4S)-dihydroxy-pyrrolidin-1-yl)-2-oxo-ethyl]-amide;

3-methyl-4H-thieno[3,2-b]pyrrole-5-carboxylic acid [(1S)-benzyl-2-((3R,4S)-dihydroxy-pyrrolidin-1-yl)-2-oxo-ethyl]-amide;

3-methyl-4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

2-cyano-4H-thieno[3,2-b]pyrrole-5-carboxylic acid [(1S)-benzyl-2-((3R,4S)-dihydroxy-pyrrolidin-1-yl)-2-oxo-ethyl]-amide;

2-cyano-4H-furo[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

3-bromo-4H-furo[3,2-b]pyrrole-5-carboxylic acid [(1S)-benzyl-2-((3R,4S)-dihydroxy-pyrrolidin-1-yl)-2-oxo-ethyl]-amide;

3-bromo-4H-furo[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

4H-1,7-dithia-4-aza-cyclopenta[a]pentalene-5-carboxylic acid [(1S)-benzyl-3-((3R,4S)-dihydroxy-pyrrolidin-1-yl)-(2R)-hydroxy-3-oxo-propyl]-amide;

4H-1,7-dithia-4-aza-cyclopenta[a]pentalene-5-carboxylic acid [(1S)-benzyl-2-((3R,4S)-dihydroxy-pyrrolidin-1-yl)-2-oxo-ethyl]-amide;

2–Chloro-3-methyl-4H-thieno[3,2-b]pyrrole-5-carboxylic acid [(1S)-benzyl-2-((3R,4S)-dihydroxy-pyrrolidin-1-yl)-2-oxo-ethyl]-amide;

2-chloro-3-methyl-4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide;

2-methylsulfanyl-4H-thieno[3,2-b]pyrrole-5-carboxylic acid [(1S)-benzyl-2-((3R,4S)-dihydroxy-pyrrolidin-1-yl)-2-oxo-ethyl]-amide;

2-Bromo-4H-thieno[3,2-b]pyrrole-5-carboxylic acid [(1S)-benzyl-2-(3-hydroxy-azetidin-1-yl)-2-oxo-ethyl]-amide;

2-Bromo-4H-thieno[3,2-b]pyrrole-5-carboxylic acid [(1S)-benzyl-2-(1,1-dioxo-1-thiazolidin-3-yl)-2-oxo-ethyl]-amide;

2-Bromo-4H-thieno[3,2-b]pyrrole-5-carboxylic acid [(1S)-benzyl-2-morpholin-4-yl-2-oxo-ethyl]-amide;

2-bromo-4H-thieno[3,2-b]pyrrole-5-carboxylic acid [(1S)-benzyl-2-((3S,4S)-dihydroxy-pyrrolidin-1-yl)-2-oxo-ethyl]-amide;

2-bromo-4H-thieno[3,2-b]pyrrole-5-carboxylic acid [(1S)-benzyl-2-((3R,4R)-dihydroxy-pyrrolidin-1-yl)-2-oxo-ethyl]-amide; and 2-bromo-4H-thieno[3,2-b]pyrrole-5-carboxylic acid [(1S)-benzyl-2-(4-hydroxy-piperidin-1-yl)-2-oxo-ethyl]-amide, and stereoisomers, pharmaceutically acceptable salts and prodrugs of the compounds, and pharmaceutically acceptable salts of the prodrugs.

Also provided are kits for the treatment of diabetes, insulin resistance, diabetic neuropathy, diabetic nephropathy, diabetic retinopathy, or cataracts in a patient having diabetes, insulin resistance, diabetic neuropathy, diabetic nephropathy, diabetic retinopathy, or cataracts, the kits comprising:

a) a first pharmaceutical composition comprising a compound of Formula I, stereoisomers, pharmaceutically acceptable salts and prodrugs of the compounds of Formula I, and pharmaceutically acceptable salts of the prodrugs;

b) a second pharmaceutical composition comprising a second compound useful for the treatment of diabetes, insulin resistance, diabetic neuropathy, diabetic nephropathy, diabetic retinopathy, or cataracts; and c) a container for containing the first and second compositions.

In a preferred embodiment of the kits, the second compound is selected from: insulin and insulin analogs;
GLP-1 (7–37) (insulinotropin) and GLP-1 (7–36)-$NH_2$;
sulfonylureas and analogs;
biguanides;
$\alpha 2$-antagonists;
imidazolines;
glitazones (thiazolidenediones);
PPAR-gamma agonists;
fatty acid oxidation inhibitors;
$\alpha$-glucosidase inhibitors;
$\beta$-agonists;
phosphodiesterase Inhibitors;
lipid-lowering agents:
antiobesity agents
vanadate, vanadium complexes and peroxovanadium complexes;
amylin antagonists;
glucagon antagonists;
gluconeogenesis inhibitors;
somatostatin analogs and antagonists; and
antilipolytic agents.

In another preferred embodiment of the kits, the second compound is selected from LysPro insulin, GLP-1 (7-37) (insulinotropin), GLP-1 (7-36)-$NH_2$, chlorpropamide, glibenclamide, tolbutamide, tolazamide, acetohexamide, glypizide, glimepiride, repaglinide, meglitinide; metformin, phenformin, buformin, midaglizole, isaglidole, deriglidole, idazoxan, efaroxan, fluparoxan, linogliride, ciglitazone, pioglitazone, englitazone, troglitazone, darglitazone, rosiglitazone, clomoxir, etomoxir, acarbose, miglitol, emiglitate, voglibose, MDL-25,637, camiglibose, MDL-73, 945, BRL 35135, BRL 37344, Ro 16-8714, ICI D7114, CL 316,243, L-386,398; benfluorex, fenfluramine, Naglivan®, acipimox, WAG 994, Symlin™, AC2993 and nateglinide.

In still another preferred embodiment of the kits, the second compound is selected from insulin, sulfonylureas, biguanides, and thiazolidinediones.

Also provided are kits for the treatment of diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, or tissue ischemia in a patient having diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, or tissue ischemia, the kits comprising:

a) a first pharmaceutical composition comprising a compound of Formula I, stereoisomers, pharmaceutically acceptable salts and prodrugs of the compounds of Formula I, and pharmaceutically acceptable salts of the prodrugs;

b) a second pharmaceutical composition comprising a second compound useful for the treatment of diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, or tissue ischemia; and c) a container for containing the first and second compositions.

Also provided are methods of treating diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, or tissue ischemia, the method comprising the step of administering to a patient having diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, or tissue ischemia, a therapeutically effective amount of a compound of Formula I, stereoisomers, pharmaceutically acceptable salts and prodrugs thereof, and pharmaceutically acceptable salts of the prodrugs in combination with at least one additional compound useful for the treatment of diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, or tissue ischemia.

Also provided are pharmaceutical compositions comprising a compound of Formula I, stereoisomers, pharmaceutically acceptable salts and prodrugs thereof, and pharmaceutically acceptable salts of the prodrugs and at least one additional compound useful to treat diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, or tissue ischemia.

DETAILED DESCRIPTION OF THE INVENTION

The present invention relates to compounds of Formula I, stereoisomers of compounds of Formula I, pharmaceutically acceptable salts of compounds of Formula I, prodrugs of compounds of Formula I, and pharmaceutically acceptable salts of the prodrugs of compounds of Formula I. The invention also relates to methods of treatment of diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, and tissue ischemia, particularly myocardial ischemia, and to pharmaceutically acceptable compositions comprising a compound of Formula I, stereoisomers of compounds of Formula I, pharmaceutically acceptable salts of compounds of Formula I, prodrugs of compounds of Formula I, and pharmaceutically acceptable salts of the prodrugs of compounds of Formula I.

Certain terms that are used in this application are defined below.

The term "alkyl" means a straight or branched chain hydrocarbon. Representative examples of alkyl groups include methyl, ethyl, propyl, isopropyl, butyl, isobutyl, tert-butyl, sec-butyl, pentyl, and hexyl. Preferred alkyl groups are $C_1$–$C_8$alkyl.

The term "alkoxy" means an alkyl group bonded to an oxygen atom. Representative examples of alkoxy groups include methoxy, ethoxy, tert-butoxy, propoxy, and isobutoxy. Preferred alkoxy groups are $C_1$–$C_8$alkoxy.

The term "halogen" means chlorine, fluorine, bromine or iodine.

The term "alkenyl" means a branched or straight chain hydrocarbon having one or more carbon-carbon double bonds.

The term "alkynyl" means a branched or straight chain hydrocarbon having one or more carbon-carbon triple bonds.

The term "cycloalkyl" means a cyclic, hydrocarbon. Examples of cycloalkyl groups include cyclopropyl, cyclobutyl, cyclopentyl, cyclohexyl and cycloheptyl. Preferred cycloalkyl groups are $C_3$–$C_8$cyloalkyl. It is also possible for the cycloalkyl group to have one or more double bonds, but is not aromatic. Examples of cycloalkyl groups having double bonds include cyclopentenyl, cyclohexenyl, cyclohexadienyl, cyclobutadienyl, and the like.

The term "perfluoroalkyl" means an alkyl group in which all of the hydrogen atoms have been replaced with fluorine atoms.

The term "acyl" means a group derived from an organic acid (—COOH) by removal of the hydroxy group (—OH).

The term "aryl" means a cyclic, aromatic hydrocarbon. Examples of aryl groups include phenyl and naphthyl.

The term "heteroatom" includes oxygen, nitrogen, sulfur, and phosphorous.

The term "heteroaryl" means a cyclic, aromatic hydrocarbon in which one or more carbon atoms have been replaced with a heteroatom. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, quinolizinyl, isoquinolyl, quinolyl, phthalazinyl, naphthyridinyl, quinoxalinyl, isothiazolyl, and benzo[b]thienyl. Preferred heteroaryl groups are five or six membered rings and contain from one to three heteroatoms.

The term "heterocycloalkyl" means a cycloalkyl group in which one or more of the carbon atoms has been replaced with a heteroatom. If the heterocycloalkyl group contains more than one heteroatom, the heteroatoms may be the same or different. Examples of heterocycloalkyl groups include tetrahydrofuryl, morpholinyl, piperazinyl, piperadyl, and pyrrolidinyl. Preferred heterocycloalkyl groups are five or six membered rings and contain from one to three heteroatoms. It is also possible for the heterocycloalkyl group to have one or more double bonds, but is not aromatic. Examples of heterocycloalkyl groups containing double bonds include dihydrofuran, and the like.

It is also noted that the cyclic ring groups, i.e., aryl, heteroaryl, cycloalkyl, heterocycloalkyl, can comprise more than one ring. For example, the naphthyl group is a fused bicyclic ring system. It is also intended that the present invention include ring groups that have bridging atoms, or ring groups that have a spiro orientation.

Representative examples of five to six membered aromatic rings, optionally having one or two heteroatoms, are phenyl, furyl, thienyl, pyrrolyl, oxazolyl, thiazolyl, imidazolyl, pyrazolyl, isoxazolyl, isothiazolyl, pyridinyl, pyridiazinyl, pyrimidinyl, and pyrazinyl.

Representative examples of partially saturated, fully saturated or fully unsaturated five to eight membered rings, optionally having one to three heteroatoms, are cyclopentyl, cyclohexyl, cycloheptyl, cyclooctyl and phenyl. Further exemplary five membered rings are furyl, thienyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyl, 1,2,5-oxadiazolyl, 1,3,4-oxadiazolyl, 1,2,3-triazolyl, 1,2,4-trizaolyl, 1,3,4-thiadiazolyl, 3H-1,2,3-dioxazolyl, 1,2,4-dioxazolyl, 1,3,2-dioxazolyl, 1,3,4-dioxazolyl, 5H-1,2,5-oxathiazolyl, and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-oxathiazinyl, and 1,4,2-oxadiazinyl.

Further exemplary seven membered rings are azepinyl, oxepinyl, thiepinyl and 1,2,4-triazepinyl.

Further exemplary eight membered rings are cyclooctyl, cyclooctenyl and cyclooctadienyl.

Exemplary bicyclic rings consisting of two fused partially saturated, fully saturated or fully unsaturated five and/or six membered rings, taken independently, optionally having one to four heteroatoms are indolizinyl, indolyl, isoindolyl, indolinyl, cyclopenta(b)pyridinyl, pyrano(3,4-b)pyrrolyl, benzofuryl, isobenzofuryl, benzo(b)thienyl, benzo(c)thienyl, 1H-indazolyl, indoxazinyl, benzoxazolyl, anthranilyl, benzimidazolyl, benzthiazolyl, purinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)-pyridinyl, pyrido(3,2-b)-pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

A cyclic ring group may be bonded to another group in more than one way. If no particular bonding arrangement is specified, then all possible arrangements are intended. For example, the term "pyridyl" includes 2-, 3-, or 4-pyridyl, and the term "thienyl" includes 2-, or 3-thienyl.

The term "substituted" means that a hydrogen atom on an organic molecule has been replaced with a different atom or with a molecule. The atom or molecule replacing the hydrogen atom is called a substituent. Examples of suitable substituents include, halogens, —O$C_1$–$C_8$alkyl, —$C_1$–$C_8$alkyl, —$CF_3$, —$NH_2$, —NH$C_1$–$C_8$alkyl, —N($C_1$–$C_8$alkyl)$_2$, —$NO_2$, —CN, —$CO_2H$, —$CO_2C_1$–$C_8$alkyl, and the like.

The symbol "—" represents a covalent bond.

The term "therapeutically effective amount" means an amount of a compound that ameliorates, attenuates, or eliminates one or more symptom of a particular disease or condition or prevents or delays the onset of one of more symptom of a particular disease or condition.

The term "patient" means animals, such as dogs, cats, cows, horses, sheep, and humans. Particularly preferred patients are mammals. The term patient includes males and females.

The term "pharmaceutically acceptable" means that the carrier, diluent, excipients, and/or salt must be compatible with the other ingredients of the formulation, and not deleterious to the patient.

The phrases "a compound of the present invention, compounds of the present invention, a compound of Formula I, or a compound in accordance with Formula I" and the like, includes the stereoisomers of the compound(s), pharmaceutically acceptable salts of the compound(s), prodrugs of the compound(s), and pharmaceutically acceptable salts of the prodrugs.

The terms "reaction-inert solvent" or "inert solvent" refer to a solvent or mixture of solvents that does not interact with starting materials, reagents, intermediates or products in a manner that adversely affects the desired product.

The terms "treating", "treat" or "treatment" include preventative (e.g., prophylactic) and palliative treatment.

The term "glycogen phosphorylase inhibitor" refers to any substance or agent or any combination of substances and/or agents that reduces, retards, or eliminates the enzymatic action of glycogen phosphorylase. The currently known enzymatic action of glycogen phosphorylase is the degradation of glycogen by catalysis of the reversible reaction of a glycogen macromolecule and inorganic phosphate to glucose-1-phosphate and a glycogen macromolecule which is one glucosyl residue shorter than the original glycogen macromolecule (forward direction of glycogenolysis).

A patient in need of glycogen phosphorylase inhibition is a patient having a disease or condition in which glycogen phosphorylase plays a role in the disease of condition. Examples of patients in need of glycogen phoshphorylase inhibition include patients having diabetes (including Type I and Type II, impaired glucose tolerance, insulin resistance, and the diabetic complications, such a nephropathy, retinopathy, neuropathy and cataracts), hyperglycemia, hypercholesterolemia, hypertension, hyperinsulinemia, hyperlipidemia, atherosclerosis and tissue ischemia.

The characteristics of patients at risk of having atherosclerosis are well known to those skilled in the art and include, patients who have a family history of cardiovascular disease, including hypertension and atherosclerosis, obese patients, patient who exercise infrequently, patients with hypercholesterolemia, patients having high levels of low density lipoprotein (LDL), patients having low levels of high density lipoprotein (HDL), and the like.

Patients at risk of having myocardial ischemia and other tissue ischemias are also well known to those skilled in the art and include patients undergoing or having undergone surgery, trauma or great stress.

The compounds of the present invention are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

In addition, the compounds of the present invention can be administered alone, in combination with other compounds of the present invention, or with other pharmaceutically active compounds. The other pharmaceutically active compounds can be intended to treat the same disease or condition as the compounds of the present invention or a different disease or condition. If the patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered via a tablet, while another is administered via injection or orally as a syrup. All combinations, delivery methods and administration sequences are contemplated.

Since one aspect of the present invention contemplates the treatment of the disease/conditions with a combination of pharmaceutically active agents that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes, bags, and the like. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present invention and other pharmaceutically active agents, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents.

Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. They may also contain opacifying agents, and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferable suppositories, which can be prepared by mixing the compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of a compound of the present invention include ointments, powders, sprays and inhalants. The active compound or compounds are admixed under sterile condition with a physiologically acceptable carrier, and any preservatives, buffers, or propellants that may be required. Opthalmic formulations, eye ointments, powders, and solutions are also contemplated as being within the scope of this invention.

The compounds of the present invention can be administered to a patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is well within the ordinary skill in the art.

The following paragraphs describe exemplary formulations, dosages etc. useful for non-human animals. The administration of a compound of the present invention can be effected orally or non-orally, for example by injection. An amount of a compound of the present invention is administered such that an effective dose is received, generally a daily dose which, when administered orally to an animal is usually between 0.01 and 100 mg/kg of body weight, preferably between 0.1 and 50 mg/kg of body weight. Conveniently, the medication can be carried in the drinking water so that a therapeutic dosage of the agent is ingested with the daily water supply. The agent can be directly metered into drinking water, preferably in the form of a liquid, water-soluble concentrate (such as an aqueous solution of a water soluble salt). Conveniently, the active ingredient can also be added directly to the feed, as such, or in the form of an animal feed supplement, also referred to as a premix or concentrate. A premix or concentrate of therapeutic agent in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the active materials in the finished feed with which the premix is blended. It is important that the compound be thoroughly blended into the premix and, subsequently, the feed. In this respect, the agent may be dispersed or dissolved in a suitable oily vehicle such as soybean oil, corn oil, cottonseed oil, and the like, or in a volatile organic solvent and then blended with the carrier. It will be appreciated that the proportions of active material in the concentrate are capable of wide variation since the amount of agent in the finished feed may be adjusted by blending the appropriate proportion of premix with the feed to obtain a desired level of therapeutic agent.

High potency concentrates may be blended by the feed manufacturer with proteinaceous carrier such as soybean oil meal and other meals, as described above, to produce concentrated supplements which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound according to the invention. The mixtures are thoroughly blended by standard procedures, such as in a twin shell blender, to ensure homogeneity.

If the supplement is used as a top dressing for the feed, it likewise helps to ensure uniformity of distribution of the active material across the top of the dressed feed.

Drinking water and feed effective for increasing lean meat deposition and for improving lean meat to fat ratio are generally prepared by mixing a compound of the invention with a sufficient amount of animal feed to provide from about $10^{-3}$ to about 500 ppm of the compound in the feed or water.

The preferred medicated swine, cattle, sheep and goat feed generally contain from about 1 to about 400 grams of active ingredient per ton of feed, the optimum amount for these animals usually being about 50 to about 300 grams per ton of feed.

The preferred poultry and domestic pet feeds usually contain about 1 to about 400 grams and preferably about 10 to about 400 grams of active ingredient per ton of feed.

For parenteral administration in animals, the compounds of the present invention may be prepared in the form of a paste or a pellet and administered as an implant, usually under the skin of the head or ear of the animal.

In general, parenteral administration involves injection of a sufficient amount of a compound of the present invention to provide the animal with about 0.01 to about 100 mg/kg/day of body weight of the active ingredient. The preferred dosage for poultry, swine, cattle, sheep, goats and domestic pets is in the range of from about 0.1 to about 50 mg/kg/day.

Paste formulations can be prepared by dispersing the active compound in a pharmaceutically acceptable oil such as peanut oil, sesame oil, corn oil or the like.

Pellets containing an effective amount of a compound of the present invention can be prepared by admixing a compound of the present invention with a diluent such as carbowax, carnuba wax, and the like, and a lubricant, such as magnesium or calcium stearate, can be added to improve the pelleting process.

It is, of course, recognized that more than one pellet may be administered to an animal to achieve the desired dose level. Moreover, it has been found that implants may also be made periodically during the animal treatment period in order to maintain the proper active agent in the level animal's body.

The term pharmaceutically acceptable salts, esters, amides, or prodrugs means the carboxylate salts, amino acid addition salts, esters, amides, and prodrugs of the compounds of the present invention that are, within the scope of sound medical judgment, suitable for use with patients without undue toxicity, irritation, allergic response, and the like, commensurate with a reasonable benefit/risk ratio, and effective for their intended use, as well as the zwitterionic forms, where possible, of the compounds of the present invention.

The term "salts" refers to inorganic and organic salts of compounds of the present invention. The salts can be prepared in situ during the final isolation and purification of a compound, or by separately reacting a purified compound in its free base form with a suitable organic or inorganic acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," *J Pharm Sci*, 66:1–19 (1977).

Examples of pharmaceutically acceptable, non-toxic esters of the compounds of the present invention, if applicable, include $C_1$–$C_8$ alkyl esters. Acceptable esters also include $C_5$–$C_7$cycloalkyl esters, as well as arylalkyl esters such as benzyl. $C_1$–$C_4$ alkyl esters are preferred. Esters of compounds of the present invention may be prepared according to methods that are well known in the art.

Examples of pharmaceutically acceptable non-toxic amides of the compounds of the present invention include amides derived from ammonia, primary $C_1$–$C_8$alkyl amines, and secondary $C_1$–$C_8$ dialkyl amines. In the case of secondary amines, the amine may also be in the form of a 5 or 6 membered heterocycloalkyl group containing at least one nitrogen atom. Amides derived from ammonia, $C_1$–$C_3$ primary alkyl amines, and $C_1$–$C_2$ dialkyl secondary amines are preferred. Amides of the compounds of the present invention may be prepared according to methods well known to those skilled in the art.

The term "prodrug" means compounds that are transformed in vivo to yield a compound of Formula I. The transformation may occur by various mechanisms, such as through hydrolysis in blood. A discussion of the use of prodrugs is provided by T. Higuchi and W. Stella, "Prodrugs as Novel Delivery Systems," Vol. 14 of the A. C. S. Symposium Series, and in Bioreversible Carriers in Drug Design, ed. Edward B. Roche, American Pharmaceutical Association and Pergamon Press, 1987.

For example, if the compound of the invention contains a carboxylic acid functional group, a prodrug can comprise an ester formed by the replacement of the hydrogen atom of the acid group with a group such as ($C_1$–$C_8$)alkyl, ($C_2$-$C_{12}$) alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-($C_1$–$C_2$)alkylamino($C_2$–$C_3$)alkyl (such as β-dimethylaminoethyl), carbamoyl-($C_1$–$C_2$)alkyl, N,N-di($C_1$–$C_2$)alkylcarbamoyl-($C_1$–$C_2$)alkyl and piperidino-, pyrrolidino- or morpholino($C_2$–$C_3$)alkyl.

Similarly, if the compound of the present invention comprises an alcohol functional group, a prodrug can be formed by the replacement of the hydrogen atom of the alcohol group with a group such as ($C_1$–$C_6$)alkanoyloxymethyl, 1-(($C_1$–$C_6$)alkanoyloxy)ethyl, 1-methyl-1-(($C_1$–$C_6$) alkanoyloxy)ethyl, ($C_1$–$C_6$)alkoxycarbonyloxymethyl, N-($C_1$–$C_6$)alkoxycarbonylaminomethyl, succinoyl, ($C_1$–$C_6$) alkanoyl, α-amino($C_1$–$C_4$)alkanoyl, arylacyl and α-aminoacyl, or α-aminoacyl-α-aminoacyl, where each α-aminoacyl group is independently selected from the naturally occurring L-amino acids, P(O)(OH)$_2$, —P(O)(O ($C_1$–$C_6$)alkyl)$_2$ or glycosyl (the radical resulting from the removal of a hydroxyl group of the hemiacetal form of a carbohydrate).

If the compound of the present invention comprises an amine functional group, a prodrug can be formed by the replacement of a hydrogen atom in the amine group with a group such as R-carbonyl, RO-carbonyl, NRR'-carbonyl where R and R' are each independently (($C_1$–$C_{10}$)alkyl, ($C_3$–$C_7$)cycloalkyl, benzyl, or R-carbonyl is a natural α-aminoacyl or natural α-aminoacyl-natural α-aminoacyl, —C(OH)C(O)OY wherein (Y is H, ($C_1$–$C_6$)alkyl or benzyl), —C(OY$_0$)Y$_1$ wherein Y$_0$ is ($C_1$–$C_4$) alkyl and Y$_1$ is (($C_1$–$C_6$)alkyl, carboxy($C_1$–$C_6$)alkyl, amino($C_1$–$C_4$)alkyl or mono-N- or di-N,N-($C_1$–$C_6$)alkylaminoalkyl, —C(Y$_2$)Y$_3$ wherein Y$_2$ is H or methyl and Y$_3$ is mono-N- or di-N,N-($C_1$–$C_6$)alkylamino, morpholino, piperidin-1-yl or pyrrolidin-1-yl.

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond, both the cis and trans forms, as well as mixtures, are contemplated.

Diasteromeric mixtures can be separated into their individual stereochemical components on the basis of their physical chemical differences by methods known per se, for example, by chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. Also, some of the compounds of this invention may be atropisomers (e.g., substituted biaryls) and are considered as part of this invention.

The compounds of the present invention may exist in unsolvated as well as solvated forms with pharmaceutically acceptable solvents such as water, ethanol, and the like. The present invention contemplates and encompasses both the solvated and unsolvated forms.

It is also possible that compounds of the present invention may exist in different tautomeric forms. All tautomers of compounds of the present invention are contemplated. For example, all of the tautomeric forms of the imidazole moiety are included in this invention. Also, for example, all keto-enol or imine-enamine forms of the compounds are included in this invention.

Those skilled in the art will recognize that the compound names contained herein may be based on a particular tautomer of a compound. While the name for only a particular tautomer may be used, it is intended that all tautomers are encompassed by the name of the particular tautomer and included as part of the invention.

It is also intended that the invention disclosed herein encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention that contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detection. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples below, by substituting a readily available isotopically labelled reagent for a non-isotopically labelled reagent.

In general the compounds of this invention can be made by processes which include processes analogous to those known in the chemical arts, particularly in light of the description contained herein.

In another aspect, the present invention concerns the treatment of diabetes, including impaired glucose tolerance, insulin resistance, insulin dependent diabetes mellitus (Type I) and non-insulin dependent diabetes mellitus (NIDDM or Type II). Also included in the treatment of diabetes are the treatment of the diabetic complications, such as neuropathy, nephropathy, retinopathy or cataracts.

Diabetes can be treated by administering to a patient having diabetes (Type I or Type II), insulin resistance, impaired glucose tolerance, or any of the diabetic complications such as neuropathy, nephropathy, retinopathy or cataracts, a therapeutically effective amount of a compound of the present invention. It is also contemplated that diabetes be treated by administering a compound of the present invention or an other glycogen phosphorylase inhibitor in combination with an additional agent that can be used to treat diabetes and/or obesity. Preferred gylcogen phosphorylase inhibitors that are useful in combination with other agents useful to treat diabetes and/or obesity include those of Formula I. Additional preferred gylcogen phosphorylase inhibitors are disclosed in PCT publications WO 96/39384 and WO 96/39385.

Representative agents that can be used to treat diabetes include insulin and insulin analogs: (e.g., LysPro insulin. inhaled formulations comprising insulin); GLP-1 (7-37) (insulinotropin) and GLP-1 (7-36)-$NH_2$; sulfonylureas and analogs: chlorpropamide, glibenclamide, tolbutamide, tolazamide, acetohexamide, glypizide, glimepiride, repaglinide, meglitinide; biguanides: metformin, phenformin, buformin; ($\alpha$2-antagonists and imidazolines: midaglizole, isaglidole, deriglidole, idazoxan, efaroxan, fluparoxan; other insulin secretagogues: linogliride, insulinotropin, exendin-4, BTS-67582, A-4166; glitazones: ciglitazone, pioglitazone, englitazone, troglitazone, darglitazone, rosiglitazone; PPAR-gamma agonists; RXR agonists: JTT-501, MCC-555, MX-6054, DRF2593,GI-262570, KRP-297, LG100268; fatty acid oxidation inhibitors: clomoxir, etomoxir; $\alpha$-glucosidase inhibitors: precose, acarbose, miglitol, emiglitate, voglibose, MDL-25,637, camiglibose, MDL-73,945; $\beta$-agonists: BRL 35135, BRL 37344, Ro 16-8714, ICI D7114, CL 316,243, TAK-667, AZ40140; phosphodiesterase inhibitors, both cAMP and cGMP type: sildenafil, L686398: L-386,398; lipid-lowering agents: benfluorex, atorvastatin; antiobesity agents: fenfluramine, orlistat, sibutramine; vanadate and vanadium complexes (e.g., Naglivan®) and peroxovanadium complexes; amylin antagonists: pramlintide, AC-137; lipoxygenase inhibitors: masoprocal; somatostatin analogs: BM-23014, seglitide, octreotide; glucagon antagonists: BAY 276–9955; insulin signaling agonists, insulin mimetics, PTP1 B inhibitors: L-783281, TER1 7411, TER17529; gluconeogenesis inhibitors: GP3034; somatostatin analogs and antagonists; antilipolytic agents: nicotinic acid, acipimox, WAG 994; glucose transport stimulating agents: BM-130795; glucose synthase kinase inhibitors: lithium chloride, CT98014, CT98023; galanin receptor agonisnts; MTP inhibitors such as those disclosed in U.S. provisional patent application number 60/164,803; growth hormone secretagogues such as those disclosed in PCT publication numbers WO 97/24369 and WO 98/58947; NPY antagonists: PD-160170, BW-383, BW1229, CGP-71683A, NGD 95–1, L-152804; Anorectic agents including 5-HT and 5-HT2C receptor antagonists and/or mimetics: dexfenfluramine, Prozac®, Zoloft®; CCK receptor agonists: SR-27897B; galanin receptor antagonists; MCR-4 antagonists: HP-228; leptin or mimetics: leptin; 11-beta-hydroxysteroid dehydrogenase type-I inhibitors; urocortin mimetics, CRF antagonists, and CRF binding proteins: RU-486, urocortin. Other anti-diabetic agents that can be used in combination with a glycogen phosphorylase inhibitor include ergoset and D-chiroinositol. Any combination of agents can be administered as described above.

In addition to the categories and compounds mentioned above, gylcogen phosphorylase inhibitors, preferrably the compounds of the present invention, can be administered in combination with thyromimetic compounds, aldose reductase inhibitors, glucocorticoid receptor antagonists, NHE-1 inhibitors, or sorbitol dehydrogenase inhibitors, or combinations thereof, to treat or prevent diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, or tissue ischemia, particularly myocardial ischemia.

It is generally accepted that thyroid hormones, specifically, biologically active iodothyronines, are critical to normal development and to maintaining metabolic homeostasis. Thyroid hormones stimulate the metabolism of cholesterol to bile acids and enhance the lipolytic responses of fat cells to other hormones. U.S. Pat. Nos. 4,766,121; 4,826,876; 4,910,305; and 5,061,798 disclose certain thyroid hormone mimetics (thyromimetics), namely, 3,5-dibromo-3'-[6-oxo-3(1H)-pyridazinylmethyl]-thyronines. U.S. Pat. No. 5,284,971 discloses certain thyromimetic cholesterol lowering agents, namely, 4-(3-Cyclohexyl-4-hydroxy or -methoxy phenylsulfonyl)-3,5 dibromophenylacetic compounds. U.S. Pat. Nos. 5,401,772; 5,654, 468; and 5,569,674 disclose certain thyromimetics that are lipid lowering agents, namely, heteroacetic acid derivatives. In addition, certain oxamic acid derivatives of thyroid hormones are known in the art. For example, N. Yokoyama, et al. in an article published in the *Journal of Medicinal Chemistry,* 38 (4): 695–707 (1995) describe replacing a —$CH_2$ group in a naturally occurring metabolite of $T_3$ with an —NH group resulting in —HNCOCO$_2$H. Likewise, R. E. Steele et al. in an article published in International Congressional Service (*Atherosclerosis X*) 1066: 321–324 (1995) and Z. F. Stephan et al. in an article published in *Atherosclerosis,* 126: 53–63 (1996), describe certain oxamic acid derivatives useful as lipid-lowering thyromimetic agents, yet devoid of undesirable cardiac activities. Other useful thyromimetics that can be used in combination with a glycogen phosphorylase inhibitor include CGS-26214.

Each of the thyromimetic compounds referenced above and other thyromimetic compounds can be used in combination with the compounds of the present invention to treat or prevent diabetes, insulin resistance, diabetic neuropathy, diabetic nephropathy, diabetic retinopathy, cataracts hyperglycemia, hypercholesterolemia, hypertension, hyperinsulinemia, hyperlipidemia, atherosclerosis, or tissue ischemia.

The compounds of the present invention can also be used in combination with aldose reductase inhibitors. Aldose reductase inhibitors constitute a class of compounds that have become widely known for their utility in preventing and treating conditions arising from complications of diabetes, such as diabetic neuropathy and nephropathy. Such compounds are well known to those skilled in the art and are readily identified by standard biological tests. For example, the aldose reductase inhibitors zopolrestat, 1-phthalazineacetic acid, 3,4-dihydro-4-oxo-3-[[5-(trifluoromethyl)-2-benzothiazolyl]methyl]-, and related compounds are described in U.S. Pat. No. 4,939,140 to Larson et al.

Aldose reductase inhibitors have been taught for use in lowering lipid levels in mammals. See, for example, U.S. Pat. No. 4,492,706 to Kallai-sanfacon and EP 0 310 931 A2 (Ethyl Corporation).

U.S. Pat. No. 5,064,830 to Going discloses the use of certain oxophthalazinyl acetic acid aldose reductase inhibitors, including zopolrestat, for lowering of blood uric acid levels.

Commonly assigned U.S. Pat. No. 5,391,551 discloses the use of certain aldose reductase inhibitors, including zopolrestat, for lowering blood lipid levels in humans. The disclosure teaches that therapeutic utilities derive from the treatment of diseases caused by an increased level of triglycerides in the blood, such diseases include cardiovascular disorders such as thrombosis, arteriosclerosis, myocardial infarction, and angina pectoris. A preferred aldose reductase inhibitor is 1-phthalazineacetic acid, 3,4-dihydro-4-oxo-3-[[5-trifluoromethyl)-2-benzothiazolyl]methyl]-, also known as zopolrestat.

The term aldose reductase inhibitor refers to compounds that inhibit the bioconversion of glucose to sorbitol, which is catalyzed by the enzyme aldose reductase.

Any aldose reductase inhibitor may be used in a combination with a compound of the present invention. Aldose reductase inhibition is readily determined by those skilled in the art according to standard assays (J. Malone, *Diabetes*, 29:861–864 (1980). "Red Cell Sorbitol, an Indicator of Diabetic Control"). A variety of aldose reductase inhibitors are described herein; however, other aldose reductase inhibitors useful in the compositions and methods of this invention will be known to those skilled in the art.

The activity of an aldose reductase inhibitor in a tissue can be determined by testing the amount of aldose reductase inhibitor that is required to lower tissue sorbitol (i.e., by inhibiting the further production of sorbitol consequent to blocking aldose reductase) or lower tissue fructose (by inhibiting the production of sorbitol consequent to blocking aldose reductase and consequently the production of fructose.

Accordingly, examples of aldose reductase inhibitors useful in the compositions, combinations and methods of the present invention include:

1. 3-(4-bromo-2-fluorobenzyl)-3,4-dihydro-4-oxo-1-phthalazineacetic acid (ponalrestat, U.S. Pat. No. 4,251,528);
2. N[[(5-trifluoromethyl)-6-methoxy-1-naphthalenyl] thioxomethyl]-N-methylglycine (tolrestat, U.S. Pat. No. 4,600,724);
3. 5-[(Z,E)-β-methylcinnamylidene]-4-oxo-2-thioxo-3-thiazolideneacetic acid (epalrestat, U.S. Pat. Nos. 4,464,382, 4,791,126, 4,831,045);
4. 3-(4-bromo-2-fluorobenzyl)-7–Chloro-3,4-dihydro-2,4-dioxo-1(2H)-quinazolineacetic acid (zenarestat, U.S. Pat. Nos. 4,734,419, and 4,883,800);
5. 2R,4R-6,7-dichloro-4-hydroxy-2-methylchroman-4-acetic acid (U.S. Pat. No. 4,883,410);
6. 2R,4R-6,7-dichloro-6-fluoro-4-hydroxy-2-methylchroman-4-acetic acid (U.S. Pat. No. 4,883,410);
7. 3,4-dihydro-2,8-diisopropyl-3-oxo-2H-1,4-benzoxazine-4-acetic acid (U.S. Pat. No. 4,771,050);
8. 3,4-dihydro-3-oxo-4-[(4,5,7-trifluoro-2-benzothiazolyl) methyl]-2H-1,4-benzothiazine-2-acetic acid (SPR-210, U.S. Pat. No. 5,252,572);
9. N-[3,5-dimethyl-4-[(nitromethyl)sulfonyl]phenyl]-2-methyl-benzeneacetamide (ZD5522, U.S. Pat. Nos. 5,270,342 and 5,430,060);
10. (S)-6-fluorospiro[chroman-4,4'-imidazolidine]-2,5'-dione (sorbinil, U.S. Pat. No. 4,130,714);
11. d-2-methyl-6-fluoro-spiro(chroman-4',4'-imidazolidine)-2',5'-dione (U.S. Pat. No. 4,540,704);
12. 2-fluoro-spiro(9H-fluorene-9,4'-imidazolidine)2',5'-dione (U.S. Pat. No. 4,438,272);
13. 2,7-di-fluoro-spiro(9H-fluorene-9,4'-imidazolidine)2',5'-dione (U.S. Pat. Nos. 4,436,745, 4,438,272);
14. 2,7-di-fluoro-5-methoxy-spiro(9H-fluorene-9,4'-imidazolidine)2',5'-dione (U.S. Pat. Nos. 4,436,745, 4,438,272);
15. 7-fluoro-spiro(5H-indenol[1,2-b]pyridine-5,3'-pyrrolidine)2,5'-dione (U.S. Pat. Nos. 4,436,745, 4,438, 272);
16. d-cis-6'-chloro-2',3'-dihydro-2'-methyl-spiro-(imidazolidine-4,4'-4'-H-pyrano(2,3-b)pyridine)-2,5-dione (U.S. Pat. No. 4,980,357);
17. spiro[imidazolidine-4,5'(6H)-quinoline]2,5-dione-3'-chloro-7',8'-dihydro-7'-methyl-(5'-cis)(U.S. Pat. No. 5,066,659);
18. (2S,4S)-6-fluoro-2',5'-dioxospiro(chroman-4,4'-imidazolidine)-2-carboxamide (U.S. Pat. No. 5,447,946); and
19. 2-[(4-bromo-2-fluorophenyl)methyl]-6-fluorospiro [isoquinoline-4(1H),3'-pyrrolidine]-1,2',3,5'(2H)-tetrone (ARI-509, U.S. Pat. No. 5,037,831).

Other aldose reductase inhibitors include compounds having formula Ia below

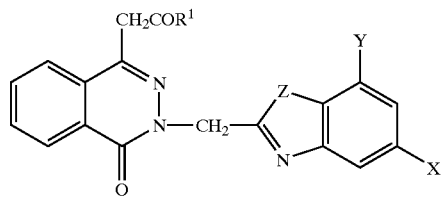

Ia or a pharmaceutically acceptable salt or prodrug thereof, wherein

Z is O or S;

$R^1$ is hydroxy or a group capable of being removed in vivo to produce a compound of formula I wherein $R^1$ is OH; and X and Y are the same or different and are selected from hydrogen, trifluoromethyl, fluoro, and chloro.

A preferred subgroup within the above group of aldose reductase inhibitors includes numbered compounds 1, 2, 3, 4, 5, 6, 9, 10, and 17, and the following compounds of Formula Ia:

20. 3,4-dihydro-3-(5-fluorobenzothiazol-2-ylmethyl)-4-oxophthalazin-1-yl-acetic acid [$R^1$=hydroxy; X=F; Y=H];
21. 3-(5,7-difluorobenzothiazol-2-ylmethyl)-3,4-dihydro-4-oxophthalazin-1-ylacetic acid [$R^1$=hydroxy; X=Y=F];
22. 3-(5–Chlorobenzothiazol-2-ylmethyl)-3,4-dihydro-4-oxophthalazin-1-ylacetic acid [$R^1$=hydroxy; X=Cl; Y=H];
23. 3-(5,7-dichlorobenzothiazol-2-ylmethyl)-3,4-dihydro-4-oxophthalazin-1-ylacetic acid [$R^1$=hydroxy; X=Y=Cl];
24. 3,4-dihydro-4-oxo-3-(5-trifluoromethylbenzoxazol-2-ylmethyl)phthalazin-1-ylacetic acid [$R^1$=hydroxy; X=CF$_3$; Y=H];
25. 3,4-dihydro-3-(5-fluorobenzoxazol-2-ylmethyl)-4-oxophthalazin-1-yl-acetic acid [$R^1$=hydroxy; X=F; Y=H];
26. 3-(5,7-difluorobenzoxazol-2-ylmethyl)-3,4-dihydro-4-oxophthalazin-1-ylacetic acid [$R^1$=hydroxy; X=Y=F];
27. 3-(5–Chlorobenzoxazol-2-ylmethyl)-3,4-dihydro-4-oxophthalazin-1-ylacetic acid [$R^1$=hydroxy; X=Cl; Y=H];

28. 3-(5,7-dichlorobenzoxazol-2-ylmethyl)-3,4-dihydro-4-oxophthalazin-1-ylacetic acid [$R^1$=hydroxy; X=Y=Cl]; and
29. zopolrestat; 1-phthalazineacetic acid, 3,4-dihydro-4-oxo-3-[[5-(trifluoromethyl)-2-benzothiazolyl]methyl]- [$R^1$=hydroxy; X=trifluoromethyl; Y=H].

In compounds 20–23, and 29 Z is S. In compounds 24–28, Z is O.

Of the above subgroup, compounds 20–29 are more preferred with 29 especially preferred. Procedures for making the aldose reducatase inhibitors of formula Ia can be found in PCT publication number WO 99/26659.

Each of the aldose reductase inhibitors referenced above and other aldose reductase inhibitors can be used in combination with the compounds of the present invention to treat diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, or tissue ischemia.

The compounds of the present invention can also be used in combination with glucocorticoid receptor antagonists. The glucocorticoid receptor (GR) is present in glucocorticoid responsive cells where it resides in the cytosol in an inactive state until it is stimulated by an agonist. Upon stimulation the glucocorticoid receptor translocates to the cell nucleus where it specifically interacts with DNA and/or protein(s) and regulates transcription in a glucocorticoid responsive manner. Two examples of proteins that interact with the glucocorticoid receptor are the transcription factors, API and NFκ-B. Such interactions result in inhibition of API- and NFκ-B-mediated transcription and are believed to be responsible for the anti-inflammatory activity of endogenously administered glucocorticoids. In addition, glucocorticoids may also exert physiologic effects independent of nuclear transcription. Biologically relevant glucocorticoid receptor agonists include cortisol and corticosterone. Many synthetic glucocorticoid receptor agonists exist including dexamethasone, prednisone and prednisilone. By definition, glucocorticoid receptor antagonists bind to the receptor and prevent glucocorticoid receptor agonists from binding and eliciting GR mediated events, including transcription. RU486 is an example of a non-selective glucocorticoid receptor antagonist. GR antagonists can be used in the treatment of diseases associated with an excess or a deficiency of glucocorticoids in the body. As such, they may be used to treat the following: obesity, diabetes, cardiovascular disease, hypertension, Syndrome X, depression, anxiety, glaucoma, human immunodeficiency virus (HIV) or acquired immunodeficiency syndrome (AIDS), neurodegeneration (for example, Alzheimer's and Parkinson's), cognition enhancement, Cushing's Syndrome, Addison's Disease, osteoporosis, frailty, inflammatory diseases (such as osteoarthritis, rheumatoid arthritis, asthma and rhinitis), tests of adrenal function, viral infection, immunodeficiency, immunomodulation, autoimmune diseases, allergies, wound healing, compulsive behavior, multi-drug resistance, addiction, psychosis, anorexia, cachexia, post-traumatic stress syndrome, post-surgical bone fracture, medical catabolism and prevention of muscle frailty. Examples or GR antagonists that can be used in combination with a compound of the present invention include compounds of formula Ib below:

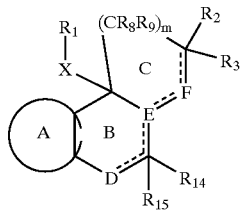

Ib an isomer thereof, a prodrug of said compound or isomer, or a pharmaceutically acceptable salt of said compound, isomer or prodrug; wherein m is 1 or 2;
——— represents an optional bond;
A is selected from the group consisting of

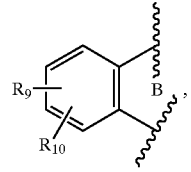

A-1

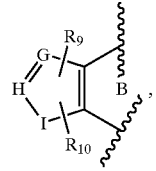

A-2

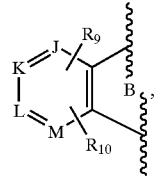

A-3

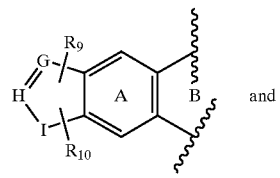

A-4 and

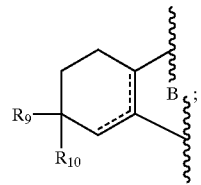

A-5

D is $CR_7$, $CR_7R_{16}$, N, $NR_7$ or O;
E is C, $CR_6$ or N;
F is $CR_4$, $CR_4R_5$ or O;
G, H and I together with 2 carbon atoms from the A-ring or 2 carbon atoms from the B-ring form a 5-membered heterocyclic ring comprising one or more N, O or S atoms; provided that there is at most one of O and S per ring; J, K, L and M together with 2 carbon atoms from the B-ring forms a 6-membered heterocyclic ring comprising 1 or more N atoms;
X is a) absent, b) —$CH_2$—, c) —CH(OH)— or d) —C(O)—;

$R_1$ is a) —H, b) —Z—CF$_3$, c) —(C$_1$–C$_6$)alkyl, d) —(C$_2$–C$_6$)alkenyl, e) —(C$_2$–C$_6$)alkynyl, f) —CHO, g) —CH=N—OR$_{12}$, h) —Z—C(O)OR$_{12}$, i) —Z—C(O)—NR$_{12}$R$_{13}$, j) —Z—C(O)—NR$_{12}$—Z-het, k) —Z—NR$_{12}$R$_{13}$, l) —Z—NR$_{12}$het, m) —Z-het, n) —Z—O-het, o) —Z-aryl', p) —Z—O-aryl', q) —CHOH-aryl' or r) —C(O)-aryl' wherein aryl' in substituents o) to r) is substituted independently with 0, 1 or 2 of the following: —Z—OH, —Z—NR$_{12}$R$_{13}$, —Z—NR$_{12}$-het, —C(O)NR$_{12}$R$_{13}$, —C(O)O(C$_1$–C$_6$)alkyl, —C(O)OH, —C(O)-het, —NR$_{12}$—C(O)—(C$_1$–C$_6$)alkyl, —NR$_{12}$—C(O)—(C$_2$–C$_6$)alkenyl, —NR$_{12}$—C(O)—(C$_2$–C$_6$)alkynyl, —NR$_{12}$—C(O)—Z-het, —CN, —Z-het, —O—(C$_1$–C$_3$)alkyl-C(O)—NR$_{12}$R$_{13}$, —O—(C$_1$–C$_3$)alkyl-C(O)O(C$_1$–C$_6$)alkyl, —NR$_{12}$—Z—C(O)O(C$_1$–C$_6$)alkyl, —N(Z—C(O)O(C$_1$–C$_6$)alkyl)$_2$, —NR$_{12}$—Z—C(O)—NR$_{12}$R$_{13}$, —Z—NR$_{12}$—SO$_2$—R$_{13}$, —NR$_{12}$—SO$_2$-het, —C(O)H, —Z—NR$_{12}$—Z—O(C$_1$–C$_6$)alkyl, —Z—NR$_{12}$—Z—NR$_{12}$R$_{13}$, —Z—NR$_{12}$—(C$_3$–C$_6$)cycloalkyl, —Z—N(Z—O(C$_1$–C$_6$)alkyl)$_2$, —SO$_2$R$_{12}$, —SOR$_{12}$, —SR$_{12}$, —SO$_2$NR$_{12}$R$_{13}$, —O—C(O)—(C$_1$–C$_4$)alkyl, —O—SO$_2$—(C$_1$–C$_4$)alkyl, -halo or —CF$_3$;

Z for each occurrence is independently a) —(C$_0$–C$_6$)alkyl, b) —(C$_2$–C$_6$)alkenyl or c) —(C$_2$–C$_6$)alkynyl;

$R_2$ is a) —H, b) -halo, c) —OH, d) —(C$_1$–C$_6$)alkyl substituted with 0 or 1 —OH, e) —NR$_{12}$R$_{13}$, f) —Z—C(O)O(C$_1$–C$_6$)alkyl, g) —Z—C(O)NR$_{12}$R$_{13}$, h) —O—(C$_1$–C$_6$)alkyl, i) —Z—O—C(O)—(C$_1$–C$_6$)alkyl, j) —Z—O—(C$_1$–C$_3$)alkyl-C(O)—NR$_{12}$R$_{13}$, k) —Z—O—(C$_1$–C$_3$)alkyl-C(O)—O(C$_1$–C$_6$)alkyl, l) —O—(C$_2$–C$_6$)alkenyl, m) —O—(C$_2$–C$_6$)alkynyl, n) —O—Z-het, o) —COOH, p) —C(OH)R$_{12}$R$_{13}$ or q) —Z—CN;

$R_3$ is a) —H, b) —(C$_1$–C$_{10}$)alkyl wherein 1 or 2 carbon atoms, other than the connecting carbon atom, may optionally be replaced with 1 or 2 heteroatoms independently selected from S, O and N and wherein each carbon atom is substituted with 0, 1 or 2 R$_y$, c) —(C$_2$–C$_{10}$)alkenyl substituted with 0, 1 or 2 R$_y$, d) —(C$_2$–C$_{10}$)alkynyl wherein 1 carbon atom, other than the connecting carbon atom, may optionally be replaced with 1 oxygen atom and wherein each carbon atom is substituted with 0, 1 or 2 R$_y$, e) —CH=C=CH$_2$, f) —CN, g) —(C$_3$–C$_6$)cycloalkyl, h) —Z-aryl, i) —Z-het, j) —C(O)O(C$_1$–C$_6$)alkyl, k) —O(C$_1$–C$_6$)alkyl, l) —Z—S—R$_{12}$, m) —Z—S(O)—R$_{12}$, n) —Z—S(O)$_2$-R$_{12}$, o) —CF$_3$ p) —NR$_{12}$O—(C$_1$–C$_6$)alkyl or q) —CH$_2$OR$_y$;

provided that one of $R_2$ and $R_3$ is absent when there is a double bond between CR$_2$R$_3$ (the 7 position) and the F moiety (the 8 position) of the C-ring;

$R_y$ for each occurrence is independently a) —OH, b) -halo, c) —Z—CF$_3$, d) —Z—CF(C$_1$–C$_3$ alkyl)$_2$, e) —CN, f) —NR$_{12}$R$_{13}$, g) —(C$_3$–C$_6$)cycloalkyl, h) —(C$_3$–C$_6$)cycloalkenyl, i) —(C$_0$–C$_3$)alkyl-aryl, j) -het or k) —N$_3$;

or $R_2$ and $R_3$ are taken together to form a) =CHR$_{11}$, b) =NOR$_{11}$, c) =O, d) =N—NR$_{12}$, e) =N—NR$_{12}$—C(O)—R$_{12}$, f) oxiranyl or g) 1,3-dioxolan-4-yl;

$R_4$ and $R_5$ for each occurrence are independently a) —H, b) —CN, c) —(C$_1$–C$_6$)alkyl substituted with 0 to 3 halo, d) —(C$_2$–C$_6$)alkenyl substituted with 0 to 3 halo, e) —(C$_2$–C$_6$)alkynyl substituted with 0 to 3 halo, f) —O—(C$_1$–C$_6$)alkyl substituted with 0 to 3 halo, g) —O—(C$_2$–C$_6$)alkenyl substituted with 0 to 3 halo, h) —O—(C$_2$–C$_6$)alkynyl substituted with 0 to 3 halo, i) -halo, j) —OH, k) (C$_3$–C$_6$)cycloalkyl or l) (C$_3$–C$_6$)cycloalkenyl;

or $R_4$ and $R_5$ are taken together to form =O;

$R_6$ is a) —H, b) —CN, c) —(C$_1$–C$_6$)alkyl substituted with 0 to 3 halo, d) —(C$_2$–C$_6$)alkenyl substituted with 0 to 3 halo, e) —(C$_2$–C$_6$)alkynyl substituted with 0 to 3 halo or f) —OH;

$R_7$ and $R_{16}$ for each occurrence are independently a) —H, b) -halo, c) —CN, d) —(C$_1$–C$_6$)alkyl substituted with 0 to 3 halo, e) —(C$_2$–C$_6$)alkenyl substituted with 0 to 3 halo or f) —(C$_2$–C$_6$)alkynyl substituted with 0 to 3 halo; provided that $R_7$ is other than —CN or -halo when D is NR$_7$;

or $R_7$ and $R_{16}$ are taken together to form =O;

$R_8$, $R_9$, $R_{14}$ and $R_{15}$ for each occurrence are independently a) —H, b) -halo, c) (C$_1$–C$_6$)alkyl substituted with 0 to 3 halo, d) —(C$_2$–C$_6$)alkenyl substituted with 0 to 3 halo, e) —(C$_2$–C$_6$)alkynyl substituted with 0 to 3 halo, f) —CN, g) —(C$_3$–C$_6$)cycloalkyl, h) —(C$_3$–C$_6$)cycloalkenyl, i) —OH, j) —O—(C$_1$–C$_6$)alkyl, k) —O—(C$_1$–C$_6$)alkenyl, l) —O—(C$_1$–C$_6$)alkynyl, m) —NR$_{12}$R$_{13}$, n) —C(O)OR$_{12}$ or o) —C(O)NR$_{12}$R$_{13}$;

or $R_8$ and $R_9$ are taken together on the C-ring to form =O; provided that when m is 2, only one set of $R_8$ and $R_9$ are taken together to form =O;

or $R_{14}$ and $R_{15}$ are taken together to form =O; provided that when $R_{14}$ and $R_{15}$ are taken together to form =O, D is other than CR$_7$ and E is other than C;

$R_{10}$ is a) —(C$_1$–C$_{10}$)alkyl substituted with 0 to 3 substituents independently selected from -halo, —OH and —N$_3$, b) —(C$_2$–C$_{10}$)alkenyl substituted with 0 to 3 substituents independently selected from -halo, —OH and —N$_3$, c) —(C$_2$–C$_{10}$)alkynyl substituted with 0 to 3 substituents independently selected from -halo, —OH and —N$_3$, d) -halo, e) —Z—CN, f) —OH, g) —Z-het, h) —Z—NR$_{12}$R$_{13}$, i) —Z—C(O)-het, j) —Z—C(O)—(C$_1$–C$_6$)alkyl, k) —Z—C(O)—NR$_{12}$R$_{13}$, l) —Z—C(O)—NR$_{12}$—Z—CN, m) —Z—C(O)—NR$_{12}$—Z-het, n) —Z—C(O)—NR$_{12}$—Z-aryl, o) —Z—C(O)—NR$_{12}$—Z—NR$_{12}$R$_{13}$, p) —Z—C(O)—NR$_{12}$—Z—O(C$_1$–C$_6$)alkyl, q) —(C$_1$–C$_6$)alkyl-C(O)OH, r) —Z—C(O)O(C$_1$–C$_6$)alkyl, s) —Z—O—(C$_0$–C$_6$)alkyl-het, t) —Z—O—(C$_0$–C$_6$)alkyl-aryl, u) —Z—O—(C$_1$–C$_6$)alkyl substituted with 0 to 2 R$_x$, v) —Z—O—(C$_1$–C$_6$)alkyl-CH(O), w) —Z—O—(C$_1$–C$_6$)alkyl-NR$_{12}$-het, x) —Z—O—Z-het-Z-het, y) —Z—O—Z-het-Z—NR$_{12}$R$_{13}$, z) —Z—O—Z-het-C(O)-het, a1) —Z—O—Z—C(O)-het, b1) —Z—O—Z—C(O)-het, c1) —Z—O—Z—C(O)—(C$_1$–C$_6$)alkyl, d1) —Z—O—Z—C(S)—NR$_{12}$R$_{13}$, e1) —Z—O—Z—C(O)—NR$_{12}$R$_{13}$, f1) —Z—O—Z—(C$_1$–C$_3$)alkyl-C(O)—NR$_{12}$R$_{13}$, g1) —Z—O—Z—C(O)—O(C$_1$–C$_6$)alkyl, h1) —Z—O—Z—C(O)—OH, i1) —Z—O—Z—C(O)—NR$_{12}$—O(C$_1$–C$_6$)alkyl, j1) —Z—O—Z—C(O)—NR$_{12}$—OH, k1) —Z—O—Z—C(O)—NR$_{12}$—Z—NR$_{12}$R$_{13}$, i1) —Z—O—Z—C(O)—NR$_{12}$—Z-het, m1) —Z—O—Z—C(O)—NR$_{12}$—SO$_2$—(C$_1$–C$_6$)alkyl, n1) —Z—O—Z—C(=NR$_{12}$)(NR$_{12}$R$_{13}$), o1) —Z—O—Z—C(=NOR$_{12}$)(NR$_{12}$R$_{13}$), p1) —Z—NR$_{12}$—C(O)—O—Z—NR$_{12}$R$_{13}$, q1) —Z—S—C(O)—NR$_{12}$R$_{13}$, r1) —Z—O—SO$_2$—(C$_1$–C$_6$)alkyl, s1) —Z—O—SO$_2$-aryl, t1) —Z—O—SO$_2$—NR$_{12}$R$_{13}$, u1) —Z—O—SO$_2$—CF$_3$, v1) —Z—NR$_{12}$C(O)OR$_{13}$ or w1) —Z—NR$_{12}$C(O)R$_{13}$;

or $R_9$ and $R_{10}$ are taken together on the moiety of formula A-5 to form a) =O or b) =NOR$_{12}$;

$R_{11}$ is a) —H, b) —(C$_1$–C$_5$)alkyl, c) —(C$_3$–C$_6$)cycloalkyl or d) —(C$_0$–C$_3$)alkyl-aryl;

$R_{12}$ and $R_{13}$ for each occurrence are each independently a) —H, b) —(C$_1$–C$_6$)alkyl wherein 1 or 2 carbon atoms, other than the connecting carbon atom, may optionally be replaced with 1 or 2 heteroatoms independently selected from S, O and N and wherein each carbon atom is substituted with 0 to 6 halo, c) —($C_2$–$C_6$)alkenyl substituted with 0 to 6 halo or d) —($C_1$–$C_6$)alkynyl wherein 1 carbon atom, other than the connecting carbon atom, may optionally be replaced with 1 oxygen atom and wherein each carbon atom is substituted with 0 to 6 halo;

or $R_{12}$ and $R_{13}$ are taken together with N to form het;

or $R_6$ and $R_{14}$ or $R_{15}$ are taken together to form 1,3-dioxolanyl;

aryl is a) phenyl substituted with 0 to 3 $R_x$, b) naphthyl substituted with 0 to 3 $R_x$ or c) biphenyl substituted with 0 to 3 $R_x$;

het is a 5-, 6- or 7-membered saturated, partially saturated or unsaturated ring containing from one (1) to three (3) heteroatoms independently selected from the group consisting of nitrogen, oxygen and sulfur; and including any bicyclic group in which any of the above heterocyclic rings is fused to a benzene ring or another heterocycle; and the nitrogen may be in the oxidized state giving the N-oxide form; and substituted with 0 to 3 $R_x$;

$R_x$ for each occurrence is independently a) -halo, b) —OH, c) —($C_1$–$C_6$)alkyl, d) —($C_2$–$C_6$)alkenyl, e) —($C_2$–$C_6$)alkynyl, f) —O($C_1$–$C_6$)alkyl, g) —O($C_2$–$C_6$)alkenyl, h) —O($C_2$–$C_6$)alkynyl, i) —($C_0$–$C_6$)alkyl-$NR_{12}R_{13}$, j) —C(O)—$NR_{12}R_{13}$, k) —Z—$SO_2R_{12}$, l) —Z—$SOR_{12}$, m) —Z—$SR_{12}$, n) —$NR_{12}$—$SO_2R_{13}$, o) —$NR_{12}$—C(O)—$R_{13}$, p) —$NR_{12}$—$OR_{13}$, q) —$SO_2$—$NR_{12}R_{13}$, r) —CN, s) —$CF_3$, t) —C(O)($C_1$–$C_6$)alkyl, u) =O, v) —Z—$SO_2$-phenyl or w) —Z—$SO_2$-het';

aryl' is phenyl, naphthyl or biphenyl;

het' is a 5-, 6- or 7-membered saturated, partially saturated or unsaturated ring containing from one (1) to three (3) heteroatoms independently selected from the group consisting of nitrogen, oxygen and sulfur; and including any bicyclic group in which any of the above heterocyclic rings is fused to a benzene ring or another heterocycle;

provided that:

1) X—$R_1$ is other than hydrogen or methyl;
2) when $R_9$ and $R_{10}$ are substituents on the A-ring, they are other than mono- or di-methoxy;
3) when $R_2$ and $R_3$ are taken together to form =$CHR_{11}$ or =O wherein $R_{11}$ is —O($C_1$–$C_6$)alkyl, then —X—$R_1$ is other than ($C_1$–$C_4$)alkyl;
4) when $R_2$ and $R_3$ taken together are C=O and $R_9$ is hydrogen on the A-ring; or when $R_2$ is hydroxy, $R_3$ is hydrogen and $R_9$ is hydrogen on the A-ring, then $R_{10}$ is other than —O—($C_1$–$C_6$)alkyl or —O—$CH_2$-phenyl at the 2-position of the A-ring;
5) when X—$R_1$ is ($C_1$–$C_4$)alkyl, ($C_2$–$C_4$)alkenyl or ($C_2$–$C_4$)alkynyl, $R_9$ and $R_{10}$ are other than monohydroxy or =O, including the diol form thereof, when taken together; and
6) when X is absent, $R_1$ is other than a moiety containing a heteroatom independently selected from N, O or S directly attached to the juncture of the B-ring and the C-ring. (See U.S. Provisional Patent Application No. 60/132,130)

Each of the glucocorticoid receptor antagonists referenced above and other glucocorticoid receptor antagonists can be used in combination with the compounds of the present invention to treat or prevent diabetes, hyperglycemia, hypercholesterolemia, hypertension, hyperinsulinemia, hyperlipidemia, atherosclerosis, or tissue ischemia.

The compounds of the present invention can also be used in combination with sorbitol dehydrogenase inhibitors. Sorbitol dehydrogenase inhibitors lower fructose levels and have been used to treat or prevent diabetic complications such as neuropathy, retinopathy, nephropathy, cardiomyopathy, microangiopathy, and macroangiopathy. U.S. Pat. Nos. 5,728,704 and 5,866,578 disclose compounds and a method for treating or preventing diabetic complications by inhibiting the enzyme sorbitol dehydrogenase.

Each of the sorbitol dehydrogenase inhibitors referenced above and other sorbitol dehydrogenase inhibitors can be used in combination with the compounds of the present invention to treat diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, or tissue ischemia.

The compounds of the present invention can also be used in combination with sodium-hydrogen exchanger type 1 (NHE-1) inhibitors. NHE-1 inhibitors can be used to reduce tissue damage resulting from ischemia. Of great concern is tissue damage that occurs as a result of ischemia in cardiac, brain, liver, kidney, lung, gut, skeletal muscle, spleen, pancreas, nerve, spinal cord, retina tissue, the vasculature, or intestinal tissue. NHE-1 inhibitors can also be administered to prevent perioperative myocardial ischemic injury.

Examples of NHE-1 inhibitors include a compound having the Formula Ic

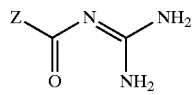

Formula Ic a prodrug thereof or a pharmaceutically acceptable salt of said compound or of said prodrug, wherein Z is carbon connected and is a five-membered, diaza, diunsaturated ring having two contiguous nitrogens, said ring optionally mono-, di-, or tri-substituted with up to three substituents independently selected from $R^1$, $R^2$ and $R^3$; or Z is carbon connected and is a five-membered, triaza, diunsaturated ring, said ring optionally mono- or di-substituted with up to two substituents independently selected from $R^4$ and $R^5$;

wherein $R^1$, $R^2$, $R^3$, $R^4$ and $R^5$ are each independently hydrogen, hydroxy($C_1$–$C_4$)alkyl, ($C_1$–$C_4$)alkyl, ($C_1$–$C_4$)alkylthio, ($C_3$–$C_4$)cycloalkyl, ($C_3$–$C_7$)cycloalkyl($C_1$–$C_4$)alkyl, ($C_1$–$C_4$)alkoxy, ($C_1$–$C_4$)alkoxy($C_1$–$C_4$)alkyl, mono-N- or di-N,N-($C_1$–$C_4$)alkylcarbamoyl, M or M($C_1$–$C_4$)alkyl, any of said previous ($C_1$–$C_4$)alkyl moieties optionally having from one to nine fluorines; said ($C_1$–$C_4$)alkyl or ($C_3$–$C_4$)cycloalkyl optionally mono-or di-substituted independently with hydroxy, ($C_1$–$C_4$)alkoxy, ($C_1$–$C_4$)alkylthio, ($C_1$–$C_4$)alkylsulfinyl, ($C_1$–$C_4$)alkylsulfonyl, ($C_1$–$C_4$)alkyl, mono-N- or di-N,N-($C_1$–$C_4$)alkylcarbamoyl or mono-N- or di-N,N-($C_1$–$C_4$)alkylaminosulfonyl; and said ($C_3$–$C_4$)cycloalkyl optionally having from one to seven fluorines;

wherein M is a partially saturated, fully saturated or fully unsaturated five to eight membered ring optionally having one to three heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

said M is optionally substituted, on one ring if the moiety is monocyclic, or one or both rings if the moiety is bicyclic, on carbon or nitrogen with up to three substituents independently selected from $R^6$, $R^7$ and $R^8$, wherein one of $R^6$, $R^7$ and $R^8$ is optionally a partially saturated, fully saturated, or fully unsaturated three to seven membered ring optionally having one to three heteroatoms selected independently from oxygen, sulfur and nitrogen optionally substituted with $(C_1-C_4)$ alkyl and additionally $R^6$, $R^7$ and $R^8$ are optionally hydroxy, nitro, halo, $(C_1-C_4)$alkoxy, $(C_1-C_4)$alkoxycarbonyl, $(C_1-C_4)$alkyl, formyl, $(C_1-C_4)$alkanoyl, $(C_1-C_4)$alkanoyloxy, $(C_1-C_4)$alkanoylamino, $(C_1-C_4)$alkoxycarbonylamino, sulfonamido, $(C_1-C_4)$alkylsulfonamido, amino, mono-N- or di-N,N-$(C_1-C_4)$alkylamino, carbamoyl, mono-N- or di-N,N-$(C_1-C_4)$alkylcarbamoyl, cyano, thiol, $(C_1-C_4)$alkylthio, $(C_1-C_4)$alkylsulfinyl, $(C_1-C_4)$alkylsulfonyl, mono-N- or di-N,N-$(C_1-C_4)$alkylaminosulfonyl, $(C_2-C_4)$alkenyl, $(C_2-C_4)$alkynyl or $(C_5-C_7)$cycloalkenyl, wherein said $(C_1-C_4)$alkoxy, $(C_1-C_4)$alkyl, $(C_1-C_7)$alkanoyl, $(C_1-C_4)$alkylthio, mono-N- or di-N,N-$(C_1-C_4)$alkylamino or $(C_3-C_7)$cycloalkyl $R^6$, $R^7$ and $R^8$ substituents are optionally mono- substituted independently with hydroxy, $(C_1-C_4)$alkoxycarbonyl, $(C_3-C_7)$cycloalkyl, $(C_1-C_4)$alkanoyl, $(C_1-C_4)$alkanoylamino, $(C_1-C_4)$alkanoyloxy, $(C_1-C_4)$alkoxycarbonylamino, sulfonamido, $(C_1-C_4)$alkylsulfonamido, amino, mono-N- or di-N,N-$(C_1-C_4)$alkylamino, carbamoyl, mono-N- or di-N,N-$(C_1-C_4)$alkylcarbamoyl, cyano, thiol, nitro, $(C_1-C_4)$alkylthio, $(C_1-C_4)$alkylsulfinyl, $(C_1-C_4)$alkylsulfonyl or mono-N- or di-N,N-$(C_1-C_4)$alkylaminosulfonyl or optionally substituted with one to nine fluorines. (See PCT patent application number PCT/IB99/00206)

Each of the NHE-1 inhibitors referenced above and other NHE-1 inhibitors can be used in combination with the compounds of the present invention to treat or prevent diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, or tissue ischemia.

The examples presented below are intended to illustrate particular embodiments of the invention, and are not intended to limit the scope of the specification, including the claims, in any manner. All patents, patent applications, and other references cited in this application are hereby incorporated by reference.

EXAMPLES

Chemical Examples

Exemplary processes for the manufacture of the compounds of the invention are provided below and are illustrated by reaction schemes. These processes may be carried out in sequential or convergent synthetic routes. Purification procedures include crystallization and normal phase or reverse phase chromatography.

As a general note, the preparation of the compounds described herein may require protection of remote functionality (e.g., primary amine, secondary amine, carboxyl). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene and P. G. M. Wuts, *Protective Groups in Organic Synthesis*, John Wiley & Sons, New York, 1991.

The following abbreviations are used herein.

| | |
|---|---|
| Et | ethyl |
| DMF | dimethylformamide |
| BOC | tert-butyloxycarbonyl |
| CBz | benzyloxycarbonyl |
| Ph | phenyl |
| h | hours |
| d | days |
| min | minutes |
| equiv | equivalent(s) |
| DMSO | dimethlysulfoxide |
| dec | decomposes |
| mp | melting point |
| CIMS | chemical ionization mass spectrometry |

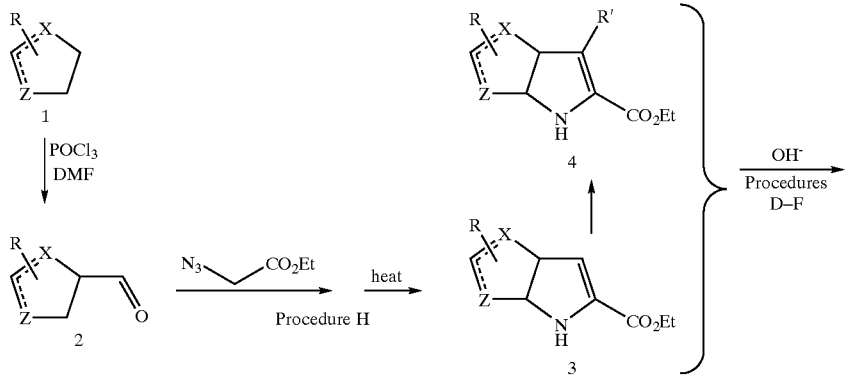

Scheme I

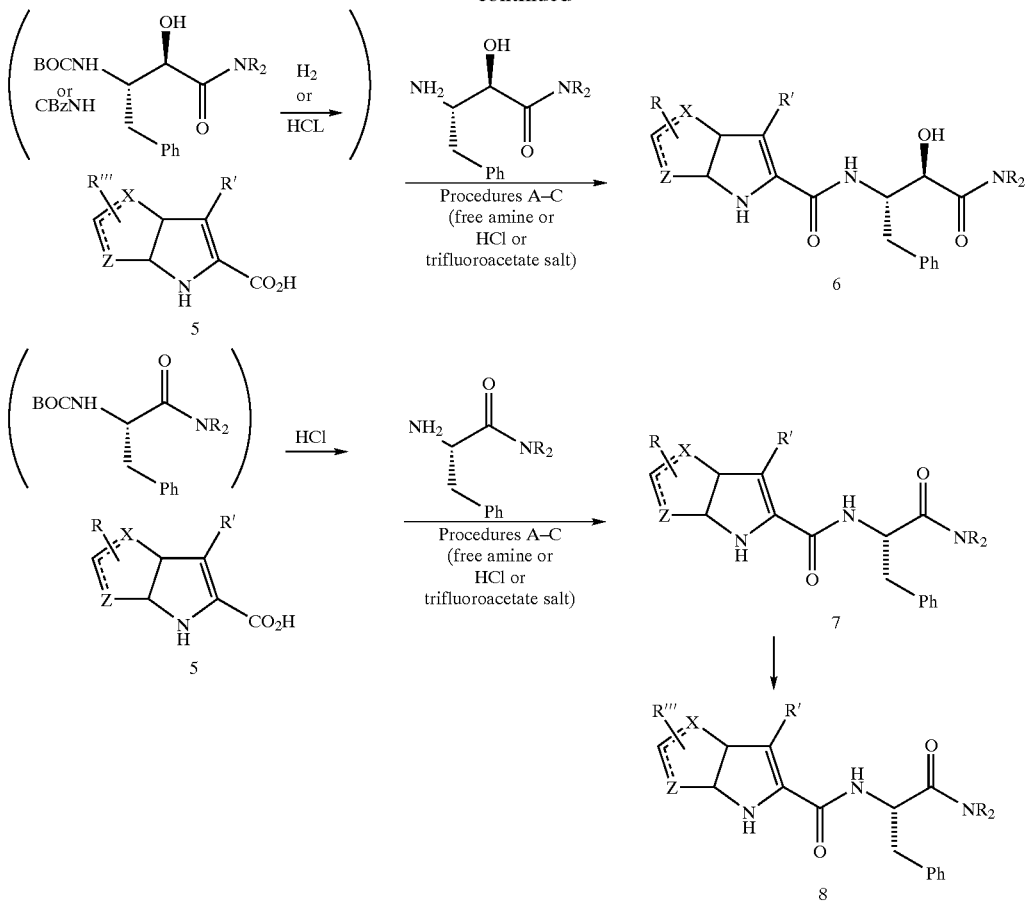
Scheme II
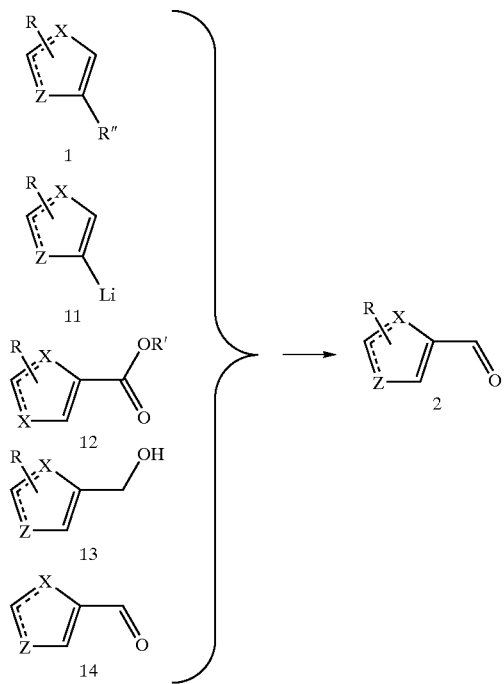
Scheme III
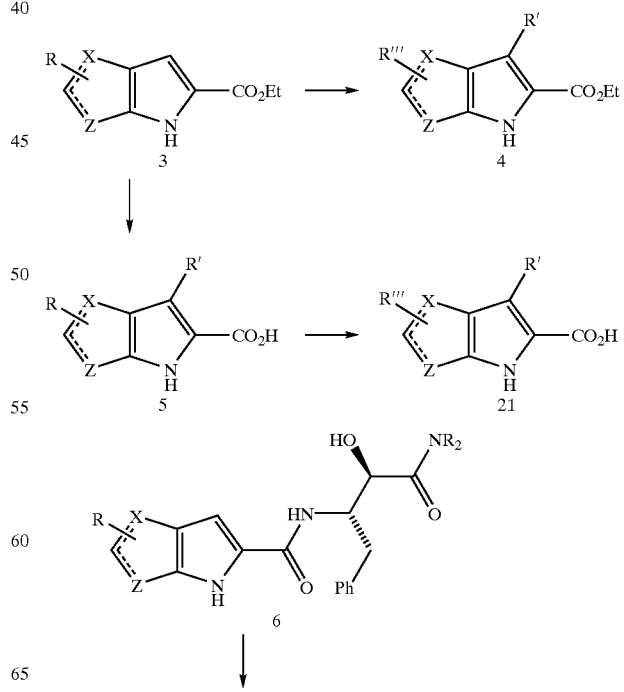

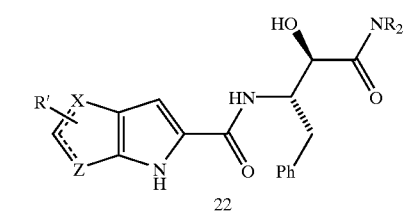
22
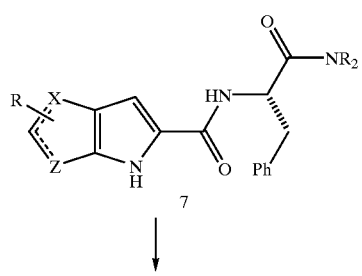
7
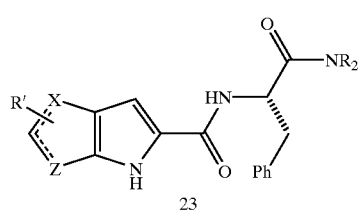
23
Scheme IV
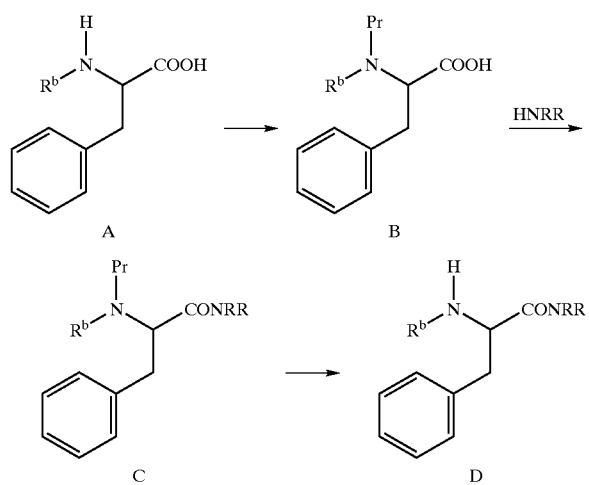
Scheme V
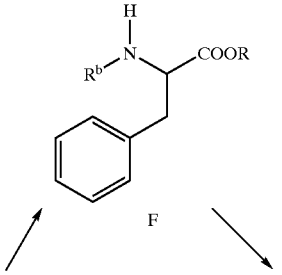
F
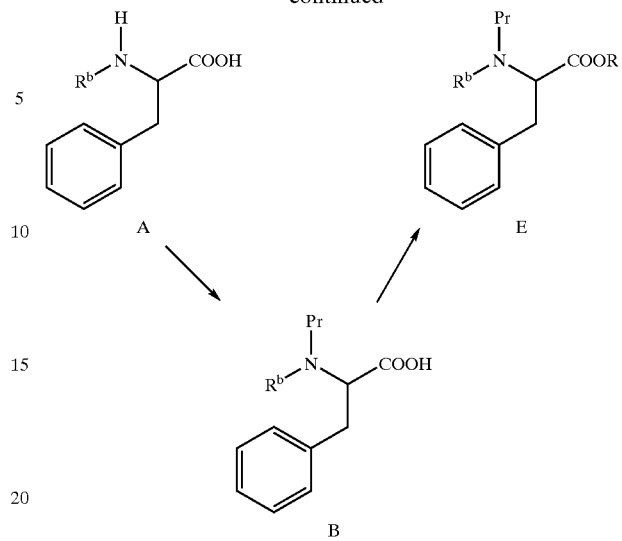
Scheme VI
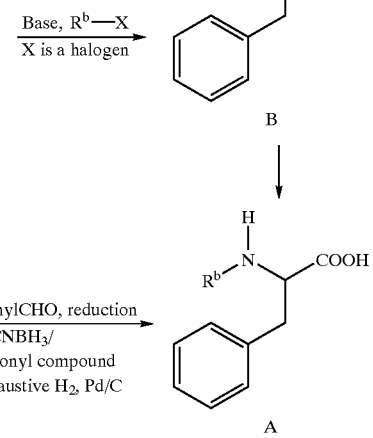
Scheme VII
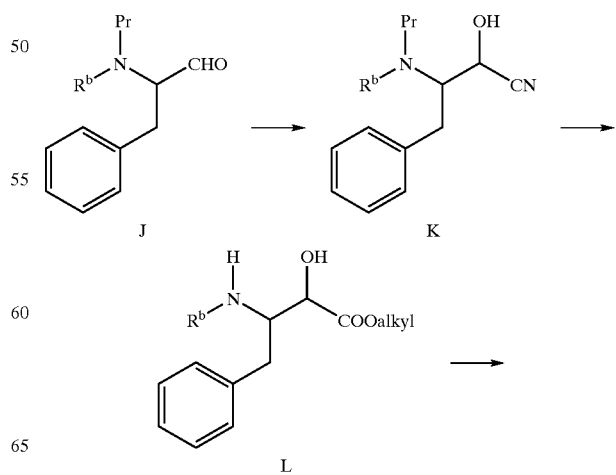

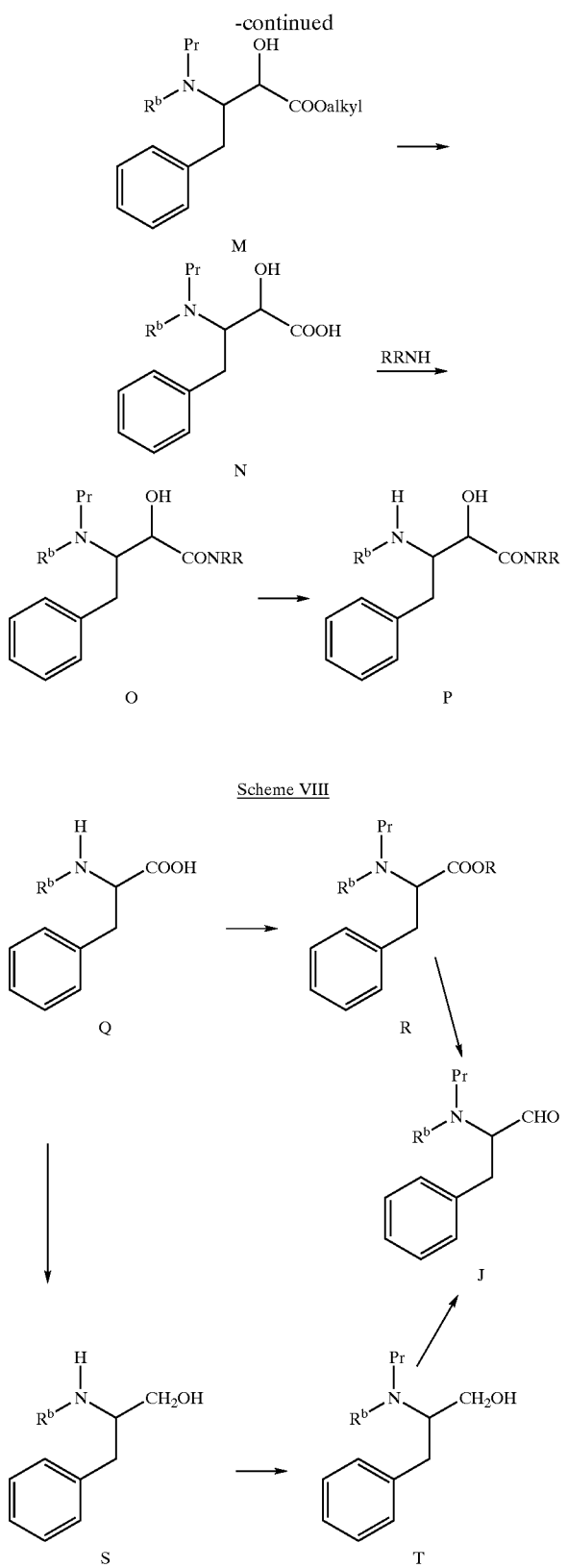

Scheme VIII an azido-acetic acid alkyl ester with an aldehyde of Formula 2 in an alcoholic solvent in the presence of an alkoxide. The alcohol and alkoxide preferred are those derived from the alkyl ester to avoid transesterification problems. The reaction is performed at a temperature of about −20° C. to about 25° C. for about 1–24 hours, generally employing 3–8 equivalents of the alkoxide and an equimolar quantity of the azido-acetic acid alkyl ester. The resultant azides are then heated at reflux in an inert solvent such as xylenes to afford the heterocyclopyrrole esters of Formula 3. An example of a suitable preparation is shown by Procedure H below.

The aldehydes of Formula 2 can be made by conventional methods known to those skilled in the art, or methods for their preparation can readily be determined from the literature (See, for example, Ortiz, J. A. et al., *Eur. J. Med. Chem.*, 23: 477–482 (1988)). With regard to Scheme II, exemplary preparations include Villsmeyer-Haack formylation of heterocycles (R'''=H) of Formula 1 (See, O. Meth-Cohn and S. P. Stanforth in *Comprehensive Organic Synthesis: Selectivity, Strategy & Efficiency in Modem Organic Chemistry* Vol. 2, Pergamon, New York, 1991, C. H. Heathcock, Ed., p 777), metal-halogen exchange of bromo- or iodoheterocycles (R'''=Br, I) of Formula 1 or lithiation of heterocycles of Formula 1 (R'''=H) followed by treatment of aryl lithiums of Formula 11 with a formylating agent such as dimethylformamide (Ortiz, J. A. et al., *Eur. J. Med. Chem.*, 23: 477–482 (1988)) or N-methyl formanilide. (See, D. Comins & S. P. Joseph in *Encyclopedia of Reagents for Organic Synthesis* Vol. 5, Wiley, New York, 1995, L. A. Paquette, Ed., p 3503), reduction of heterocyclic esters of Formula 12 (R=alkyl) or acids (R=H) to Formula 13 alcohols or aldehydes of Formula 2 (Nicolaou, K. C. et al., *Angew. Chem. Int. Ed. Engl.*, 36: 166–7 (1997)) with reducing agents (*Comprehensive Organic Synthesis: Selectivity, Strategy & Efficiency in Modern Organic Chemistry* Vol 8, I. Fleming, Ed., Pergamon, 1991, New York) such as lithium aluminum hydride, diisobutylaluminum hydride, or borane and subsequent oxidation of alcohols of Formula 13 to aldehydes of Formula 2 using oxidizing agents (*Comprehensive Organic Synthesis: Selectivity, Strategy & Efficiency in Modem Organic Chemistry* Vol 7, S. V. Ley, Ed., Pergamon, 1991, New York) such as pyridinium chlorochromate, manganese dioxide, Swern reagent, and barium oxide, or halogenation of the aldehydes of Formula 14 using electrophilic halide sources such as N-halosuccinimide (R. M. Kellogg et al., *J. Org. Chem.*, 33: 2902–2909 (1968)), N-fluoropyridinium salts (Umemoto, T. et al., *J. Am. Chem. Soc.*, 112: 8563–75 (1990)), or elemental halogen (Ortiz, J. A. et al., *Eur. J. Med. Chem.*, 23: 477–482 (1988)).

Alternatively, substitution of the heterocyclopyrroles of Formula 3 can be accomplished by analogous conventional methods known to those skilled in the art or substitution methods can readily be determined from the literature. For example, with regard to Scheme III, mono- and bis-halide substitution can be accomplished by treatment with an electrophilic halide source such as the N-halosuccinimide, N-fluoropyridinium salts, or elemental halogen (Gale, W. W. et al., *J. Org. Chem.*, 29: 2160–2165 (1964)) to produce heterocyclopyrroles of Formula 4 (R',R'''=H and/or halide). Methyl substitution can be accomplished by Villsmeyer-Haack formylation to aldehydes of Formula 4 (R'''=CHO) followed by complete reduction of the formyl group under various reducing conditions such as sodium cyanoborohydride in the presence of zinc iodide in dichloroethane (C. K. Lau et. al., *J. Org. Chem.*, 51: 3038–3043 (1964)). Methyl and other alkyl substitution can also be accomplished by The bicyclic pyrrolyl acids of Formula 5 can be made by several synthetic methods. With regard to Scheme I, a preferred method (Hemetsberger, H. et al., *Monatshefte fur Chemie*, 103: 194–204 (1972)), begins with condensation of coupling Formula 3 bromo- or iodoheterocyclopyrroles (R=Br, I) with alkyl metals such as alkyl copper reagents (Corey, E. J. et al., *J. Am. Chem. Soc.* 89: 3911–12 (1967)). Alkenes and alkynes, in the presence of copper salts such as copper iodide (J. M. Tour et al., *J. Org. Chem.* 61: 6906–6921 (1996); G. M. Whitesides et al., *J. Org. Chem.*, 53: 2489–2496 (1988)), and alkenyl and alkynyl stannanes (Stille, J. K., *Angew. Chem. Int. Ed. Engl.*, 25: 508–524 (1986)) can also be coupled to the bromo- or iodoheterocyclopyrroles of Formula 3 (R=Br, I) in the presence of a catalyst such as palladium. Palladium catalysts include but are not limited to palladium chloride, dichlorobis(triphenylphosphine)palladium (II), tetrakis(triphenylphosphine)palladium (0), and palladium acetate. Other exemplary conditions useful for forming carbon bonds to aromatic rings are described by K. Tamao, D. W. Knight, and K. Sonogashira in *Comprehensive Organic Synthesis: Selectivity, Strategy & Efficiency in Modern Organic Chemistry* Vol 3 (Pergamon, New York, 1991, G. Pattenden, Ed., pp 435–551). Condensation of hydroxylamine with formylated esters of Formula 4 (R'''=CHO) or acids of Formula 5 (R=CHO) can either directly (Ford, R. E. et al., *J. Med. Chem.*, 29, 538–549 (1986)) or after a second dehydration step (Malicorne, G. et al., *Eur. J. Med. Chem. Chim. Ther.* 26: 3–11 (1991) afford nitrites. Alternatively, nitrile substitution can be accomplished by coupling cuprous cyanide to the bromo- or iodoheterocyclopyrroles of Formula 3 (R=Br, I) in dimethylformamide (Klemm, L. H. et al., *J. Heterocyclic Chem.*, 21: 785–9 (1984)). Other exemplary conditions useful for forming nitriles are described by R. Grashey in *Comprehensive Organic Synthesis: Selectivity, Strategy & Efficiency in Modern Organic Chemistry* Vol 6 (Pergamon, New York, 1991, E. Winterfeldt, Ed., p 225). An example of a suitable nitrile preparation is Procedure G below.

Alternatively the aformentioned methods of substituting the heterocyclopyrroles of Formula 3 can also be applied to the amides of Formulas 6 and 7.

The coupling of an acid of Formula 5 (Scheme I) with an amine of Formula A (Scheme IV) or P (Scheme VII) to make a compound of the present invention can be accomplished in several ways, which are analogous to those well known to those skilled in the art.

In a typical coupling procedure, the acid and amine are combined with a suitable coupling agent. A suitable coupling agent is an agent that transforms the carboxylic acid group into a reactive species such that an amide linkage is formed between the carboxylic acid and the amine.

The coupling agent can provide for the coupling in a one pot process or several steps may be required to achieve the coupling. Examples of suitable coupling agents include 1-(3-dimethylaminopropyl)-3-ethylcarbodiimide hydrochloride-hydroxybenzotriazole (DEC/HBT), carbonyldiimidazole, dicyclohexylcarbodiimide/hydroxybenzotriazole, 2-ethoxy-1-ethoxycarbonyl-1,2-dihydroquinoline (EEDQ), carbonyldiimidazole/HBT, propanephosphonic anhydride (propanephosphonic acid anhydride, PAA) and diethylphosphorylcyanide.

The coupling reaction is generally performed in an inert solvent, preferably an aprotic solvent at a temperature of about −20° C. to about 50° C. for about 1 to about 48 hours, optionally in the presence of a tertiary amine such as triethylamine. Suitable solvents include acetonitrile, dichloromethane, ethyl acetate, dimethylformamide and chloroform, or mixtures thereof.

In an example of a multistep coupling process, the carboxylic acid group is reacted with the coupling agent to form an activated intermediate, which can be isolated in the first step of the process. In a second step, the activated intermediate is then reacted with the amine to form the amide. Examples of coupling agents that convert an acid to an activated intermediate include thionyl chloride, oxalyl chloride, which form acid chlorides, cyanuric fluoride, which forms acid flourides, or an alkyl chloroformate such as isobutyl or isopropenyl chloroformate (with a tertiary amine base), which forms a mixed anhydride of the carboxylic acid. If the coupling agent is oxalyl chloride, it is advantageous to employ a small amount of dimethylformamide as a cosolvent with another solvent such as dichloromethane to catalyze the formation of the acid chloride. The acid chloride may be coupled with the amine in an appropriate solvent and a suitable base. Acceptable solvent/base combinations include dichloromethane, dimethylforamide or acetonitirile, or mixture thereof in the presence of a tertiary amine base such as triethylamine. Other appropriate solvent/base combinations include water or a $C_1$–$C_5$ alcohol, or mixtures thereof, together with a cosolvent such as dichloromethane, tetrahydrofuran or dioxane, and a base such as sodium or potassium carbonate, sodium, potassium or lithium hydroxide, or sodium bicarbonate in sufficient quantity to consume the acid liberated in the reaction. Use of a phase transfer catalyst (typically 1 to 10 mole %) such as a quaternary ammonium halide (e.g., tetrabutylammonium bromide or methyl trioctylammonium chloride) is advantageous when a mixture of only partially miscible cosolvents is employed (e.g. dichloromethane-water or dichloromethane-methanol). Use of these coupling agents and appropriate selection of solvents and temperatures are known to those skilled in the art and can be readily determined from the literature. These and other exemplary conditions useful for coupling carboxylic acids with amines are described in Houben-Weyl, Vol. XV, part II, E. Wunsch, Ed., G. Thieme Verlag, 1974, Stuttgart, and M. Bodansky, *Principles of Peptide Synthesis,* Springer-Verlag Berlin 1984, and *The Peptides: Analysis, Synthesis and Biology* (ed. E. Gross and J. Meienhofer), Vols 1–5 (Academic Press, NY 1979–1983).

The amines that are reacted with the carboxylic acid function group to make an amide of the present invention can be synthesized in a number of ways. With regard to Scheme IV, an alpha amino acid of Formula A can be protected on the amine nitrogen with an appropriate protecting group (Pr) to form a protected amino acid of Formula B. One skilled in the art can readily select an appropriate amine protecting group. For example, two common protecting groups are BOC, which is introduced by treating the amino acid with di-tert-butyldicarbonate, preferably in a protic solvent or a solvent mixture at high pH, and CBZ, which is introduced by treating the amino acid with benzylchloroformate, preferably in a protic solvent or a solvent mixture, and a base. The amine protected amino acid compound of Formula B is then coupled with an appropriate amine of the formula HNRR (where the R groups are consistent with the compounds of the present invention) in a procedure analogous to the coupling reaction set forth above to form a protected amide compound of Formula C. The protected amide of Formula C can then be deprotected to form an amide of Formula D. If the protecting group is BOC, the deprotection is typically done by treating the protected compound with an acid in an aprotic solvent. Suitable acids include HCl, $CH_3SO_3H$ and trifluoroacetic acid.

It may also be desired to make esters of the compounds of Formula A or B. With regard to Scheme V, the esters of compound A and B can be made by reacting the compound with an appropriate alcohol and an acid catalyst such as concentrated sulfuric acid or by treatment with an alkyl halide such as methyl idodide and a base such as potassium carbonate. Compounds of Formula E can also be made by protecting a compound of Formula A, and then forming the ester. Alternatively, compounds of Formula E can be made starting with a compound of Formula A, forming an ester, and then protecting the amine group. Analogous procedures for the formation and cleavage of esters and the protection of amine groups are well known to those skilled in the art.

According to reaction Scheme VI, the compounds of Formula A when $R^b$ is not hydrogen can be prepared as follows. The Formula B amino acid can be prepared by N-alkylation of a compound of Formula G, which is an amine protected alpha amino acid. N-alkylation is well known in the art and can be accomplished using an appropriate alkylating agent and a suitable base. Specific procedures for alkylation are described in Benoiton, *Can. J. Chem.*, 55: 906–910 (1985), and Hansen, *J. Org. Chem.*, 50: 945–950 (1977). For example, when $R^b$ is methyl, and Pr is BOC, sodium hydride and methyl iodide in tetrahydrofuran can be used. Deprotection of the compound of Formula B results in a compound of Formula A.

Alternatively, a compound of Formula H can be N-alkylated by a three step sequence involving reductive benzylation, such as with benzaldehyde followed by Pd/C-catalyzed hydrogenation to give the mono-N-benzyl derivative, and reductive amination with an appropriate carbonyl compound, for example formaldehyde and sodium cyanoborohydride to introduce $R^b$ as methyl, to give the N-benzyl, substituted amino acid. The N-benzyl protecting group is conveniently removed, for example, by hydrogenation with an appropriate catalyst, to yield a compound of Formula A. Specific conditions for the three step alkylation procedure are described by Reinhold et al., *J. Med. Chem.*, 11: 258–260 (1968).

While many of the alpha amino acid starting materials are known, they can be synthesized by a number of procedures that are well known in the art. For example, the Strecker synthesis or variations thereof can be used. Accordingly, an aldehyde, sodium or potassium cyanide and ammonium chloride react to form an aminonitrile. It is noted that the aldehyde selected is determined by the desired amino acid. The aminonitrile is then hydrolyzed with a mineral acid to form the desired amino acid. Alternatively, the Bucherer-Berg method may be used where a hydantoin is formed by heating an aldehyde with ammonium carbonate and potassium cyanide followed by hydrolysis, for example, with barium hydroxide in refluxing dioxane, with acid or base to form the desired compounds.

Suitable methods for the synthesis and/or resolution of compounds of Formula H (Scheme VI) (alpha amino acids) are found in reviews by Duthaler, *Tetrahedron*, 50: 1539–1650 (1994), or by Williams, Synthesis of Optically Active Amino Acids, Pergamon, Oxford, U.K. 1989. Another method is shown in Corey and Link, *J. Am. Chem. Soc.*, 114:1906–1908 (1992).

The synthesis of the compounds of the present invention where Y is

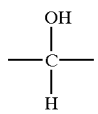

is accomplished by the coupling of an amide compound of Formula P (Scheme VII) with a bicylic pyrrolyl carboxylic acid of Formula 5. The procedure for the coupling can be carried out as described above. The synthesis of the amides of Formula P is illustrated by Scheme VII. To begin, a nitrogen protected amino aldehyde of Formula J is treated with potassium or sodium cyanide in aqueous solution with a cosolvent such as dioxane or ethyl acetate at a temperature of about 0° C. to about 50° C. to provide a compound of Formula K, which is cyanohydrin. The cyanohydrin of Formula K is then reacted with an alcohol such as methanol and a strong acid catalyst such as HCl at a temperature of about 0° C. to about 50° C., followed by the addition of water, if necessary. The protecting group is then removed, if still present, by an appropriate deprotection method yielding a compound of Formula L. For example, if the protecting group is BOC, the Formula L compound is directly formed from the Formula K compound, and addition of water is not necessary. The Formula L compound can be protected on the nitrogen to form a compound of Formula M followed by hydrolysis of the ester with aqueous alkali at a temperature of about 0° C. to about 50° C. in a reaction-inert solvent resulting in the corresponding hydroxy acid of Formula N. The hydroxy acid of formula N is coupled to a suitable amine to form the protected amino amide of Formula O, which is then deptrotected to form a compound of Formula P. An analogous example of the conversion of a Formula K compound to the corresponding Formula L compound is provided in PCT publication WO/9325574, Example 1a. Other analogous examples where a cyanohydrin is converted to a Formula M compound can be found in U.S. Pat. No. 4,814,342 and EPO publication 0438233.

It may be desirable to have a certain stereochemistry at the alpha and beta positions of the compounds of Formula P. (The alpha position is the carbon atom containing the hydroxyl group.) The desired stereochemistry can be obtained by the use of a single stereoisomeric aldehyde of Formula J. The Formula K cyanohydrin can be prepared from the stereochemically pure aldehyde by treatment with sodium or potassium cyanide as described above while maintaining the stereochemistry of the chiral carbon of the aldehyde, resulting in a mixture of stereoisomers, which can be separated, as is well known to those skilled in the art by crystallization. See, for example, *Biochemistry*, 31: 8125–8141 (1992). Alternatively, isomer separation can be effected by chromatography or recrystallization techniques after conversion of a compound of Formula K to a compound of Formula L, M, N, O, or P by the procedures described herein and analogous to those well known in the art.

With reference to Scheme VIII, the aminoaldehydes of Formula J can be made from the corresponding alpha amino acid of Formula Q. In one method, the alpha amino acid of Formula Q is protected on nitrogen and esterified to form a compound of Formula R. The compound of Formula R is reduced, for example, with diisobutylaluminum hydride in hexane or toluene, or a mixture thereof, at a temperature of about −78° C. to about −50° C. followed by quenching with methanol at −78° C. as described in *J. Med. Chem.*, 28:1779–1790 (1985) to form the Formula J aldehyde.

Alternatively, the Formula J aldehydes can be made by oxidation of Formula T alcohols, for example, with pyridine- $SO_3$ at a temperature of about −10° C. to about 40° C. in a reaction-inert solvent, preferably dimethylsulfoxide. The protected amino alcohols of Formula T, if not commercially available, can be made by the protection of aminoalcohols of Formula S. The Formula S aminoalcohols are prepared by the reduction of amino acids of formula Q. The reduction can be accomplished by treating Formula Q amino acids with lithium aluminum hydride according to the procedure described by Dickman et al., *Organic Synthesis;* Wiley: New York, 1990; Collect. Vol. Vil, p. 530. or with sulfuric acid-sodium borohydride by the procedure of Abiko and Masamune, *Tetrahedron Lett.,* 333: 5517–5518 (1992) or with sodium borohydride-iodine according to the procedure of McKennon and Myers, *J. Org. Chem.,* 58: 3568–3571 (1993), where other suitable procedures are also reviewed. The preparation of the alpha amino acid and N-alkylated alpha amino acids has been described above.

In addition, PCT publications WO 9613985, published Dec. 12, 1996, and WO 96/39384, published Dec. 12, 1996, contain further details and exemplifications of the processes of synthesizing aspects of the present compounds. These publications are hereby incorporated by reference.

Equipment and General Procedures

NMR spectra were recorded on a Bruker AM300 or Varian XL-400 spectrometer at about 23° C. at 300 or 400 MHz, respectively, for proton nuclei. Unless otherwise specified, NMR spectral data is reported for a 400 MHz spectrometer. Routine mass spectral data were obtained using a VG/Fisons Instruments Platform II spectrometer operating with an Atmospheric Pressure Chemical Ionization (APCI) source. Melting points are uncorrected and were determined on a Thomas Hoover capillary melting point apparatus. Unless otherwise specified, reagents were used as obtained from commercial sources. The term "concentrated" refers to removal of solvent on a rotary evaporator. Exceptions in the use of the Procedures A–H are noted individually in parentheses, following mention of the procedure.

General Synthetic Procedures

Procedure A (Amide Formation Using 1-Hydroxybenzotriazole Hydrate and 1-(3-Dimethylamino-propyl)-3-ethylcarbodiimide Hydrochloride)

A 0° C. 0.1–0.7 M mixture the primary amine (1 equiv, or a primary amine salt and 1 equiv of triethylamine per equiv HCl), 1 equiv of the specified carboxylic acid, and 1 equiv of 1-hydroxybenzotriazole hydrate (1 equiv relative to the carboxylic acid), in 3:1 dichloromethane:dimethylformamide is treated with 1 equiv 1-(3-dimethylamino-propyl)-3-ethylcarbodiimide hydrochloride. The mixture is allowed to warm to room temperature over several hours, stirred overnight, concentrated to remove the dichloromethane, and partitioned between ethyl acetate and 1–2 N HCl. The aqueous phase is extracted with ethyl acetate. The combined organic phases are washed with saturated aqueous $NaHCO_3$, dried over $MgSO_4$, and concentrated giving crude product which is purified by chromatography on silica gel and/or recrystallization.

Procedure B (Amide Formation Using 1-Hvdroxy-7-azabenzotriazole Hydrate and 1-(3-Dimethylamino-propyl)-3-ethylcarbodiimide Hydrochloride)

A 0° C. 0.1–0.3 M mixture of the primary amine or primary amine salt (1 equiv), 1 equiv of triethylamine, 1 equiv of the specified carboxylic acid, and 1 equiv of 1-hydroxy-7-azabenzotriazole (1 equiv relative to the carboxylic acid), in dimethylformamide is treated with 1 equiv (corresponding in mol ratio to the carboxylic acid) 1-(3-dimethylamino-propyl)-3-ethylcarbodiimide hydrochloride. The mixture is allowed to warm to room temperature over several hours, stirred overnight, and partitioned between ethyl acetate and 1–2 N HCl. The organic phase is washed with saturated aqueous $NaHCO_3$, dried over $MgSO_4$, and concentrated giving crude product which is purified by chromatography on silica gel.

Procedure C (Amide Formation Using 1-Hydroxy-7-azabenzotriazole Hydrate and 1-(3-Dimethylamino-propyl)-3-ethylcarbodiimide Methiodide)

A 0.3 M mixture of the primary amine hydrochloride (1 equiv), 1.2 equiv of triethylamine, 1 equiv of the specified carboxylic acid, and 1.2 equiv of 1-hydroxybenzotriazole hydrate in dimethylformamide is treated with 1.2 equiv 1-(3-dimethylamino-propyl)-3-ethylcarbodiimide methiodide. The mixture is stirred overnight and partitioned between ethyl acetate and 1 N NaOH. The organic phase is washed sequentially with 1 N HCl and water, dried over $MgSO_4$, and concentrated giving crude product.

Procedure D (Hydrolysis of Ethyl Ester with Potassium Hydroxide)

A 0.1–0.8 M suspension of the ethyl ester (1 equiv) and KOH (2 equiv) in water is heated at reflux for 1–7 h, allowed to cool to room temperature, stirred overnight, and extracted with ethyl acetate. The aqueous phase is acidified with 2 N HCl and extracted with ethyl acetate. The combined organic phases are dried over $MgSO_4$, and concentrated giving crude product which is purified by chromatography and/or washing with solvent.

Procedure E (Hydrolysis of Ethyl Ester with Sodium Hydroxide)

A 0.1–0.8 M suspension of the ethyl ester (1 equiv) and 2 N NaOH (10 equiv) in methanol is heated at 65° C. for 2 h, allowed to cool to room temperature, concentrated to remove the methanol, diluted with water, and extracted with ethyl acetate. The aqueous phase is acidified with 2 N HCl and extracted with ethyl acetate. The combined organic phases are dried over $MgSO_4$, and concentrated giving crude product which is purified by recrystallization.

Procedure F (Hydrolysis of Ethyl Ester with Lithium Hydroxide)

A 0.1–0.3 M solution of the ethyl ester (1 equiv) and $LiOH-H_2O$ (4–6 equiv) in 3:2:1 tetrahydrofuran:methanol:water is heated at 60–65° C. overnight, allowed to cool to room temperature, concentrated to remove the tetrahydrofuran and methanol, and acidified with 1–2 N HCl. The resultant precipitate is filtered, washed with water, and dried in vacuo giving product.

Procedure G (Nitrile Formation with Hydroxylamine Hydrochloride)

A 0.1–0.2 M mixture of the aldehyde (1 equiv) and hydroxylamine hydrochloride (2.2–4 equiv) in dimethylformamide is heated at 125° C. overnight, allowed to cool to room temperature, and partitioned between ethyl acetate and water. The aqueous phase is extracted with ethyl acetate. The combined organic phases are washed with water, dried over MgSO$_4$, and concentrated giving crude product which is purified by chromatography on silica gel.

Procedure H (Annulation with Azido-acetic Acid Ethyl Ester)

A 0° C. 0.6–1.2 M solution of sodium (3–4 equiv) in ethanol is treated with a mixture of the aldehyde (1 equiv) and azido-acetic acid ethyl ester (1 equiv relative to sodium) dropwise such that the reaction temperature was maintained at 5–10° C. The reaction mixture is stirred for 1–2 h, quenched with cold saturated aqueous NH$_4$Cl, and extracted with ether. The combined organic phases are dried over MgSO$_4$ and concentrated. The residue is purified by chromatography on silica gel. A 0.1–0.2 M solution of the resultant acrylate in xylenes is heated at reflux for 20–60 min and allowed to cool to room temperature. The reaction solution is either cooled further to induce crystallization of the product or concentrated giving crude product which is purified by washing with hexanes and/or chromatography on silica gel.

Example 1

6H-Thieno[2,3-b]pyrrole-5-carboxylic acid [(1S)-benzyl-3-((3R,4S)-dihydroxy-pyrrolidin-1-yl)-(2R)-hydroxy-3-oxo-propyl]-amide 6H-Thieno[2,3-b]pyrrole-5-carboxylic acid (Soth, S. et al., *Bull. Soc. Chim. Fr.*, 2511–2515 (1975)) and (3S)-amino-1-((3R,4S)-dihydroxy-pyrrolidin-1-yl)-(2R)-hydroxy-4-phenyl-butan-1-one were coupled according to Procedure A (4-(dimethylamino)pyridine (0.1 equiv) also added to the reaction mixture).

mp 137–145° C.; CIMS m/e 430.2 (MH$^+$). $^1$H NMR (DMSO-d$_6$) δ11.67 (br s, 1H), 7.74 (d, J=8.9 Hz, 1H), 7.21 (m, 4H), 7.11 (m, 1H), 6.96 (s, 3H), 5.03 (dd, J=2.9, 7.5 Hz, 0.5H), 4.93 (m, 1H), 4.87 (m, 0.5H), 4.80 (dd, J=2.9, 7.5 Hz, 0.5H), 4.74 (br s, 0.5H), 4.40 (br s, 1H), 4.19 (m, 1H), 4.06 (dq, J=3.2, 5.3 Hz, 0.5H), 3.99–3.87 (m, 1.5H), 3.54 (m, 1H), 3.38 (m, 0.5H), 3.25–3.06 (m, 2.5H), 2.94–2.81 (m, 2H).

Example 1a

[(1S)-Benzyl-3-((3R,4S)-dihydroxy-pyrrolidin-1-yl)-(2R)-hydroxy-3-oxo-propyl]-carbamic acid benzyl ester (2R,3S)-3-Benzyloxycarbonylamino-2-hydroxy-4-phenyl-butyric acid (Takita, T. et al., *J. Med. Chem.*, 20: 510–515 (1977)) and pyrrolidine-(3R,4S)-diol hydrochloride were coupled according to Procedure A (dimethylformamide reaction solvent concentrated to ½ volume before work-up).

CIMS m/e 415.2 (MH$^+$). $^1$H NMR (DMSO-d$_6$) δ7.28–7.15 (m, 10H), 7.07–7.01 (m, 1H), 4.94–4.75 (m, 4.5H), 4.65 (d, J=7.7 Hz, 0.5H), 4.09–3.88 (m, 4H), 3.51–3.38 (m, 1H), 3.27–3.07 (m, 3H), 2.83–2.63 (m, 2H).

Example 1b (3S)-Amino-1-((3R,4S)-dihydroxy-pyrrolidin-1-yl)-(2R)-hydroxy-4-phenyl-butan-1-one According to a procedure by Takita, T. et al. (*J. Med. Chem.*, 20: 510–515 (1977)) a mixture of [(1S)-benzyl-3-((3R,4S)-dihydroxy-pyrrolidin-1-yl)-(2R)-hydroxy-3-oxo-propyl]-carbamic acid benzyl ester (1.2 g, 2.9 mmol) and 10% palladium on carbon (120 mg) in methanol (20 mL) was shaken under a hydrogen atmosphere (40–45 psi) on a Parr apparatus overnight, filtered through Celite®, and concentrated. The product was obtained as a sticky solid (1.0 g, 100%).

CIMS m/e 281.2 (MH$^+$). 1H NMR (DMSO-d$_6$) δ7.27–7.13 (m, 5H), 4.95–4.80 (m, 3H), 3.93 (br s, 2H), 3.83 (dd, J=3.3, 9.1 Hz, 1H), 3.45–3.05 (m, 6H), 2.99 (dq, J=3.5, 6.3 Hz, 1H), 2.65 (m, 1H), 2.50 (m, 1H).

Example 2

2-Bromo-6H-thieno[2,3-b]pyrrole-5-carboxylic acid [(1S)-benzyl-3-((3R,4S)-dihydroxy-pyrrolidin-1-yl)-(2R)-hydroxy-3-oxo-propyl]-amide 2-Bromo-6H-thieno[2,3-b]pyrrole-5-carboxylic acid and (3S)-amino-1-((3R,4S)-dihydroxy-pyrrolidin-1-yl)-(2R)-hydroxy-4-phenyl-butan-1-one were coupled according to Procedure A.

mp 143–145° C.; CIMS m/e 508.0/510.0 (MH$^+$). $^1$H NMR (DMSO-d$_6$) δ11.72 (br s, 1H), 7.84 (d, J=9.1 Hz, 1H), 7.22 (m, 5H), 7.11 (m, 1H), 6.99 (s, 1H), 5.04 (d, J=7.3 Hz, 0.5H), 4.95 (m, 1H), 4.89 (d, J=5.0 Hz, 0.5H), 4.80 (d, J=7.7 Hz, 0.5H), 4.75 (d, J=4.4 Hz, 0.5H), 4.40 (m, 1H), 4.19 (m, 1H), 4.00–3.85 (m, 2H), 3.54 (m,1H), 3.39 (dd, J=4.9, 12.6 Hz, 0.5H), 3.22 (m, 1.5H), 3.16–3.06 (m, 1H), 2.94–2.81 (m, 2H).

Example 2a

2-Bromo-6H-thieno[2,3-b]pyrrole-5-carboxylic acid

2-Bromo-6H-thieno[2,3-b]pyrrole-5-carboxylic acid ethyl ester (Eras, J.; Galvez, C.; Garcia, F., *J. Heterocycl. Chem.*, 21: 215–217 (1984)) was hydrolyzed according to Procedure F.

CIMS m/e 244.0/246.0 ((M–H)$^+$). $^1$H NMR (DMSO-d$_6$) δ12.66 (br s, 1H), 12.10 (br s, 1H), 7.22 (s, 1H), 6.87 (d, J=2.1 Hz, 1H).

Example 3

2-Methyl-6H-thieno[2,3-b]pyrrole-5-carboxylic acid [(1S)-benzyl-3-((3R,4S)-dihydroxy-pyrrolidin-1-yl)-(2R)-hydroxy-3-oxo-propyl]-amide 2-Methyl-6H-thieno[2,3-b]pyrrole-5-carboxylic acid and (3S)-amino-1-((3R,4S)-dihydroxy-pyrrolidin-1-yl)-(2R)-hydroxy-4-phenyl-butan-1-one hydrochloride were coupled according to Procedure A (1.5 equiv 1-hydroxybenzotriazole hydrate, 1.1 equiv 1-(3-dimethylamino-propyl)-3-ethylcarbodiimide hydrochloride, 15:1 dichloromethane:dimethylformamide; combined organic phases washed with water prior to saturated aqueous NaHCO$_3$).

mp 154–157° C.; CIMS m/e 442.2 ((M–H)$^+$). $^1$H NMR (DMSO-d$_6$) δ11.58 (m,1H), 7.66 (d, J=8.5 Hz,1H), 7.22–7.10 (m, 5H), 6.86 (s, 1H), 6.64 (s, 1H), 5.03–4.73 (m, 3H), 4.38 (br s, 1H), 4.18 (m, 1H), 3.98–3.88 (m, 2H), 3.53 (m, 1H), 3.39–3.05 (m, 3H), 2.90–2.83 (m, 2H), 2.38 (s, 3H).

Example 3a

2-Methyl-6H-thieno[2,3-b]pyrrole-5-carboxylic acid ethyl ester

Using a procedure by C. K. Lau et. al. (*J. Org. Chem.*, 51: 3038–3043 (1986)), a mixture of 2-formyl-6H-thieno[2,3- b]pyrrole-5-carboxylic acid ethyl ester (Soth, S. et al., *Bull. Soc. Chim. Fr.*, 2511–2515 (1975); 500 mg, 2.24 mmol), ZnI$_2$ (1.08 g, 3.36 mmol), and NaBH$_3$CN (1.06 g, 16.8 mmol) in dichloroethane (25 mL) was stirred for 7 d and quenched with saturated aqueous NH$_4$Cl (25 mL). The resultant biphasic mixture was stirred for an additional 30 min, extracted with ethyl acetate, dried over Na$_2$SO$_4$, and concentrated. The product was purified by Chromatotron-chromatography (3:2 hexanes:ether) and obtained as a white foam (233 mg, 50%).

mp 107–109° C.; CIMS m/e 208.3 (MH$^+$). $^1$H NMR (CDCl$_3$) δ9.13 (br s, 1H), 6.94 (s, 1H), 6.61 (s, 1H), 4.33 (q, J=7.1 Hz, 2H), 2.48 (s, 3H), 1.36 (t, J=7.1 Hz, 3H).

Example 3b

2-Methyl-6H-thieno[2,3-b]pyrrole-5-carboxylic acid

2-Methyl-6H-thieno[2,3-b]pyrrole-5-carboxylic acid ethyl ester was hydrolyzed according to Procedure E.

mp 180–182° C. dec.; CIMS m/e 180.1 ((M–H)$^+$). $^1$H NMR (DMSO-d$_6$) δ12.36 (s, 1H), 11.93 (s, 1H), 6.77 (s, 1H), 6.66 (s, 1H), 2.40 (s, 3H), 1.36 (t, J=7.1 Hz, 3H).

Example 3c

[(1S)-Benzyl-3-((3R,4S)-dihydroxy-pyrrolidin-1-yl)-(2R)-hydroxy-3-oxo-propyl]-carbamic acid tert-butyl ester (2R,3S)-3-tert-Butoxycarbonylamino-2-hydroxy-4-phenyl-butyric acid and pyrrolidine-(3R,4S)-diol hydrochloride were coupled according to Procedure A (1.05 equiv triethylamine, 1.1 equiv carboxylic acid; 1.5 equiv 1-hydroxybenzotriazole hydrate; 1.1 equiv 1-(3-dimethylamino-propyl)-3-ethylcarbodiimide hydrochloride; after dichloromethane removal, residue partitioned between ethyl acetate and 2 N NaOH; combined organic phases washed sequentially with 2 N HCl and saturated NaCl).

CIMS m/e 381 (MH$^+$).

Example 3d (3S)-Amino-1-((3R,4S)-dihydroxy-pyrrolidin-1-yl)-(2R)-hydroxy-4-phenyl-butan-1-one hydrochloride To a 0° C. solution of [(1S)-benzyl-3-((3R,4S)-dihydroxy-pyrrolidin-1-yl)-(2R)-hydroxy-3-oxo-propyl]-carbamic acid tert-butyl ester (1.1 g, 2.9 mmol) in methanol (4 mL) was added 4 N HCl in dioxane (7.2 mL, 28.9 mmol). The solution was allowed to slowly warm to room temperature and stirred overnight. The reaction mixture was concentrated and the residue was washed with methanol and dried in vacuo. The product was obtained as a white solid (1.03 g, 113%).

CIMS m/e 281.2 (MH$^+$).

Example 4

(±)-2-Methyl-6H-thieno[2,3-b]pyrrole-5-carboxylic acid [1-benzyl-2-((3R,4S)-dihydroxy-pyrrolidin-1-yl)-2-oxo-ethyl]-amide 2-Methyl-6H-thieno[2,3-b]pyrrole-5-carboxylic acid and (±)-2-amino-1-((3R,4S)-dihydroxy-pyrrolidin-1-yl)-3-phenyl-propan-1-one hydrochloride were coupled according to Procedure A (1.5 equiv 1-hydroxybenzotriazole hydrate, 1.1 equiv 1-(3-dimethylamino-propyl)-3-ethylcarbodiimide hydrochloride, 15:1 dichloromethane:dimethylformamide; combined organic phases washed with water prior to saturated aqueous NaHCO$_3$).

mp 134–136° C.; CIMS m/e 412.0 ((M–H)$^+$). $^1$H NMR (DMSO-d$_6$) δ11.60 (s, 1H), 8.37 (m, 1H), 7.27–6.98 (m, 6H), 6.65 (s, 1H), 4.99–4.73 (m, 3H), 4.05–3.82 (m, 2.5H), 3.40–2.87 (m, 5.5H), 2.38 (s, 3H).

Example 4a (±)-[1-Benzyl-2-((3R,4S)-dihydroxy-pyrrolidin-1-yl)-2-oxo-ethyl]-carbamic acid tert-butyl ester Boc-DL-Phenylalanine and pyrrolidine-(3R,4S)-diol hydrochloride were coupled according to Procedure A (1.5 equiv 1-hydroxybenzotriazole hydrate, 1.1 equiv 1-(3-dimethylamino-propyl)-3-ethylcarbodiimide hydrochloride, dichloromethane; 3 d reaction time).

CIMS m/e 351.2 (MH$^+$). $^1$H NMR (CDCl$_3$) δ7.28–7.19 (m, 5H), 5.35 (m, 1H), 4.52 (m,1H), 4.14–3.99 (m, 1.5H), 3.78–3.63 (m, 1.5H), 3.46–3.34 (m, 2H), 3.00–2.65 (m, 3H), 1.40 (s, 9H).

Example 4b (±)-2-Amino-1-((3R,4S)-dihydroxy-pyrrolidin-1-yl)-3-phenyl-propan-1-one hydrochloride To a 0° C. solution of (±)-[1-benzyl-2-((3R,4S)-dihydroxy-pyrrolidin-1-yl)-2-oxo-ethyl]-carbamic acid tert-butyl ester (6.5 g, 20 mmol) in methanol (8 mL) was added 4 N HCl in dioxane (50 mL, 200 mmol). The solution was allowed to slowly warm to room temperature and stirred overnight. The resultant white reaction mixture was diluted with ether and the precipitate was filtered, washed with ether, and dried in vacuo. The product was obtained as a white solid (5 g, 87%).

CIMS m/e 251.2 (MH$^+$). $^1$H NMR (300 MHz, DMSO-d$_6$) δ8.28 (br s, 3H), 7.38–7.21 (m, 5H), 5.11–4.93 (m, 2H), 4.34–4.22 (m, 1H), 3.96 (m, 1H), 3.81–3.70 (m, 1H), 3.89 (m, 0.5H), 3.47 (m, 0.5H), 3.33–2.85 (m, 4H), 2.63 (m, 1H).

Example 5

2-Bromo-6H-thieno[2,3-b]pyrrole-5-carboxylic acid [(1S)-benzyl-2-((3R,4S)-dihydroxy-pyrrolidin-1-yl)-2-oxo-ethyl]-amide 2-Bromo-6H-thieno[2,3-b]pyrrole-5-carboxylic acid and (2S)-amino-1-((3R,4S)-dihydroxy-pyrrolidin-1-yl)-3-phenyl-propan-1-one hydrochloride were coupled according to Procedure A (1.5 equiv 1-hydroxybenzotriazole hydrate, 1.1 equiv 1-(3-dimethylamino-propyl)-3-ethylcarbodiimide hydrochloride, 25:1 dichloromethane:dimethylformamide; combined organic phases washed with water prior to saturated aqueous NaHCO$_3$).

mp 140–142° C.; CIMS m/e 477.9/479.9 (MH$^+$). $^1$H NMR (DMSO-d$_6$) δ11.73 (s, 1H), 8.55 (d, J=8.1 Hz, 1H), 7.26–7.09 (m, 7H), 5.00 (br s, 0.5H), 4.91–4.85 (m, 1.5H), 4.77 (m, 1H), 4.07–3.93 (m, 1.5H), 3.83 (m, 1.5H), 3.41–3.25 (m, 1H), 3.13 (m, 2H), 3.00–2.87 (m, 2H).

Example 5a

[(1S)-Benzyl-2-((3R,4S)-dihydroxy-pyrrolidin-1-yl)-2-oxo-ethyl]-carbamic acid tert-butyl ester Boc-L-Phenylalanine and pyrrolidine-(3R,4S)-diol hydrochloride were coupled according to Procedure A (1.5 equiv 1-hydroxybenzotriazole hydrate, dichloromethane;

reaction mixture diluted with ethyl acetate and washed sequentially with 1 N NaOH, 1 N HCl, and saturated sodium chloride prior to drying).

CIMS m/e 351.2 (MH+). ¹H NMR (DMSO-d₆) δ7.25–7.13 (m, 5H), 7.06 (dd, J=8.4, 13.6 Hz, 1H), 4.98 (d, J=5.4 Hz, 0.5H), 4.91 (d, J=5.0 Hz, 0.5H), 4.84 (m, 1H), 4.25 (dd, J=8.5, 14.3 Hz, 1H), 4.02 (m, 0.5H), 3.94 (m, 0.5H), 3.79 (m, 1H), 3.68 (dd, J=5.9, 10.1 Hz, 0.5H), 3.38 (dd, J=5.3, 12.2 Hz, 0.5H), 3.27–3.10 (m, 3H), 2.83–2.67 (m, 2H), 1.27 (s, 5H), 1.25 (s, 4H).

Example 5b (2S)-Amino-1-((3R,4S)-dihydroxy-pyrrolidin-1-yl)-3-phenyl-propan-1-one hydrochloride To 4 N HCl in dioxane (120 mL, 480 mmol) was added [(1S)-benzyl-2-((3R,4S)-dihydroxy-pyrrolidin-1-yl)-2-oxo-ethyl]-carbamic acid tert-butyl ester (27 g, 77 mmol). The solution was stirred 2.5 h and concentrated. The product was obtained as a white solid (21.5 g, 98%).

CIMS m/e 251.0 (MH+). ¹H NMR (DMSO-d₆) δ8.33 (br s, 3H), 7.32–7.16 (m, 5H), 5.10–4.86 (m, 2H), 4.25–4.13 (m, 1H), 3.93 (m, 1H), 3.73–3.66 (m, 1H), 3.54 (m, 0.5H), 3.46–3.23 (m, 1.5H), 3.18–3.05 (m, 2H), 3.00 (m, 0.5H), 2.91–2.79 (m, 1H), 2.57 (dd, J=5.6, 10.0 Hz, 0.5H).

Example 6

2–Chloro-6H-thieno[2,3-b]pyrrole-5-carboxylic acid [(1S)-benzyl-3-((3R,4S)-dihydroxy-pyrrolidin-1-yl)-(2R)-hydroxy-3-oxo-propyl]-amide 2–Chloro-6H-thieno[2,3-b]pyrrole-5-carboxylic acid and (3S)-amino-1-((3R,4S)-dihydroxy-pyrrolidin-1-yl)-(2R)-hydroxy-4-phenyl-butan-1-one hydrochloride were coupled according to Procedure A (1.5 equiv 1-hydroxybenzotriazole hydrate, 1.1 equiv 1-(3-dimethylamino-propyl)-3-ethylcarbodiimide hydrochloride, 25:1 dichloromethane:dimethylformamide; combined organic phases washed with water prior to saturated aqueous NaHCO₃).

mp 148–152° C.; CIMS m/e 464.0/465.9 (MH+). ¹H NMR (DMSO-d₆) δ11.71 (m, 1H), 7.84 (d, J=8.9 Hz, 1H), 7.23–6.98 (m, 7H), 5.05–4.74 (m, 3H), 4.39 (m, 1H), 4.20 (m, 1H), 4.02–3.88 (m, 2H), 3.54 (m, 0.5H), 3.41–3.06 (m, 3.5H), 2.94–2.83 (m, 2H).

Example 6a

2–Chloro-6H-thieno[2,3-b]pyrrole-5-carboxylic acid ethyl ester

Using a modified procedure by R. M. Kellogg et al. (*J. Org. Chem.*, 33: 2902–290 (1968)), to a 0° C. solution of 6H-thieno[2,3-b]pyrrole-5-carboxylic acid ethyl ester (Eras, J.; Galvez, C.; Garcia, F., *J. Heterocycl. Chem.*, 21: 215–217 (1984); 1.45 g, 7.44 mmol) in acetic acid (15 mL) and CHCl₃ (15 mL) was added N-chlorosuccinimide (1.04 g, 7.81 mmol) over 2 h. The reaction mixture was slowly allowed to warm to room temperature over several hours, stirred overnight, concentrated to remove the chloroform, diluted with water, basified with 5 N NaOH, and extracted with ethyl acetate. The combined organic phases were washed with saturated aqueous NaHCO₃, dried over MgSO₄, and concentrated. The product was purified by chromatron chromatography (radial) using 90:10 hexanes/diethyl ether and then then then the product obtained was recrystallized using hexanes/diethyl ether (90:10). Last, the product of the recrystallization was further purified by flash column chromatography using 90:10 petroleum ether/isopropyl ether. The resulting product was obtained as a white solid (824 mg, 48%).

CIMS m/e 228.2/230.2 ((M–H)+). ¹H NMR (CDCl₃) δ9.28 (br s, 1H), 6.98 (d, J=1.9 Hz, 1H), 6.88 (s, 1H), 4.33 (q, J=7.2 Hz, 2H), 1.35 (t, J=7.2 Hz, 3H).

Example 6b

2–Chloro-6H-thieno[2,3-b]pyrrole-5-carboxylic acid

2–Chloro-6H-thieno[2,3-b]pyrrole-5-carboxylic acid ethyl ester was hydrolyzed according to Procedure D (reaction heated at 85° C.).

CIMS m/e 200.1/202.1 ((M–H)+).

¹H NMR (DMSO-d₆) δ12.66 (br s, 1H), 12.08 (s, 1H), 7.11 (d, J=1.9 Hz, 1H), 6.86 (t, J=2.1 Hz, 1H).

Example 7

2–Chloro-6H-thieno[2,3-b]pyrrole-5-carboxylic acid [(1S)-benzyl-2-((3R,4S)-dihydroxy-pyrrolidin-1-yl)-2-oxo-ethyl]-amide 2–Chloro-6H-thieno[2,3-b]pyrrole-5-carboxylic acid and (2S)-amino-1-((3R,4S)-dihydroxy-pyrrolidin-1-yl)-3-phenyl-propan-1-one hydrochloride were coupled according to Procedure A (1.5 equiv 1-hydroxybenzotriazole hydrate, 1.1 equiv 1-(3-dimethylamino-propyl)-3-ethylcarbodiimide hydrochloride, 25:1 dichloromethane:dimethylformamide; combined organic phases washed with water prior to saturated aqueous NaHCO₃).

mp 142–145° C.; CIMS m/e 432.1/434.2 ((M–H)+). ¹H NMR (DMSO-d₆) δ11.72 (m, 1H), 8.55 (d, J=8.5 Hz, 1H), 7.28–7.10 (m, 7H), 5.00 (d, J=5.2 Hz, 0.5H), 4.99–4.70 (m, 2.5H), 4.09–3.76 (m, 2.5H), 3.41–3.24 (m, 2H), 3.13 (m, 1.5H), 3.02–2.87 (m, 2H).

Example 8

2,4-Dichloro-6H-thieno[2,3-b]pyrrole-5-carboxylic acid [(1S)-benzyl-3-((3R,4S)-dihydroxy-pyrrolidin-1-yl)-(2R)-hydroxy-3-oxo-propyl]-amide 2,4-Dichloro-6H-thieno[2,3-b]pyrrole-5-carboxylic acid and (3S)-amino-1-((3R,4S)-dihydroxy-pyrrolidin-1-yl)-(2R)-hydroxy-4-phenyl-butan-1-one hydrochloride were coupled according to Procedure A (1.5 equiv 1-hydroxybenzotriazole hydrate, 1.1 equiv 1-(3-dimethylamino-propyl)-3-ethylcarbodiimide hydrochloride, 25:1 dichloromethane:dimethylformamide, 0.06 M).

mp 130–134° C. (dec.); CIMS m/e 496.2/498.2 ((M–H)+). ¹H NMR (DMSO-d₆) δ12.13 (br s, 1H), 7.40–7.15 (m, 7H), 5.51 (d, J=5.8 Hz, 0.5H), 5.38 (d, J=6.3 Hz, 0.5H), 4.99 (d, J=4.9 Hz, 1H), 4.92 (d, J=4.8 Hz, 0.5H), 4.85 (d, J=4.1 Hz, 0.5H), 4.55–4.40 (m, 1H), 4.26 (m, 1H), 4.08–3.90 (m, 2H), 3.56–2.89 (m, 6H).

Example 8a 2,4-Dichloro-6H-thieno[2,3-b]pyrrole-5-carboxylic acid ethyl ester

To a 0° C. solution of 6H-thieno[2,3-b]pyrrole-5-carboxylic acid ethyl ester (180 mg, 0.92 mmol) in acetic acid (2 mL) and CHCl₃ (2 mL) was added N-chlorosuccinimide (294 mg, 2.2 mmol) over 30 min. The reaction mixture was slowly allowed to warm to room temperature over several hours, stirred overnight, concentrated to remove the chloroform, diluted with water, basified with 5 N NaOH, and extracted with ethyl acetate. The combined organic phases were washed with saturated aqueous NaHCO$_3$, dried over MgSO$_4$, and concentrated. The product was purified by Chromatron-chromatography (4:1 hexanes:ether) and obtained as a white solid (180 mg, 74%).

mp 166–167° C.; CIMS m/e 262.1/264.1 ((M–H)$^+$). $^1$H NMR (300 MHz, CDCl$_3$) δ9.21 (br s, 1H), 6.90 (s, 1H), 4.37 (q, J=7.2 Hz, 2H), 1.39 (t, J=7.2 Hz, 3H).

Example 8b 2,4-Dichloro-6H-thieno[2,3-b]pyrrole-5-carboxylic acid 2,4-Dichloro-6H-thieno[2,3-b]pyrrole-5-carboxylic acid ethyl ester was hydrolyzed according to Procedure E (reflux for 12 h before allowing to cool to room temperature; acidification with concentrated HCl; no purification).

CIMS m/e 234.0/236.0 ((M–H)$^+$). $^1$H NMR (DMSO-d$_6$) δ12.28 ( br s, 1H), 7.17 (s, 1H).

Example 9

(±)-4H-Thieno[3,2-b]pyrrole-5-carboxylic acid [1-benzyl-2-((3R,4S)-dihydroxy-pyrrolidin-1-yl)-2-oxo-ethyl]-amide 4H-Thieno[3,2-b]pyrrole-5-carboxylic acid (Soth, S.; Farnier, M.; Paulmier, C., *Can. J. Chem.* 56, 1429–34 (1978)) and (±)-2-amino-1-((3R,4S)-dihydroxy-pyrrolidin-1-yl)-3-phenyl-propan-1-one hydrochloride were coupled according to Procedure A (9:1 dichloromethane:-dimethylformamide, 0.06 M; combined organic phases washed with 2 N NaOH, dried over Na$_2$SO$_4$).

mp 212° C.; CIMS m/e 400.1 (MH$^+$). $^1$H NMR (DMSO-d$_6$) δ11.59 (m, 1H), 8.51 (d, J=8.5 Hz, 1H), 7.36 (d, J=5.2 Hz, 1H), 7.30–7.11 (m, 5H), 6.92 (m, 1H), 5.01 (d, J=5.0 Hz, 0.5H), 4.92 (d, J=4.8 Hz, 0.5H), 4.87–4.76 (m, 2H), 4.04–3.93 (m, 1H), 3.83 (m, 1.5H), 3.43–3.25 (m, 2.5), 3.13 (m, 1H), 3.03–2.86 (m, 2H).

Example 10

2-Bromo-4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide 2-Bromo-4H-thieno[3,2-b]pyrrole-5-carboxylic acid and (3S)-amino-1-((3R,4S)-dihydroxy-pyrrolidin-1-yl)-(2R)-hydroxy-4-phenyl-butan-1-one hydrochloride were coupled according to Procedure B (1.5 equiv 1-hydroxy-7-azabenzotriazole hydrate, 1.1 equiv 1-(3-dimethylamino-propyl)-3-ethylcarbodiimide hydrochloride, 25:1 dichloromethane:dimethylformamide; reaction mixture stirred for 5 d, concentrated to remove dichloromethane before workup; combined organic phases washed with water prior to saturated aqueous NaHCO$_3$).

mp 138–143° C.; CIMS m/e 508.0/510.0 (MH$^+$). $^1$H NMR (DMSO-d$_6$) δ11.68 (m, 1H), 7.86 (d, J=9.1 Hz, 1H), 7.25–7.18 (m, 4H), 7.12–7.08 (m, 2H), 7.02 (s, 1H), 5.05 (d, J=7.5 Hz, 0.5H), 4.95 (m, 1H), 4.88 (d, J=5.0 Hz, 0.5H), 4.81 (d, J=7.5 Hz, 0.5H), 4.75 (d, J=3.5 Hz, 0.5H), 4.46–4.37 (m, 1H), 4.20 (m, 1H), 4.08–3.85 (m, 2H), 3.54 (m, 1H), 3.40–3.05 (m, 3H), 2.95–2.81 (m, 2H).

Example 10a

2-Bromo-4H-thieno[3,2-b]pyrrole-5-carboxylic acid

2-Bromo-4H-thieno[3,2-b]pyrrole-5-carboxylic acid ethyl ester (Eras, J.; Galvez, C.; Garcia, F., *J. Heterocycl. Chem.*, 21: 215–217 (1984)) was hydrolyzed according to Procedure D (after cooling to room temperature, acidification with 2 N HCl; resultant precipitate filtered, suspended in toluene, concentrated; no purification).

CIMS m/e 244.0/246.0 ((M–H)$^+$). $^1$H NMR (DMSO-d$_6$) δ12.63 (s, 1H), 12.04 (s, 1H), 7.13 (s, 1H), 6.97 (s, 1H).

Example 11

4H-Thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide 4H-Thieno[3,2-b]pyrrole-5-carboxylic acid and (3S)-amino-1-((3R,4S)-dihydroxy-pyrrolidin-1-yl)-(2R)-hydroxy-4-phenyl-butan-1-one hydrochloride were coupled according to Procedure A (combined organic phases washed with 2 N NaOH, dried over Na$_2$SO$_4$).

mp 185–190° C.; CIMS m/e 430.1 (MH$^+$). $^1$H NMR (DMSO-d$_6$) δ11.57 (s, 0.5H), 11.53 (s, 0.5H), 7.80 (d, J=8.9 Hz, 1H), 7.32 (dd, J=0.9, 5.3 Hz, 1H), 7.23 (m, 4H), 7.12 (m, 1H), 7.07 (s, 1H), 6.91 (m, 1H), 5.06 (d, J=7.3 Hz, 0.5H), 4.96 (m, 1H), 4.89 (d, J=5.2 Hz, 0.5H), 4.82 (d, J=7.5 Hz, 0.5H), 4.76 (d, J=4.2 Hz, 0.5H), 4.45–4.38 (m, 1H), 4.21 (m, 1H), 4.01–3.86 (m, 2H), 3.55 (m, 1H), 3.40 (dd, J=4.9, 12.6 Hz, 0.5H), 3.23 (m, 1.5H), 3.17–3.07 (m, 1H), 2.97–2.83 (m, 2H).

Example 12

(±)-2-Bromo-4H-furo[3,2-b]pyrrole-5-carboxylic acid [1-benzyl-2-((3R,4S)-dihydroxy-pyrrolidin-1-yl)-2-oxo-ethyl]-amide 2-Bromo-4H-furo[3,2-b]pyrrole-5-carboxylic acid and (±)-2-amino-1-((3R,4S)-dihydroxy-pyrrolidin-1-yl)-3-phenyl-propan-1-one hydrochloride were coupled according to Procedure A (1:1 dichloromethane:dimethylformamide; reaction mixture stirred for 3 d; combined organic phases washed with 2 N NaOH, dried over Na$_2$SO$_4$).

mp 100–101° C. (dec.); CIMS m/e 462.2/464.1 (MH$^+$). $^1$H NMR (DMSO-d$_6$) δ11.33 (m, 1H), 8.41 (dd, J=2.8, 8.2 Hz, 1H), 7.27–7.18 (m, 4H), 7.13 (m, 1H), 6.93 (d, J=5.8 Hz, 1H), 6.69 (d, J=0.8 Hz, 1H), 4.98–4.75 (m, 3H), 3.99 (m, 0.5H), 3.93 (m, 0.5H), 3.81 (m, 1.5H), 3.41–3.21 (m, 2.5H), 3.12 (m, 1H), 3.00–2.82 (m, 2H).

Example 12a

2-Bromo-4H-furo[3,2-b]pyrrole-5-carboxylic acid

2-Bromo-4H-furo[3,2-b]pyrrole-5-carboxylic acid ethyl ester (Krutosikova, A.; Kovac, J.; Dandarova, M.; Lesko, J.; Ferik, S., *Collect. Czech. Chem. Commun.*, 46: 2564–2573 (1981)) was hydrolyzed according to Procedure E (4 equiv 2 N NaOH, ethanol; reflux 5h, room temperature overnight; after concentration to remove ethanol, residue partitioned between ethyl acetate and 2 N HCl; combined organic phases dried over Na$_2$SO$_4$; no purification).

$^1$H NMR (DMSO-d$_6$) δ12.47 (br s, 1H), 11.67 (s, 1H), 6.76 (d, J=0.8 Hz, 1H), 6.67 (t, J=0.8 Hz, 1H).

Example 13

2-Bromo-4H-furo[3,2-b]pyrrole-5-carboxylic acid [(1S)-benzyl-3-((3R,4S)-dihydroxy-pyrrolidin-1-yl)-(2R)-hydroxy-3-oxo-propyl]-amide 2-Bromo-4H-furo[3,2-b]pyrrole-5-carboxylic acid and (3S)-amino-1-((3R,4S)-dihydroxy-pyrrolidin-1-yl)-(2R)- hydroxy-4-phenyl-butan-1-one hydrochloride were coupled according to Procedure A (2:1 dichloromethane:dimethylformamide; reaction mixture stirred for 3 d; combined organic phases washed with 2 N NaOH, dried over $Na_2SO_4$).

mp 112–123° C. (dec.); CIMS m/e 492.1/494.1 (MH$^+$). $^1$H NMR (DMSO-d$_6$) δ11.31 (s, 0.5H), 11.27 (s, 0.5H), 7.71 (d, J=8.7 Hz, 1H), 7.25–7.18 (m, 4H), 7.11 (m, 1H), 6.81 (s, 1H), 6.68 (d, J=2.9 Hz, 1H), 5.05–4.73 (m, 3H), 4.44–4.34 (m, 1H), 4.17 (br s, 1H), 3.98–3.85 (m, 2H), 3.56–3.48 (m, 1H), (m, 3H), 2.94–2.80 (m, 2H).

Example 14

6H-Thieno[2,3-b]pyrrole-5-carboxylic acid [(1S)-benzyl-2-((3R,4S)-dihydroxy-pyrrolidin-1-yl)-2-oxo-ethyl]-amide 6H-Thieno[2,3-b]pyrrole-5-carboxylic acid and (2S)-amino-1-((3R,4S)-dihydroxy-pyrrolidin-1-yl)-3-phenyl-propan-1-one hydrochloride were coupled according to Procedure A (1.5 equiv 1-hydroxybenzotriazole hydrate, 1.1 equiv 1-(3-dimethylamino-propyl)-3-ethylcarbodiimide hydrochloride, 15:1 dichloromethane:dimethylformamide; reaction mixture stirred for 3 d; after saturated aqueous NaHCO$_3$, combined organic phases washed with water, dried over $Na_2SO_4$).

mp 179–184° C.; CIMS m/e 400.1 (MH$^+$), 398.2 ((M–H)$^+$). $^1$H NMR (300 MHz, DMSO-d$_6$) δ11.79 (br s 1H), 8.52 (d, J=8.3 Hz, 1H), 7.34–7.16 (m, 6H), 7.04 (m, 2H), 5.04 (d, J=5.1 Hz, 0.5H), 4.96 (d, J=4.9 Hz, 0.5H), 4.90–4.80 (m, 2H), 4.09–3.98 (m, 1H), 3.89 (m, 1.5H), 3.49–3.29 (m, 2.5H), 3.19 (m, 1H), 3.08–2.91 (m, 2H).

Example 15

2-Bromo-4H-thieno[3,2-b]pyrrole-5-carboxylic acid [(1S)-benzyl-2-((3R,4S)-dihydroxy-pyrrolidin-1-yl)-2-oxo-ethyl]-amide 2-Bromo-4H-thieno[3,2-b]pyrrole-5-carboxylic acid and (2S)-amino-1-((3R,4S)-dihydroxy-pyrrolidin-1-yl)-3-phenyl-propan-1-one hydrochloride were coupled according to Procedure A (1.5 equiv 1-hydroxybenzotriazole hydrate, 1.1 equiv 1-(3-dimethylamino-propyl)-3-ethylcarbodiimide hydrochloride, 25:1 dichloromethane:dimethylformamide; reaction mixture stirred for 3 d; combined organic phases washed with water prior to saturated aqueous NaHCO$_3$, dried over $Na_2SO_4$).

mp 140–143° C.; CIMS m/e 476.1 /478.0 ((M–H)$^+$). $^1$H NMR (300 MHz, DMSO-d$_6$) δ11.73 (m, 1H), 8.61 (d, J=8.3 Hz, 1H), 7.34–7.15 (m, 6H), 5.05–4.84 (m, 3H), 4.15–3.85 (m, 2.5H), 3.48–2.95 (m, 5.5H).

Example 16

2-Methyl-4H-thieno[3,2-b]pyrrole-5-carboxylic acid [(1S)-benzyl-2-((3R,4S)-dihydroxy-pyrrolidin-1-yl)-2-oxo-ethyl]-amide 2-Methyl-4H-thieno[3,2-b]pyrrole-5-carboxylic acid and (2S)-amino-1-((3R,4S)-dihydroxy-pyrrolidin-1-yl)-3-phenyl-propan-1-one hydrochloride were coupled according to Procedure A (1.5 equiv 1-hydroxybenzotriazole hydrate, 1.1 equiv 1-(3-dimethylamino-propyl)-3-ethylcarbodiimide hydrochloride, 25:1 dichloromethane:dimethylformamide; reaction mixture stirred for 3 d; combined organic phases washed with water prior to saturated aqueous NaHCO$_3$, dried over $Na_2SO_4$).

mp 128–130° C.; CIMS m/e 412.2 ((M–H)$^+$), 414.1 (MH$^+$). $^1$H NMR (DMSO-d$_6$) δ11.40 (m, 1H), 8.38 (m, 1H), 7.37–7.05 (m, 6H), 6.65 (s, 1H), 4.97 (d, J=5.2 Hz, 0.5H), 4.90–4.76 (m, 2.5H), 4.07–3.82 (m, 2.5H), 3.42–3.25 (m, 2H), 3.13 (m, 1.5H), 3.01–2.87 (m, 2H), 2.44 (d, J=1 Hz, 3H).

Example 16a

2-Methyl-4H-thieno[3,2-b]pyrrole-5-carboxylic acid ethyl ester

5-Methyl-2-thiophenecarboxaldehyde was annulated according to Procedure H (acrylate organic phases dried over $Na_2SO_4$).

mp 129–130° C.; CIMS m/e 208.2 ((M–H)$^+$), 210.2 (MH$^+$). $^1$H NMR (CDCl$_3$) δ8.90 (br s, 1H), 7.04 (s, 1H), 6.63 (s, 1H), 4.33 (q, J=7.1 Hz, 1H), 2.54 (s, 3H), 1.36 (t, J=7.2 Hz, 3H).

Example 16b

2-Methyl-4H-thieno[3,2-b]pyrrole-5-carboxylic acid

2-Methyl-4H-thieno[3,2-b]pyrrole-5-carboxylic acid ethyl ester was hydrolyzed according to Procedure D (after cooling to room temperature, acidification with 2 N HCl, extracted with ethyl acetate; organic phases dried over $Na_2SO_4$; no purification).

CIMS m/e 180.2 ((M–H)$^+$). $^1$H NMR (300 MHz, DMSO-d$_6$) δ12.35 (br s, 1H), 11.72 (s, 1H), 6.95 (s, 1H), 6.73 (s, 1H), 2.51 (s, 3H).

Example 17

2,4-Dichloro-6H-thieno[2,3-b]pyrrole-5-carboxylic acid acid [(1S)-benzyl-2-((3R,4S)-dihydroxy-pyrrolidin-1-yl)-2-oxo-ethyl]-amide 2,4-Dichloro-6H-thieno[2,3-b]pyrrole-5-carboxylic acid and (2S)-amino-1-((3R,4S)-dihydroxy-pyrrolidin-1-yl)-3-phenyl-propan-1-one hydrochloride were coupled according to Procedure A (1.5 equiv 1-hydroxybenzotriazole hydrate, 1.1 equiv 1-(3-dimethylamino-propyl)-3-ethylcarbodiimide hydrochloride, 25:1 dichloromethane:dimethylformamide; 2 d reaction time; combined organic phases washed with water prior to saturated aqueous NaHCO$_3$, dried over $Na_2SO_4$).

mp 203–204° C.; CIMS m/e 468.1/470.1 (MH$^+$). $^1$H NMR (DMSO-d$_6$) δ12.20 (s, 1H), 7.65–7.58 (m, 1H), 7.28–7.08 (m, 6H), 5.04 (d, J=3.3 Hz, 1H), 4.98–4.80 (m, 3H), 4.08–3.95 (m, 1H), 3.91–3.74 (m, 2H), 3.26–3.10 (m, 2H), 3.10–2.88 (m, 2H).

Example 18

2-Cyano-6H-thieno[2,3-b]pyrrole-5-carboxylic acid [(1S)-benzyl-2-(3-hydroxy-azetidin-1-yl)-2-oxo-ethyl]-amide 2-Cyano-6H-thieno[2,3-b]pyrrole-5-carboxylic acid and (2S)-amino-1-(3-hydroxy-azetidin-1-yl)-3-phenyl-propan-1-one hydrochloride were coupled according to Procedure B.

CIMS m/e 395.1 (MH$^+$). $^1$H NMR (DMSO-d$_6$) δ12.09 (s, 1H), 8.74 (d, J=8.5 Hz, 1H), 7.99 (s, 1H), 7.29–7.12 (m, 6H), 5.68 (m, 1H), 4.58 (m, 1H), 4.41 (m, 1H), 4.28 (m, 0.5H), 4.11–3.90 (m, 2H), 3.69 (m, 0.5H), 3.57–3.49 (m, 1H), 3.01–2.88 (m, 2H).

Example 18a

2-Cyano-6H-thieno[2,3-b]pyrrole-5-carboxylic acid

2-Formyl-6H-thieno[2,3-b]pyrrole-5-carboxylic acid (Soth, S. et al., *Bull. Soc. Chim. Fr.,* 2511–2515 (1975)) was treated with hydroxylamine hydrochloride according to Procedure G (100° C. for 13 h, 125° C. for 7 h; after cooling to room temperature, concentration gave crude product).

CIMS m/e 190.9 ((M–H)$^+$). $^1$H NMR (DMSO-d$_6$) δ13.03 (br s, 1H), 12.39 (br s, 1H), 7.97 (s, 1H), 7.04 (s, 1H).

Example 19

2–Chloro-6H-thieno[2,3-b]pyrrole-5-carboxylic acid [(1S)-benzyl-2-morpholin-4-yl-2-oxo-ethyl]-amide 2–Chloro-6H-thieno[2,3-b]pyrrole-5-carboxylic acid and (2S)-amino-1-morpholin-4-yl-3-phenyl-propan-1-one hydrochloride (See, for example, Suzuki, K.; Fujita, H.; Sasaki, Y.; Shiratori, M.; Sakurada, S.; Kisara, K., *Chem. Pharm. Bull.*, 36, 4834–40 (1988)) were coupled according to Procedure C (solution of product in ethyl acetate washed with water, dried over MgSO$_4$, concentrated).

mp 108–110° C.; CIMS m/e 416.3/418.2 ((M–H)$^+$). $^1$H NMR (DMSO-d$_6$) δ11.84 (m, 1H), 8.65 (d, J=8.2 Hz, 1H) 7.39–7.13 (m, 7H), 5.08 (q, J=7.6 Hz, 1H), 3.60–3.30 (m, 7H), 3.23 (m, 1H), 3.09–2.95 (m, 2H).

Example 20

2–Chloro-6H-thieno[2,3-b]pyrrole-5-carboxylic acid [(1S)-dimethylcarbamoyl-2-phenyl-ethyl]-amide 2–Chloro-6H-thieno[2,3-b]pyrrole-5-carboxylic acid and (2S)-amino-N,N-dimethyl-3-phenyl-propionamide trifluoroacetate (See, for example, Holladay, M. et al., *J. Med. Chem.*, 37: 630–5 (1994)) were coupled according to Procedure C (product washed with ethyl acetate).

mp 234–235° C.; CIMS m/e 374.2/376.2 ((M–H)$^+$). $^1$H NMR (DMSO-d$_6$) δ11.72 (s, 1H), 8.53 (d, J=8.1 Hz, 1H), 7.23 (m, 4H), 7.13 (m, 3H), 5.01 (m, 1H), 3.01–2.88 (m, 5H), 2.78 (s, 3H).

Example 21

2–Chloro-6H-thieno[2,3-b]pyrrole-5-carboxylic acid [(1S)-benzyl-2-(1,1-dioxo-1-thiazolidin-3-yl)-2-oxo-ethyl]-amide 2–Chloro-6H-thieno[2,3-b]pyrrole-5-carboxylic acid and (2S)-amino-1-(1,1-dioxo-1-thiazolidin-3-yl)-3-phenyl-propan-1-one hydrochloride (WO96/39384, Example 40a) were coupled according to Procedure C (solution of product in ethyl acetate washed with water, dried over MgSO$_4$, concentrated).

mp 125–129° C.; CIMS m/e 450.2/452.2 ((M–H)$^+$). $^1$H NMR (300 MHz, DMSO-d$_6$) δ11.80 (m 1H), 8.75 (dd, J=8.1, 12.9, 1H), 7.36 (m, 2H), 7.26–7.14 (m, 5H), 5.08–4.97 (m, 1H), 4.81 (m, 0.5H), 4.63 (d, J=11.4, 0.5H), 4.55 (d, J=12.5, 0.5H), 4.45 (d, J=12.4, 0.5H), 4.25 (m, 1H), 3.90–3.75 (m, 1H), 3.55–3.35 (m, 2H), 3.05 (m, 2H).

Example 22

1-{(2S)-[(2–Chloro-6H-thieno[2,3-b]pyrrole-5-carbonyl)-amino]-3-phenyl-propionyl}-piperidine-4-carboxylic acid ethyl ester 2–Chloro-6H-thieno[2,3-b]pyrrole-5-carboxylic acid and 1-[(2S)-amino-3-phenyl-propionyl]-piperidine-4-carboxylic acid ethyl ester hydrochloride were coupled according to Procedure C (solution of product in ethyl acetate washed with water, dried over MgSO$_4$, concentrated).

mp 104–105° C.; CIMS m/e 486.2/488.2 ((M–H)$^+$). $^1$H NMR (300 MHz, DMSO-d$_6$) δ11.84 (m, 1H), 8.64 (t, J=8.8 Hz, 1H), 7.32–7.14 (m, 7H), 5.10 (m, 1H), 4.30–3.89 (m, 4H), 3.15–2.92 (m, 3H), 2.80–2.50 (m, 2H), 1.83–1.69 (m, 2H), 1.52–0.94 (m, 5H).

Example 22a 1-((2S)-tert-Butoxycarbonylamino-3-phenyl-propionyl)-piperidine-4-carboxylic acid ethyl ester Boc-L-Phenylalanine (1.1 equiv) and piperidine-4-carboxylic acid ethyl ester were coupled according to Procedure A (1.5 equiv 1-hydroxybenzotriazole hydrate, 1.3 equiv 1-(3-dimethylamino-propyl)-3-ethylcarbodiimide hydrochloride, room temperature, dichloromethane; reaction mixture poured into water, acidified with 1 N HCl; resultant precipitate filtered, filtrate extracted with CHCl$_3$; organic phase washed sequentially with water and brine, dried over MgSO$_4$ before concentration).

CIMS m/e 405.2 (MH$^+$). $^1$H NMR (CDCl$_3$) 7.26–7.14 (m, 5H), 5.40 (dd, J=8.9,19.3 Hz, 1H), 4.82 (m, 1H), 4.34–4.24 (m, 1H), 4.09 (dq, J=2.0, 7.1 Hz, 2H), 3.57 (m, 1H), 2.99–2.88 (m, 2.5H), 2.72 (m, 1H), 2.45–2.32 (m, 1.5H), 1.95–1.79 (m, 1.5H), 1.58 (m, 2H), 1.40 (d, J=2.1 Hz, 9H), 1.23 (m, 3H), 0.68 (m, 0.5H).

Example 22b 1-((2S)-Amino-3-phenyl-propionyl)-piperidine-4-carboxylic acid ethyl ester hydrochloride To a solution of 1-((2S)-tert-butoxycarbonylamino-3-phenyl-propionyl)-piperidine-4-carboxylic acid ethyl ester (11 g, 27.20 mmol) in ethyl acetate (150 ml) was bubbled in HCl gas over 10 min. The reaction mixture was stirred overnight, concentrated, redissolved in ethyl acetate and ether, and concentrated. The crude product was precipitated with hexanes, filtered, and dried in vacuo to give the title product (9.1 mg, 98%).

CIMS m/e 305.1 (MH$^+$). $^1$H NMR (CDCl$_3$) δ8.56 (br s, 2H), 7.29–7.18 (m, 5H), 4.94–4.82 (m, 1H), 4.22–3.97 (m, 4H), 3.53 (dt, J=4.5, 12.7 Hz, 1H), 3.41–3.27 (m, 1H), 3.12 (m, 1H), 2.95 (m, 0.5H), 2.76 (t, J=10.9 Hz, 0.5H), 2.66 (m, 0.5H), 2.27 (m, 1H), 2.07 (m, 0.5H), 1.79–1.51 (m, 2H), 1.38–1.11 (m, 3.5H), 0.41 (m, 0.5H).

Example 23

2-Bromo-6H-thieno[2,3-b]pyrrole-5-carboxylic acid [(1S)-benzyl-2-(3-hydroxy-azetidin-1-yl)-2-oxo-ethyl]-amide 2-Bromo-6H-thieno[2,3-b]pyrrole-5-carboxylic acid and (2S)-amino-1-(3-hydroxy-azetidin-1-yl)-3-phenyl-propan-1-one hydrochloride were coupled according to Procedure B.

CIMS m/e448.1/450.0 (MH$^+$). $^1$H NMR (DMSO-d$_6$) δ11.77 (s, 1H), 8.55 (d, J=8.1 Hz, 1H), 7.26–7.10 (m, 7H), 5.00–4.76 (m, 3H), 4.07–3.94 (m, 1.5H), 3.83 (m, 1.5H), 3.40–3.22 (m, 1H), 3.13 (m, 2H), 2.93 (m, 2H).

Example 24

2-Methyl-4H-furo[3,2-b]pyrrole-5-carboxylic acid [(1S)-benzyl-2-((3R,4S)-dihydroxy-pyrrolidin-1-yl)-2-oxo-ethyl]-amide 2-Methyl-4H-furo[3,2-b]pyrrole-5-carboxylic acid (Krutosikova, A.; Kovac, J.; Dandarova, M.; Lesko, J.; Ferik, S., *Collect. Czech. Chem. Commun.*, 46: 2564–2573

(1981)) and (2S)-amino-1-((3R,4S)-dihydroxy-pyrrolidin-1-yl)-3-phenyl-propan-1-one hydrochloride were coupled according to Procedure B (acidic aqueous phase extracted with ethyl acetate; organic phases combined prior to basic work-up).

CIMS m/e 396.3 ((M−H)$^+$). $^1$H NMR (DMSO-d$_6$) δ10.96 (m, 1H), 8.23 (m, 1H), 7.27–7.19 (m, 4H), 7.14 (m, 1H), 6.83 (d, J=5.4 Hz, 1H), 6.15 (s, 1H), 4.97 (d, J=5.2 Hz, 0.5H), 4.89 (d, J=4.6 Hz, 0.5H), 4.80 (m, 2H), 3.99 (m, 0.5H), 3.93 (m, 0.5H), 3.82 (m, 1.5H), 3.38 (m, 1H), 3.25 (m, 1H), 3.13 (m, 1.5H), 3.00–2.85 (m, 2H), 2.31 (s, 3H).

Example 25

2-Trimethylsilanylethynyl-6H-thieno[2,3-b]pyrrole-5-carboxylic acid [(1S)-benzyl-2-(3-hydroxy-azetidin-1-yl)-2-oxo-ethyl]-amide Using a modified procedure of J. M. Tour et al. (*J. Org. Chem.*, 61: 6906–6921 (1996)), to a degassed solution of 2-bromo-6H-thieno[2,3-b]pyrrole-5-carboxylic acid [(1S)-benzyl-2-(3-hydroxy-azetidin-1-yl)-2-oxo-ethyl]-amide (106 mg, 0.24 mmol) in tetrahydrofuran (5 ml) was sequentially added diisopropylamine (36 μl, 0.26 mmol), a mixture of copper(I) iodide (9 mg, 0.05 mmol) and dichlorobis(triphenylphosphine)palladium(II) (68 mg, 0.1 mmol), and (trimethylsilyl)acetylene (41 μl, 0.29 mmol). The mixture was stirred overnight, poured into water, and extracted with dichloromethane. The combined organic phases were washed with saturated NaCl, dried over MgSO$_4$, and concentrated. The product was purified by Chromatotron-chromatography (dichloromethane; 20:1 dichloromethane:methanol) to give the title product (4.5 mg, 4%).

CIMS m/e 464.3 ((M−H)$^+$). $^1$H NMR (DMSO-d$_6$) δ11.86 (s, 1H), 8.54 (t, J=8.9 Hz, 1H), 7.31 (s, 1H), 7.23 (m, 4H), 7.13 (m, 2H), 5.66 (m, 1H), 4.56 (m, 1H), 4.41 (m, 1H), 4.28 (m, 0.5H), 4.11–3.89 (m, 2H), 3.66 (m, 0.5H), 3.57–3.46 (m, 1H), 2.99–2.85 (m, 2H), 0.23 (s, 9H).

Example 26

2-Ethynyl-6H-thieno[2,3-b]pyrrole-5-carboxylic acid [(1S)-benzyl-2-(3-hydroxy-azetidin-1-yl)-2-oxo-ethyl]-amide Using a procedure analogous to that of G. M. Whitesides et al. (*J. Org. Chem.*, 53: 2489–2496 (1988)), to a solution of 2-trimethylsilanylethynyl-6H-thieno[2,3-b]pyrrole-5-carboxylic acid [(1S)-benzyl-2-(3-hydroxy-azetidin-1-yl)-2-oxo-ethyl]-amide (110 mg, 0.02 mmol) in methanol (0.5 ml) was added a 5% aqueous solution of potassium hydroxide (7 μL, 0.06 mmol). The reaction mixture was stirred for 3 h, concentrated to remove the methanol, diluted with water, and extracted with dichloromethane. The organic phase dried over MgSO$_4$ and concentrated to give the title product (7 mg, 77%).

CIMS m/e 392.1 ((M−H)$^+$). $^1$H NMR (CDCl$_3$) δ7.32–7.16 (m, 7H), 7.03 (m, 2H), 4.66 (m, 1H), 4.47 (m, 1H), 4.17 (m, 1H), 4.00 (m, 1H), 3.75–3.56 (m, 3H), 3.35 (m, 1H), 3.04 (m, 2H).

Example 27

2-Fluoro-4H-thieno[3,2-b]pyrrole-5-carboxylic acid [(1S)-benzyl-2-((3R,4S)-dihydroxy-pyrrolidin-1-yl)-2-oxo-ethyl]-amide 2-Fluoro-4H-thieno[3,2-b]pyrrole-5-carboxylic acid and (2S)-amino-1-((3R,4S)-dihydroxy-pyrrolidin-1-yl)-3-phenyl-propan-1-one hydrochloride were coupled according to Procedure B (4 d reaction time).

mp 128–132° C.; CIMS m/e 416.1 ((M−H)$^+$), 418.2 (MH$^+$). $^1$H NMR (DMSO-d$_6$) δ11.72 (m, 1H), 8.49 (d, J=8.5 Hz, 1H), 7.28–7.13 (m, 6H), 6.71 (s, 1H), 4.99 (d, J=5.2 Hz, 0.5H), 4.91 (d, J=4.8 Hz, 0.5H), 4.86 (d, J=3.7 Hz, 1H), 4.79 (m, 1H), 4.01 (m, 0.5H), 3.94 (m, 0.5H), 3.83 (m, 1.5H), 3.42–3.24 (m, 2.5H), 3.14 (m, 1H), 3.01–2.84 (m, 2H).

Example 27a

2-Fluoro-4H-thieno[3,2-b]pyrrole-5-carboxylic acid ethyl ester

5-Fluoro-thiophene-2-carbaldehyde (see, for example, Schuetz, R. D. and Nilles, G. P., *J. Org. Chem.*, 36: 2188–90 (1971)) was annulated according to Procedure H (aldehyde and azido-acetic acid ethyl ester added as ethanol solution (0.6 M of ester); acrylate organic phase washed with saturated aqueous NaCl prior to drying; acrylate not purified).

CIMS m/e 212.1 ((M−H)$^+$). $^1$H NMR (CDCl$_3$) δ9.16 (br s, 1H), 7.03 (s, 1H), 6.51 (s, 1H), 4.33 (q, J=7.2 Hz, 2H), 1.36 (t, J=7.2 Hz, 3H).

Example 27b

2-Fluoro-4H-thieno[3,2-b]pyrrole-5-carboxylic acid

2-Fluoro-4H-thieno[3,2-b]pyrrole-5-carboxylic acid ethyl ester was hydrolyzed according to Procedure F (acidified aqueous phase extracted with ethyl acetate; combined organic phases dried over MgSO$_4$, concentrated).

CIMS m/e 184.1 ((M−H)$^+$). $^1$H NMR (DMSO-d$_6$) δ12.47 (br s, 1H), 12.03 (s, 1H), 6.96 (s, 1H), 6.73 (s, 1H).

Example 28

2-Cyano-4H-furo[3,2-b]pyrrole-5-carboxylic acid [(1S)-benzyl-2-(3-hydroxy-azetidin-1-yl)-2-oxo-ethyl]-amide 2-Cyano-4H-furo[3,2-b]pyrrole-5-carboxylic acid and (2S)-amino-1-(3-hydroxy-azetidin-1-yl)-3-phenyl-propan-1-one hydrochloride were coupled according to Procedure B (reaction mixture partitioned between ethyl acetate and water prior to acidic washing).

CIMS m/e 377.1 ((M−H)$^+$), 379.1 (MH$^+$). $^1$H NMR (DMSO-d$_6$) δ11.78 (s, 1H), 8.68 (t, J=8.2 Hz, 1H), 7.67 (s, 1H), 7.22 (m, 4H), 7.15 (m, 1H), 7.01 (d, J=3.1 Hz, 1H), 5.68 (m, 1H), 4.59 (m, 1H), 4.40 (m, 1H), 4.26 (m, 0.5H), 4.05 (m, 1H), 3.92 (m, 1H), 3.65 (m, 0.5H), 3.53 (m, 1H), 3.00–2.88 (m, 2H).

Example 28a

2-Cyano-4H-furo[3,2-b]pyrrole-5-carboxylic acid

2-Formyl-4H-furo[3,2-b]pyrrole-5-carboxylic acid (see, for example, Krutosikova, A.; Dandarova, M.; Alfoldi, J., *Chem. Pap.*, 48: 268–73 (1994)) was treated with hydroxylamine hydrochloride according to Procedure G.

CIMS m/e 174.9 ((M−H)$^+$). $^1$H NMR (DMSO-d$_6$) δ13.10–12.60 (br s, 1H), 12.05 (s, 1H), 7.73 (s, 1H), 6.75 (s, 1H).

Example 29

2–Chloro-4H-furo[3,2-b]pyrrole-5-carboxylic acid [(1S)-benzyl-2-((3R,4S)-dihydroxy-pyrrolidin-1-yl)-2-oxo-ethyl]-amide 2–Chloro-4H-furo[3,2-b]pyrrole-5-carboxylic acid and (2S)-amino-1-((3R,4S)-dihydroxy-pyrrolidin-1-yl)-3- phenyl-propan-1-one hydrochloride were coupled according to Procedure B (3 d reaction time; reaction mixture partitioned between ethyl acetate and water prior to acidic washing).

CIMS m/e 418.1/420.1 (MH+). $^1$H NMR (DMSO-d$_6$) δ11.36 (s, 1H), 8.42 (dd, J=2.9, 8.3 Hz, 1H), 7.27–7.10 (m, 5H), 6.94 (d, J=6.0 Hz, 1H), 6.63 (m, 1H), 4.99 (d, J=5.2 Hz, 0.5H), 4.91 (d, J=5.0 Hz, 0.5H), 4.86–4.77 (m, 2H), 4.00 (m, 0.5H), 3.94 (m, 0.5H), 3.81 (m, 1.5H), 3.43–3.21 (m, 2.5H), 3.13 (m, 1H), 3.00–2.85 (m, 2H).

Example 29a

2–Chloro-4H-furo[3,2-b]pyrrole-5-carboxylic acid ethyl ester

5–Chloro-furan-2-carbaldehyde (Snyder, H. R., Jr.; Seehausen, P. H., *J. Heterocycl. Chem.*, 10: 385–6 (1973)) was annulated according to Procedure H (8 equiv sodium; aldehyde and azido-acetic acid ethyl ester added as ethanol solution (0.9 M of ester); condensation reaction mixture allowed to warm to room temperature, stirred for 1 h, quenched at –40° C., diluted with water, and extracted with ether; acrylate not purified; crude furanopyrrole filtered before concentration).

CIMS m/e 212.0/214.1 ((M–H)+). $^1$H NMR (CDCl$_3$) δ8.69 (br s, 1H), 6.74 (dd, J=0.8, 1.7 Hz, 1H), 6.31 (d, J=0.6 Hz, 1H), 4.33 (q, J=7.1 Hz, 2H), 1.36 (t, J=7.1 Hz, 3H).

Example 29b

2-Chloro-4H-furo[3,2-b]pyrrole-5-carboxylic acid

2-Chloro-4H-furo[3,2-b]pyrrole-5-carboxylic acid ethyl ester was hydrolyzed according to Procedure F (room temperature overnight, 50° C. 4 h; acidified aqueous phase extracted with ethyl acetate; combined organic phases dried over MgSO$_4$, concentrated).

CIMS m/e 183.8/185.8 ((M–H)+). $^1$H NMR (DMSO-d$_6$) δ12.47 (br s, 1H), 11.70 (s, 1H), 6.70 (s, 1H), 6.67 (s, 1H).

Example 30

2-Chloro-4H-furo[3,2-b]pyrrole-5-carboxylic acid [(1S)-benzyl-3-((3R,4S)-dihydroxy-pyrrolidin-1-yl)-(2R)-hydroxy-3-oxo-propyl]-amide 2-Chloro-4H-furo[3,2-b]pyrrole-5-carboxylic acid and (3S)-amino-1-((3R,4S)-dihydroxy-pyrrolidin-1-yl)-(2R)-hydroxy-4-phenyl-butan-1-one were coupled according to Procedure B (3 d reaction time; reaction mixture partitioned between ethyl acetate and water prior to acidic washing).

CIMS m/e 448.1/450.1 (MH+). $^1$H NMR (DMSO-d$_6$) δ11.33 (m, 1H), 7.72 (d, J=8.7 Hz, 1H), 7.25–7.09 (m, 5H), 6.82 (s, 1H), 6.61 (dd, J=0.7, 3.0 Hz, 1H), 5.04 (d, J=7.3 Hz, 0.5H), 4.94 (m, 1H), 4.89 (d, J=5.0 Hz, 0.5H), 4.80 (d, J=7.5 Hz, 0.5H), 4.75 (d, J=4.2 Hz, 0.5H), 4.45–4.35 (m, 1H), 4.18 (m, 1H), 4.00–3.88 (m, 2H), 3.57–3.49 (m, 1H), 3.39 (m, 0.5H), 3.06 (m, 2.5H), 2.95–2.80 (m, 2H).

Example 31

1-{(2S)-[(2-Chloro-6H-thieno[2,3-b]pyrrole-5-carbonyl)-amino]-3-phenyl-propionyl}-piperidine-4-carboxylic acid 1-{(2S)-[(2-Chloro-6H-thieno[2,3-b]pyrrole-5-carbonyl)-amino]-3-phenyl-propionyl}-piperidine-4-carboxylic acid ethyl ester was hydrolyzed according to Procedure F (room temperature; after concentration, reaction residue partitioned between ethyl acetate and 1–2 N NaOH; aqueous phase acidified with 2 N HCl, extracted with ethyl acetate; combined organic phases dried over MgSO$_4$, concentrated; crude product washed with ether).

mp 145–150° C. $^1$H NMR (DMSO-d$_6$) δ12.21 (s, 1H), 11.83 (s, 0.5H), 11.77 (s, 0.5H), 8.58 (m, 1H), 7.26–7.11 (m, 7H), 5.05 (m, 1H), 4.23 (d, J=13.3 Hz, 0.5H), 4.10 (d, J=12.5 Hz, 0.5H), 3.93 (d, J=12.7 Hz, 0.5H), 3.85 (d, J=13.5 Hz, 0.5H), 3.11–2.90 (m, 3H), 2.77–2.61 (m, 1H), 2.49–2.39 (m, 1H), 1.75–1.65 (m, 2H), 1.43–1.17 (m, 1.5H), 1.07–0.97 (m, 0.5H).

Example 32

3-Chloro-4H-thieno[3,2-b]pyrrole-5-carboxylic acid [(1S)-benzyl-2-((3R,4S)-dihydroxy-pyrrolidin-1-yl)-2-oxo-ethyl]-amide 3-Chloro-4H-thieno[3,2-b]pyrrole-5-carboxylic acid and (2S)-amino-1-((3R,4S)-dihydroxy-pyrrolidin-1-yl)-3-phenyl-propan-1-one hydrochloride were coupled according to Procedure B (reaction mixture partitioned between ethyl acetate and water prior to acidic washing).

CIMS m/e 434.0/436.0 (MH+). $^1$H NMR (DMSO-d$_6$) δ12.09 (m, 1H), 8.57 (d, J=8.3 Hz, 1H), 7.40 (m, 0.5H), 7.28–7.10 (m, 6.5H), 5.00 (d, J=5.2 Hz, 0.5H), 4.92 (d, J=5.0 Hz, 0.5H), 4.84 (m, 2H), 4.10–3.93 (m, 1H), 3.82 (m, 1.5H), 3.44–3.23 (m, 2.5H), 3.13 (m, 1H), 3.03–2.87 (m, 2H).

Example 32a

3-Chloro-4H-thieno[3,2-b]pyrrole-5-carboxylic acid ethyl ester

4-Chloro-thiophene-2-carbaldehyde (Iriarte, J.; Martinez, E.; Muchowski, J. M., *J. Heterocycl. Chem.*, 13: 393–4 (1976)) was annulated according to Procedure H (aldehyde and azido-acetic acid ethyl ester added as ethanol solution (1.2 M of ester) such that reaction temperature maintained at 0° C.; reaction mixture allowed to warm to 10° C., stirred for 1.5 h, poured into cold saturated aqueous NH$_4$Cl; after ether extractions, combined acrylate organic phases washed with water until aqueous phase was neutral; acrylate not purified).

CIMS m/e 228.0 ((M–H)+). $^1$H NMR (CDCl$_3$) δ9.02 (br s, 1H), 7.24 (s, 1H), 7.10 (s, 1H), 4.37 (q, J=7.1 Hz, 2H), 1.38 (t, J=7.1 Hz, 3H).

Example 32b

3-Chloro-4H-thieno[3,2-b]pyrrole-5-carboxylic acid

3-Chloro-4H-thieno[3,2-b]pyrrole-5-carboxylic acid ethyl ester was hydrolyzed according to Procedure F (7 equiv LiOH—H$_2$O; room temperature overnight, then at 50° C. overnight again; acidified aqueous phase extracted with ethyl acetate; combined organic phases dried over MgSO$_4$, concentrated).

CIMS m/e 199.9/201.8 ((M–H)+). $^1$H NMR (DMSO-d$_6$) δ12.71 (br s, 1H), 12.40 (s, 1H), 7.48 (s, 1H), 7.06 (d, J=1.9 Hz, 1H).

Example 33

3-Chloro-4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide 3-Chloro-4H-thieno[3,2-b]pyrrole-5-carboxylic acid and (3S)-amino-1-((3R,4S)-dihydroxy-pyrrolidin-1-yl)-(2R)- hydroxy-4-phenyl-butan-1-one were coupled according to Procedure B (reaction mixture partitioned between ethyl acetate and water prior to acidic washing).

CIMS m/e 464.0/466.0 (MH$^+$). $^1$H NMR (DMSO-d$_6$) δ12.4 (m, 1H), 7.89 (d, J=8.9 Hz, 1H), 7.38 (s, 0.5H), 7.26–7.10 (m, 5.5H), 7.05 (d, J=3.1 Hz, 1H), 5.08 (d, J=7.1 Hz, 0.5H), 4.97–4.84 (m, 2H), 4.76 (d, J=4.2 Hz, 0.5H), 4.44 (m, 1H), 4.20 (m, 1H), 4.09–3.88 (m, 2H), 3.53 (m, 1H), 3.38 (m, 0.5H), 3.25–3.06 (m, 2.5H), 2.97–2.82 (m, 2H).

Example 34

3-Bromo-4H-thieno[3,2-b]pyrrole-5-carboxylic acid [(1S)-benzyl-2-((3R,4S)-dihydroxy-pyrrolidin-1-yl)-2-oxo-ethyl]-amide 3-Bromo-4H-thieno[3,2-b]pyrrole-5-carboxylic acid and (2S)-amino-1-((3R,4S)-dihydroxy-pyrrolidin-1-yl)-3-phenyl-propan-1-one hydrochloride were coupled according to Procedure B (reaction mixture partitioned between ethyl acetate and water prior to acidic washing).

CIMS m/e 475.9/478.2 ((M–H)$^+$). $^1$H NMR (DMSO-d$_6$) δ11.99 (m, 1H), 8.56 (d, J=8.3 Hz, 1H), 7.48 (d, J=1.2 Hz, 0.5H), 7.27–7.12 (m, 6.5H), 4.99 (d, J=5.2 Hz, 0.5H), 4.91 (d, J=5.2 Hz, 0.5H), 4.84 (m, 2H), 4.09–3.92 (m, 1.5H), 3.78 (m, 1.5H), 3.43–3.22 (m, 2H), 3.13 (m, 1H), 2.99–2.85 (m, 2H).

Example 34a

3-Bromo-4H-thieno[3,2-b]pyrrole-5-carboxylic acid

4-Bromo-thiophene-2-carbaldehyde was annulated according to Procedure H (aldehyde and azido-acetic acid ethyl ester added as ethanol solution (1.2 M of ester) such that reaction temperature maintained at 0° C.; reaction mixture allowed to warm to 10° C., stirred for 1 h, poured into cold saturated aqueous NH$_4$Cl; after ether extractions, combined acrylate organic phases washed with water until aqueous phase was neutral; acrylate not purified).

CIMS m/e 272.0/273.9 ((M–H)$^+$). $^1$H NMR (CDCl$_3$) δ8.99 (br s, 1H), 7.21 (s, 1H), 7.13 (d, J=1.9 Hz, 1H), 4.37 (q, J=7.2 Hz, 2H), 1.38 (t, J=7.2 Hz, 3H).

Example 34b

3-Bromo-4H-thieno[3,2-b]pyrrole-5-carboxylic acid

3-Bromo-4H-thieno[3,2-b]pyrrole-5-carboxylic acid ethyl ester was hydrolyzed according to Procedure F (7 equiv LiOH—H$_2$O; room temperature overnight, then at 50° C. overnight again; acidified aqueous phase extracted with ethyl acetate; combined organic phases dried over MgSO$_4$, concentrated).

CIMS m/e 243.9/245.9 ((M–H)$^+$). $^1$H NMR (DMSO-d$_6$) δ12.69 (br s, 1H), 12.33 (s, 1H), 7.56 (s, 1H), 7.08 (s, 1H).

Example 35

3-Bromo-4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide 3-Bromo-4H-thieno[3,2-b]pyrrole-5-carboxylic acid and (3S)-amino-1-((3R,4S)-dihydroxy-pyrrolidin-1-yl)-(2R)-hydroxy-4-phenyl-butan-1-one were coupled according to Procedure B (reaction mixture partitioned between ethyl acetate and water prior to acidic washing).

CIMS m/e 508.0/510.0 (MH$^+$). $^1$H NMR (DMSO-d$_6$) δ11.96 (s, 0.5H), 11.91 (s, 0.5H), 7.90 (d, J=9.3 Hz, 1H), 7.46 (s, 0.5H), 7.22 (m, 4.5H), 7.12 (m, 1H), 7.04 (m, 1H), 5.08 (d, J=6.9 Hz, 0.5H), 4.94 (m, 1H), 4.89 (d, J=5.0 Hz, 0.5H), 4.85 (d, J=7.1 Hz, 0.5H), 4.75 (d, J=4.4 Hz, 0.5H), 4.45 (m, 1H), 4.20 (m, 1H), 4.08–3.87 (m, 2H), 3.53 (m, 1H), 3.40–3.30 (m, 0.5H), 3.22 (m, 1H), 3.15–3.05 (m, 1.5H), 2.98–2.82 (m, 2H).

Example 36

2-Chloro-4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide 2-Chloro-4H-thieno[3,2-b]pyrrole-5-carboxylic acid and (3S)-amino-1-((3R,4S)-dihydroxy-pyrrolidin-1-yl)-(2R)-hydroxy-4-phenyl-butan-1-one were coupled according to Procedure B (reaction mixture partitioned between ethyl acetate and water prior to acidic washing).

CIMS m/e 464.0/466.0 (MH$^+$). $^1$H NMR (DMSO-d$_6$) δ11.72 (s, 0.5H), 11.67 (s, 0.5H), 7.85 (d, J=9.1 Hz, 1H), 7.21 (m, 4H), 7.12 (m, 1H), 7.00 (m, 2H), 5.05 (d, J=7.1 Hz, 0.5H), 4.95 (m, 1H), 4.89 (d, J=4.8 Hz, 0.5H), 4.81 (d, J=7.5 Hz, 0.5H), 4.75 (d, J=3.9 Hz, 0.5H), 4.41 (m, 1H), 4.20 (m, 1H), 4.00–3.87 (m, 2H), 3.54 (m, 1H), 3.40 (m, 0.5H), 3.22 (m, 1.5H), 3.06 (m, 1H), 2.94–2.80 (m, 2H).

Example 36a

2-Chloro-4H-thieno[3,2-b]pyrrole-5-carboxylic acid ethyl ester

5-Chloro-thiophene-2-carbaldehyde was annulated according to Procedure H (aldehyde and azido-acetic acid ethyl ester added as ethanol solution (1.2 M of ester) such that reaction temperature maintained at 0–5° C.; reaction mixture allowed to warm to room temperature, stirred for 2 h, poured into cold saturated aqueous NH$_4$Cl; after ether extractions, combined acrylate organic phases washed with water until aqueous phase was neutral; 0.5 M solution of crude acrylate heated for 1.5 h).

CIMS m/e 228.0/229.9 ((M–H)$^+$). $^1$H NMR (CDCl$_3$) δ9.04 (br s, 1H), 7.02 (m, 1H), 6.88 (m, 1H), 4.34 (q, J=7.2 Hz, 2H), 1.37 (t, J=7.2 Hz, 3H).

Example 36b

2-Chloro-4H-thieno[3,2-b]pyrrole-5-carboxylic acid

2-Chloro-4H-thieno[3,2-b]pyrrole-5-carboxylic acid ethyl ester was hydrolyzed according to Procedure F (50° C. 9 h).

CIMS m/e 199.9/201.8 ((M–H)$^+$). $^1$H NMR (DMSO-d$_6$) δ12.62 (s, 1H), 12.04 (s, 1H), 7.05 (s, 1H), 6.97 (s, 1H).

Example 37

2-Chloro-4H-thieno[3,2-b]pyrrole-5-carboxylic acid [(1S)-benzyl-2-((3R,4S)-dihydroxy-pyrrolidin-1-yl)-2-oxo-ethyl]-amide 2-Chloro-4H-thieno[3,2-b]pyrrole-5-carboxylic acid and (2S)-amino-1-((3R,4S)-dihydroxy-pyrrolidin-1-yl)-3-phenyl-propan-1-one hydrochloride were coupled according to Procedure B (reaction mixture partitioned between ethyl acetate and water prior to acidic washing).

CIMS m/e 434.0/436.0 (MH$^+$). $^1$H NMR (DMSO-d$_6$) δ11.73 (m, 1H), 8.57 (d, J=7.9 Hz, 1H), 7.28–7.19 (m, 4H), 7.13 (m, 2H), 7.01 (d, J=2.7 Hz, 1H), 5.00 (d, J=5.2 Hz, 0.5H), 4.92 (d, J=5.2 Hz, 0.5H), 4.86 (m, 1H), 4.79 (m, 1H), 4.08–3.94 (m, 1H), 3.82 (m, 1.5H), 3.42–3.24 (m, 2H), 3.14 (m, 1.5H), 3.01–2.87 (m, 2H).

Example 38

3-Methyl-4H-thieno[3,2-b]pyrrole-5-carboxylic acid [(1S)-benzyl-2-((3R,4S)-dihydroxy-pyrrolidin-1-yl)-2-oxo-ethyl]-amide 3-Methyl-4H-thieno[3,2-b]pyrrole-5-carboxylic acid and (2S)-amino-1-((3R,4S)-dihydroxy-pyrrolidin-1-yl)-3-phenyl-propan-1-one hydrochloride were coupled according to Procedure B (reaction mixture partitioned between ethyl acetate and water prior to acidic washing).

CIMS m/e 412.1 ((M–H)$^+$), 414.0 (MH$^+$). $^1$H NMR (DMSO-d$_6$) δ11.69 (m, 1H), 8.45 (m, 1H), 7.28–7.18 (m, 4H), 7.12 (m, 2H), 6.93 (d, J=1.0 Hz, 1H), 4.98 (d, J=5.2 Hz, 0.5H), 4.90 (d, J=5.0 Hz, 0.5H), 4.83 (m, 2H), 4.03–3.92 (m, 1H), 3.83 (m, 1.5H), 3.42–3.23 (m, 2.5H), 3.14 (m, 1H), 3.03–2.88 (m, 2H), 2.24 (s, 3H).

Example 38a

3-Methyl-4H-thieno[3,2-b]pyrrole-5-carboxylic acid ethyl ester

4-Methyl-thiophene-2-carbaldehyde (Detty, M. R.; Hays, D. S., *Heterocycles*, 40: 925–37 (1995)) was annulated according to Procedure H (aldehyde and azido-acetic acid ethyl ester added as ethanol solution (1.1 M of ester); reaction poured into cold saturated aqueous NH$_4$Cl; after ether extractions, acrylate organic phase washed with water until aqueous phase was neutral; acrylate not purified).

CIMS m/e 207.9 ((M–H)$^+$), 209.9 (MH$^+$). $^1$H NMR (CDCl$_3$) δ9.02 (br s, 1H), 7.09 (d, J=1.9 Hz, 1H), 6.91 (d, J=1.0 Hz, 1H), 4.35 (quart, J=7.3 Hz, 1H), 2.32 (d, J=1.2 Hz, 3H), 1.38 (t, J=7.2 Hz, 3H).

Example 38b

3-Methyl-4H-thieno[3,2-b]pyrrole-5-carboxylic acid

3-Methyl-4H-thieno[3,2-b]pyrrole-5-carboxylic acid ethyl ester was hydrolyzed according to Procedure F (50° C. 13 h; acidified aqueous phase extracted with ethyl acetate; combined organic phases dried over MgSO$_4$, concentrated).

CIMS m/e 179.9 ((M–H)$^+$), 181.8 (MH$^+$). $^1$H NMR (DMSO-d$_6$) δ12.45 (br s, 1H), 11.99 (s, 1H), 7.02 (m, 1H), 6.96 (m, 1H), 2.25 (s, 3H).

Example 39

3-Methyl-4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide 3-Methyl-4H-thieno[3,2-b]pyrrole-5-carboxylic acid and (3S)-amino-1-((3R,4S)-dihydroxy-pyrrolidin-1-yl)-(2R)-hydroxy-4-phenyl-butan-1-one were coupled according to Procedure B (reaction mixture partitioned between ethyl acetate and water prior to acidic washing).

CIMS m/e 442.1 ((M–H)$^+$), 444.0 (MH$^+$). $^1$H NMR (DMSO-d$_6$) δ11.66 (s, 0.5H), 11.62 (s, 0.5H), 7.76 (d, J=8.9 Hz, 1H), 7.22 (m, 4H), 7.11 (m, 1H), 7.01 (d, J=1.7 Hz, 1H), 6.91 (s, 1H), 5.06 (d, J=7.3 Hz, 0.5H), 4.95 (m, 1H), 4.90 (d, J=5.0 Hz, 0.5H), 4.82 (d, J=7.5 Hz, 0.5H), 4.77 (d, J=4.4 Hz, 0.5H), 4.44 (m, 1H), 4.21 (m, 1H), 4.01–3.87 (m, 2H), 3.55 (m, 1H), 3.40 (dd, J=5.0, 12.6 Hz, 0.5H), 3.24 (m, 1.5H), 3.16–3.06 (m, 1H), 2.97–2.83 (m, 2H), 2.23 (s, 3H).

Example 40

2-Cyano-4H-thieno[3,2-b]pyrrole-5-carboxylic acid [(1S)-benzyl-2-((3R,4S)-dihydroxy-pyrrolidin-1-yl)-2-oxo-ethyl]-amide 2-Cyano-4H-thieno[3,2-b]pyrrole-5-carboxylic acid and (2S)-amino-1-((3R,4S)-dihydroxy-pyrrolidin-1-yl)-3-phenyl-propan-1-one hydrochloride were coupled according to Procedure B (reaction mixture partitioned between ethyl acetate and water prior to acidic washing).

CIMS m/e 423.1 ((M–H)$^+$), 425.1 (MH$^+$). $^1$H NMR (DMSO-d$_6$) δ12.15 (m, 1H), 8.85 (d, J=8.3 Hz, 1H), 7.79 (m, 1H), 7.29–7.11 (m, 6H), 5.00 (m, 0.5H), 4.93–4.78 (m, 2.5H), 4.04–3.93 (m, 1H), 3.81 (m, 1.5H), 3.43–3.25 (m, 2.5H), 3.15 (m, 1H), 3.03–2.89 (m, 2H).

Example 40a

2-Formyl-4H-thieno[3,2-b]pyrrole-5-carboxylic acid

2-Formyl-4H-thieno[3,2-b]pyrrole-5-carboxylic acid ethyl ester (see, for example, Gale, W. W. et al., *J. Org. Chem.*, 29: 2160–2165 (1964)) was hydrolyzed according to Procedure F (50° C. overnight; acidified aqueous phase extracted with ethyl acetate; combined organic phases dried over MgSO$_4$, concentrated).

CIMS m/e 193.9 ((M–H)$^+$), 195.8 (MH$^+$). $^1$H NMR (DMSO-d$_6$) δ13.38–12.78 (br s, 1H), 12.43 (s, 1H), 9.90 (s, 1H), 7.92 (s, 1H), 7.08 (s, 1H).

Example 40b

2-Cyano-4H-thieno[3,2-b]pyrrole-5-carboxylic acid

2-Formyl-4H-thieno[3,2-b]pyrrole-5-carboxylic acid was treated with hydroxylamine hydrochloride according to Procedure G.

CIMS m/e 190.9 ((M–H)$^+$). $^1$H NMR (DMSO-d$_6$) δ13.06 (br s, 1H), 12.45 (s, 1H), 7.84 (s, 1H), 7.09 (s, 1H).

Example 41

2-Cyano-4H-furo[3,2-b]pyrrole-5-carboxylic acid [(1S)-benzyl-3-((3R,4S)-dihydroxy-pyrrolidin-1-yl)-(2R)-hydroxy-3-oxo-propyl]-amide 2-Cyano-4H-furo[3,2-b]pyrrole-5-carboxylic acid and (3S)-amino-1-((3R,4S)-dihydroxy-pyrrolidin-1-yl)-(2R)-hydroxy-4-phenyl-butan-1-one were coupled according to Procedure A (1 equiv triethylamine, dimethylformamide; 4 d reaction time; reaction mixture partitioned between ethyl acetate and water; organic phase washed with 2 N HCl prior to saturated aqueous NaHCO$_3$).

mp 137–140° C.; CIMS m/e 437.1 ((M–H)$^+$), 439.0 (MH$^+$). $^1$H NMR (DMSO-d$_6$) δ11.70 (m, 1H), 7.99 (d, J=8.9 Hz, 1H), 7.65 (m, 1H), 7.22 (m, 4H), 7.12 (m, 1H), 6.91 (s, 1H), 5.09 (d, J=7.1 Hz, 0.5H), 4.95 (m, 1H), 4.89 (d, J=5.2 Hz, 0.5H), 4.83 (d, J=7.3 Hz, 0.5H), 4.76 (d, J=3.9 Hz, 0.5H), 4.42 (m, 1H), 4.21 (m, 1H), 4.08–3.89 (m, 2H), 3.61–3.50 (m, 1H), 3.40 (m, 0.5H), 3.24 (m, 1.5H), 3.13 (m, 1H), 2.95–2.80 (m, 2H).

Example 42

3-Bromo-4H-furo[3,2-b]pyrrole-5-carboxylic acid [(1S)-benzyl-2-((3R,4S)-dihydroxy-pyrrolidin-1-yl)-2-oxo-ethyl]-amide 3-Bromo-4H-furo[3,2-b]pyrrole-5-carboxylic acid and (2S)-amino-1-((3R,4S)-dihydroxy-pyrrolidin-1-yl)-3- phenyl-propan-1-one hydrochloride were coupled according to Procedure A (dimethylformamide; reaction mixture partitioned between ethyl acetate and water; organic phase washed with 2 N HCl prior to saturated aqueous NaHCO$_3$).

mp 140° C. dec.; CIMS m/e 461.9/463.9 (MH$^+$). $^1$H NMR (300 MHz, DMSO-d$_6$) δ11.75 (m, 1H), 8.47 (d, J=8.6 Hz, 1H), 7.90 (d, J=0.8 Hz, 1H), 7.33–7.15 (m, 5H), 6.98 (dd, J=1.5, 3.4 Hz, 1H), 5.03 (d, J=5.3 Hz, 0.5H), 4.95 (d, J=5.1 Hz, 0.5H), 4.91–4.83 (m, 2H), 4.13–3.97 (m, 1H), 3.86 (m, 1.5H), 3.48–3.25 (m, 2.5H), 3.18 (m, 1H), 3.08–2.92 (m, 2H).

Example 42a

3-Bromo-4H-furo[3,2-b]pyrrole-5-carboxylic acid ethyl ester

4-Bromo-2-furaldehyde was annulated according to Procedure H (aldehyde and azido-acetic acid ethyl ester added as ethanol solution (1 M of ester) to −20° C. ethoxide solution; −20° C. 35 min, −5° C. 1.5 h, 5° C. 15 min; reaction poured into cold saturated aqueous NH$_4$Cl; after ether extraction, acrylate organic phase washed with water until aqueous phase was neutral; 0.5 M solution of crude acrylate heated).

CIMS m/e 257.8/259.8 (MH$^+$). $^1$H NMR (300 MHz, CDCl$_3$) δ8.81 (br s, 1H), 7.48 (s, 1H), 6.79 (d, J=1.8 Hz, 1H), 4.35 (q, J=7.1 Hz, 2H), 1.36 (t, J=7.1 Hz, 3H).

Example 42b

3-Bromo-4H-furo[3,2-b]pyrrole-5-carboxylic acid

3-Bromo-4H-furo[3,2-b]pyrrole-5-carboxylic acid ethyl ester was hydrolyzed according to Procedure F (50° C. 14 h; acidified aqueous phase extracted with ethyl acetate; organic phase dried over MgSO$_4$, concentrated).

CIMS m/e 228.0/230.0 ((M−H)$^+$). $^1$H NMR (300 MHz, DMSO-d$_6$) δ12.60 (br s, 1H), 12.06 (br s, 1H), 7.98 (s, 1H), 6.77 (d, J=1.8 Hz, 1H).

Example 43

3-Bromo-4H-furo[3,2-b]pyrrole-5-carboxylic acid [(1S)-benzyl-3-((3R,4S)-dihydroxy-pyrrolidin-1-yl)-(2R)-hydroxy-3-oxo-propyl]-amide 3-Bromo-4H-furo[3,2-b]pyrrole-5-carboxylic acid and (3S)-amino-1-((3R,4S)-dihydroxy-pyrrolidin-1-yl)-(2R)-hydroxy-4-phenyl-butan-1-one were coupled according to Procedure A (1 equiv triethylamine, dimethylformamide; reaction mixture partitioned between ethyl acetate and water; organic phase washed with 2 N HCl prior to saturated aqueous NaHCO$_3$).

mp 140° C. dec; CIMS m/e 492.0/494.0 (MH$^+$). $^1$H NMR (300 MHz, DMSO-d$_6$) δ11.73 (s, 0.5H), 11.68 (s, 0.5H), 7.88 (d, J=0.7 Hz, 1H), 7.79 (d, J=8.9 Hz, 1H), 7.27 (m, 4H), 7.17 (m, 1H), 6.87 (s, 1H), 5.18–4.74 (m, 3H), 4.56–4.40 (m, 1H), 4.24 (s, 1H), 4.05–3.94 (m, 1.5H), 3.64–3.11 (m, 4.5H), 3.02–2.85 (m, 2H).

Example 44

4H-1,7-Dithia-4-aza-cyclopenta[a]pentalene-5-carboxylic acid [(1S)-benzyl-3-((3R,4S)-dihydroxy-pyrrolidin-1-yl)-(2R)-hydroxy-3-oxo-propyl]-amide 4H-1,7-Dithia-4-aza-cyclopenta[a]pentalene-5-carboxylic acid and (3S)-amino-1-((3R,4S)-dihydroxy-pyrrolidin-1-yl)-(2R)-hydroxy-4-phenyl-butan-1-one were coupled according to Procedure B (2:1 dichloromethane:dimethylformamide; reaction mixture partitioned between ethyl acetate and water; organic phase washed with 2 N HCl prior to saturated aqueous NaHCO$_3$).

CIMS m/e 484.0 ((M−H)$^+$), 486.0 (MH$^+$). $^1$H NMR (DMSO-d$_6$) δ12.00 (s, 0.5H), 11.95 (s, 0.5H), 7.83 (m, 1H), 7.55 (dd, J=0.8, 5.2 Hz, 1H), 7.35 (dd, J=1.2, 5.2 Hz, 1H), 7.23 (m, 4H), 7.12 (m, 2H), 5.07 (d, J=7.3 Hz, 0.5H), 4.96 (m, 1H), 4.90 (d, J=5.0 Hz, 0.5H), 4.81 (d, J=7.5 Hz, 0.5H), 4.76 (d, J=4.2 Hz, 0.5H), 4.44 (m, 1H), 4.20 (m, 1H), 4.08–3.88 (m, 1.5H), 3.57 (m, 1H), 3.40 (m, 0.5H), 3.26 (m, 1.5H), 3.17–3.07 (m, 1.5H), 2.97–2.84 (m, 2H).

Example 44a 4H-1,7-Dithia-4-aza-cyclopenta[a]pentalene-5-carboxylic acid ethyl ester Thieno[2,3-b]thiophene-2-carbaldehyde (Dopper, J. H. et al., J. Am. Chem. Soc., 95: 3692–8 (1973)) was annulated according to Procedure H (aldehyde and azido-acetic acid ethyl ester added as ethanol solution (1 M of ester) to −20° C. ethoxide solution; −20° C. 30 min, −20° C. to room temperature over 2.5 h; reaction poured into cold saturated aqueous NH$_4$Cl; after ether extraction, acrylate organic phase washed with water until aqueous phase was neutral; 0.35 M solution of crude acrylate heated).

CIMS m/e 250.1 ((M−H)$^+$), 251.9 (MH$^+$). $^1$H NMR (CDCl$_3$) δ9.46 (br s, 1H), 7.35 (d, J=5.3 Hz, 1H), 7.29 (d, J=5.3 Hz, 1H), 7.14 (d, J=2.0 Hz, 1H), 4.38 (q, J=7.1 Hz, 2H), 1.39 (t, J=7.1 Hz, 3H).

Example 44b 4H-1,7-Dithia-4-aza-cyclopenta[a]pentalene-5-carboxylic acid 4H-1,7-Dithia-4-aza-cyclopenta[a]pentalene-5-carboxylic acid ethyl ester was hydrolyzed according to Procedure F (50° C. 11 h).

CIMS m/e 222.0 ((M−H)$^+$). $^1$H NMR (DMSO-d$_6$) δ12.51 (s, 1H), 12.32 (s, 1H), 7.59 (d, J=5.3 Hz, 1H), 7.38 (d, J=5.3 Hz, 1H), 7.05 (d, J=1.9 Hz, 1H).

Example 45

4H-1,7-Dithia-4-aza-cyclopenta[a]pentalene-5-carboxylic acid [(1S)-benzyl-2-((3R,4S)-dihydroxy-pyrrolidin-1-yl)-2-oxo-ethyl]-amide 4H-1,7-Dithia-4-aza-cyclopenta[a]pentalene-5-carboxylic acid and (2S)-amino-1-((3R,4S)-dihydroxy-pyrrolidin-1-yl)-3-phenyl-propan-1-one hydrochloride were coupled according to Procedure B (1:1 dichloromethane:dimethylformamide; reaction mixture partitioned between ethyl acetate and water; organic phase washed with 2 N HCl prior to saturated aqueous NaHCO$_3$).

CIMS m/e 454.0 ((M−H)$^+$), 456.0 (MH$^+$). $^1$H NMR (DMSO-d$_6$) δ12.03 (m, 1H), 8.53 (d, J=8.1 Hz, 1H), 7.55 (dd, J=0.8, 5.2 Hz, 1H), 7.34 (dd, J=2.7, 5.2 Hz, 1H), 7.29–7.19 (m, 5H), 7.12 (m, 1H), 4.99 (d, J=5.2 Hz, 0.5H), 4.91 (d, J=5.0 Hz, 0.5H), 4.84 (m, 2H), 3.98 (m, 1H), 3.83 (m, 2H), 3.41–3.29 (m, 3H), 3.13 (m, 1H), 2.95 (m, 2H).

Example 46

2-Chloro-3-methyl-4H-thieno[3,2-b]pyrrole-5-carboxylic acid [(1S)-benzyl-2-((3R,4S)-dihydroxy-pyrrolidin-1-yl)-2-oxo-ethyl]-amide 2-Chloro-3-methyl-4H-thieno[3,2-b]pyrrole-5-carboxylic acid and (2S)-amino-1-((3R,4S)-dihydroxy-pyrrolidin-1- yl)-3-phenyl-propan-1-one hydrochloride were coupled according to Procedure B (1:1 dichloromethane:dimethylformamide; 2 d reaction time; reaction mixture concentrated to remove dichloromethane; partitioned between ethyl acetate and water; organic phase washed with 2 N HCl prior to saturated aqueous NaHCO$_3$).

mp 139–141° C.; CIMS m/e 448.1/450.1 (MH$^+$). $^1$H NMR (DMSO-d$_6$) δ11.95 (m, 1H), 8.54 (d, J=7.9 Hz, 1H), 7.28–7.18 (m, 4H), 7.13 (m, 2H), 4.98 (d, J=5.2 Hz, 0.5H), 4.90 (d, J=4.6 Hz, 0.5H), 4.83 (m, 2H), 4.02–3.92 (m, 1H), 3.82 (m, 1.5H), 3.41–3.22 (m, 2.5H), 3.14 (m, 1H), 3.01–2.90 (m, 2H), 2.20 (d, J=2.5 Hz, 3H).

Example 46a

5-Chloro-4-methyl-thiophene-2-carbaldehyde

Using a modified procedure of Silverstein et al. (Organic Synthesis Coll. Vol 4, Wiley, New York, 1963, N. Rabjohn, ed. p 831), to a 80° C. pale yellow solution of 2-chloro-3-methyl-thiophene (Crast, L. B., Jr. U.S. Pat. No. 3,290,291, Example 2; 70 g, 0.53 mol) in dimethylformamide (48.3 g, 0.66 mol) was added phosphorous oxychloride (101.5 g, 0.66 mol) dropwise over 45 min, while maintaining temperature at 80–97° C. The dark brown solution was stirred at 90° C. for 3 h and poured slowly into water (500 mL) at 90° C. The resultant mixture was steam distilled and the distillate was cooled to 0° C., affording white crystals. The first 500 ml of distillate was extracted with chloroform and concentrated and the residue was recrystallized from hexane (150 ml) at −50° C. The crude product (8.6 g) was dissolved in hexane (100 ml) and the insoluble material was filtered. The filtrate was diluted with hexane (50 ml), stirred with Norit® (2 g), and concentrated. The product was purified by recrystallization from hexane (50 ml) at −40° C. and obtained as white crystals (7.5 g, 13%). The remaining distillate from the steam distillation was extracted with chloroform (2×250 ml) and the white crystals dissolved in chloroform (1.5 l). The combined organic phases were dried over MgSO$_4$, filtered, stirred with Norit® (30 g) for 15 min, and concentrated. The residue was dissolved in hexane (350 ml), the insoluble material was filtered, the filtrate was stirred at −15° C. for 10 min, and the resultant precipitate was filtered. The title product was obtained as pale yellow crystals (48.6 g, 83%).

mp 39–40° C.

Example 46b

2-Chloro-3-methyl-4H-thieno[3,2-b]pyrrole-5-carboxylic acid ethyl ester

5-Chloro-4-methyl-thiophene-2-carbaldehyde was annulated according to Procedure H (aldehyde and azido-acetic acid ethyl ester was added as ethanol solution (1 M of ester) to −20° C. ethoxide solution; allow to warm to 10° C. over 2 h, 10° C. 2 h; reaction poured into cold saturated aqueous NH$_4$Cl; after ether extraction, acrylate organic phase washed with water until aqueous phase was neutral; solution of crude acrylate added to refluxing xylenes over 5 min and then heated at reflux).

CIMS m/e 243.8/245.9 (MH$^+$). $^1$H NMR (CDCl$_3$) δ9.25 (br s, 1H), 7.02 (d, J=1.9 Hz, 1H), 4.36 (q, J=7.1 Hz, 2H), 2.28 (s, 3H), 1.38 (t, J=7.1 Hz, 3H).

Example 46c

2-Chloro-3-methyl-4H-thieno[3,2-b]pyrrole-5-carboxylic acid

2-Chloro-3-methyl-4H-thieno[3,2-b]pyrrole-5-carboxylic acid ethyl ester was hydrolyzed according to Procedure F (50° C. 14 h).

CIMS m/e 213.8/215.8 ((M−H)$^+$). $^1$H NMR (DMSO-d$_6$) δ12.61 (br s, 1H), 12.25 (s, 1H), 6.96 (dd, J=0.5, 2.0 Hz, 1H), 2.23 (s, 1H).

Example 47

2-Chloro-3-methyl-4H-thieno[3,2-b]pyrrole-5-carboxylic acid [(1S)-benzyl-3-((3R,4S)-dihydroxy-pyrrolidin-1-yl)-(2R)-hydroxy-3-oxo-propyl]-amide 2-Chloro-3-methyl-4H-thieno[3,2-b]pyrrole-5-carboxylic acid and (3S)-amino-1-((3R,4S)-dihydroxy-pyrrolidin-1-yl)-(2R)-hydroxy-4-phenyl-butan-1-one were coupled according to Procedure B (4:5 dichloromethane:dimethylformamide; 2 d reaction time; reaction mixture concentrated to remove dichloromethane; partitioned between ethyl acetate and water; organic phase washed with 2 N HCl prior to saturated aqueous NaHCO$_3$).

mp 150–153° C.; CIMS m/e 478.1/480.1 (MH$^+$). $^1$H NMR (DMSO-d$_6$) δ11.91 (s, 0.5H), 11.86 (s, 0.5H), 7.82 (d, J=8.7,1H), 7.22 (m, 4H), 7.11 (m, 1H), 7.01 (m, 1H), 5.07 (d, J=6.8 Hz, 0.5H), 4.95 (m, 1H), 4.90 (d, J=5.0 Hz, 0.5H), 4.82 (d, J=6.8 Hz, 0.5H), 4.77 (d, J=3.7 Hz, 0.5H), 4.44 (m, 1H), 4.21 (m, 1H), 4.08–3.88 (m, 1.5H), 3.56 (m, 1H), 3.40 (m, 0.5H), 3.24 (m, 1.5H), 3.14 (m, 1H), 3.08 (m, 0.5H), 2.95–2.82 (m, 2H).

Example 48

2-Methylsulfanyl-4H-thieno[3,2-b]pyrrole-5-carboxylic acid [(1S)-benzyl-2-((3R,4S)-dihydroxy-pyrrolidin-1-yl)-2-oxo-ethyl]-amide 2-Methylsulfanyl-4H-thieno[3,2-b]pyrrole-5-carboxylic acid and (2S)-amino-1-((3R,4S)-dihydroxy-pyrrolidin-1-yl)-3-phenyl-propan-1-one hydrochloride were coupled according to Procedure B (1:1 dichloromethane:dimethylformamide; reaction mixture concentrated to remove dichloromethane, partitioned between ethyl acetate and water; organic phase washed with 2 N HCl prior to saturated aqueous NaHCO$_3$).

mp 104–110° C.; 444.0 ((M−H)$^+$), 445.9 (MH$^+$). $^1$H NMR (DMSO-d$_6$)) δ11.61 (m, 1H), 8.52 (d, J=8.6 Hz, 1H), 7.28–7.12 (m, 6H), 6.97 (d, J=3.9 Hz, 1H), 4.99 (d, J=5.1 Hz, 0.5H), 4.91 (d, J=5.1 Hz, 0.5H), 4.83 (m, 2H), 4.06–3.94 (m, 1H), 3.80 (m, 2H), 3.43–3.24 (m, 2H), 3.14 (m, 1H), 3.02–2.87 (m, 2H), 2.46 (s, 3H).

Example 48a

2-Methylsulfanyl-4H-thieno[3,2-b]pyrrole-5-carboxylic acid ethyl ester

5-Methylsulfanyl-thiophene-2-carbaldehyde was annulated according to Procedure H (aldehyde and azido-acetic acid ethyl ester added as ethanol solution (1 M of ester) to −20° C. ethoxide solution; allow to warm to 10° C. over 4 h; reaction poured into cold saturated aqueous NH$_4$Cl; after ether extraction, acrylate organic phase washed with water until aqueous phase was neutral; crude acrylate solution heated at reflux for 2 h, allowed to cool to room temperature, stirred overnight).

CIMS m/e 240.0 ((M−H)$^+$), 242.0 (MH$^+$). $^1$H NMR (CDCl$_3$) δ9.05 (br s, 1H), 7.04 (m, 1H), 6.97 (s, 1H), 4.35 (q, J=7.1 Hz, 2H), 2.53 (s, 3H), 1.37 (t, J=7.1 Hz, 3H).

Example 48b

2-Methylsulfanyl-4H-thieno[3,2-b]pyrrole-5-carboxylic acid

2-Methylsulfanyl-4H-thieno[3,2-b]pyrrole-5-carboxylic acid ethyl ester was hydrolyzed according to Procedure F (40° C. overnight).

CIMS m/e 211.9 ((M−H)⁺). $^1$H NMR (DMSO-$d_6$)) δ12.56 (s, 1H), 11.90 (s, 1H), 6.97 (s, 1H), 6.94 (s, 1H), (s, 1H).

The following compounds can also be prepared as set forth above:

2-bromo-4H-thieno[3,2-b]pyrrole-5-carboxylic acid [(1S)-benzyl-2-(3-hydroxy-azetidin-1-yl)-2-oxo-ethyl]-amide;

2-bromo-4H-thieno[3,2-b]pyrrole-5-carboxylic acid [(1S)-benzyl-2-(1,1-dioxo-1-thiazolidin-3-yl)-2-oxo-ethyl]-amide;

2-bromo-4H-thieno[3,2-b]pyrrole-5-carboxylic acid [(1S)-benzyl-2-morpholin-4-yl-2-oxo-ethyl]-amide;

2-bromo-4H-thieno[3,2-b]pyrrole-5-carboxylic acid [(1S)-benzyl-2-((3S,4S)-dihydroxy-pyrrolidin-1-yl)-2-oxo-ethyl]-amide;

2-bromo-4H-thieno[3,2-b]pyrrole-5-carboxylic acid [(1S)-benzyl-2-((3R,4R)-dihydroxy-pyrrolidin-1-yl)-2-oxo-ethyl]-amide; and 2-bromo-4H-thieno[3,2-b]pyrrole-5-carboxylic acid [(1S)-benzyl-2-(4-hydroxy-piperidin-1-yl)-2-oxo-ethyl]-amide.

Biological Protocols

The utility of the compounds of the present invention as medical agents in the treatment or prevention of diseases (such as are detailed herein) in animals, particularly mammals (e.g. humans) is demonstrated by the activity of the compounds of this invention in conventional assays and the in vitro and in vivo assays described below. Such assays also provide a means whereby the activities of the compounds of this invention can be compared with the activities of other known compounds. The results of these comparisons are useful for determining dosage levels in animals, particularly mammals, including humans, for the treatment of such diseases.

Glycogen Phosphorylase Production and Assays

The three different purified glycogen phosphorylase (GP) isoenzymes, wherein glycogen phosphorylase is in the activated "a" state (referred to as glycogen phosphorylase a, or the abbreviation GPa), and referred to here as human liver glycogen phosphorylase a (HLGPa), human muscle glycogen phosphorylase a (HMGPa), and human brain glycogen phosphorylase a (HBGPa), can be obtained by the following procedures.

Expression and Fermentation

The HLGP cDNAs (obtained as described in Newgard et al., Proc. Natl. Acad. Sci., 83: 8132–8136 (1986), and Newgard et al., Proc. Natl. Acad. Sci., 263: 3850–3857 (1988), respectively) and HMGP cDNAs (obtained by screening a Stratagene (Stratagene Cloning Systems, La Jolla, Calif.) human muscle cDNA library with a polymerase chain reaction (PCR)-generated cDNA fragment based on information and methodology reported for isolation of the human skeletal muscle glycogen phosphorylase gene and partial cDNA sequence by Kubisch et al., Center for Molecular Neurobiology, University of Hamburg, Martinistrasse 85, Hamburg, 20246 Germany; Genbank (National Center for Biotechnology Information, National Institutes of Health, USA) Accession Numbers U94774, U94775, U94776 and U94777, submitted Mar. 20, 1997; Burke et al., Proteins, 2:177–187 (1987); and Hwang et al., Eur. J. Biochem., 152: 267–274 (1985)) are expressed from plasmid pKK233–2 (Pharmacia Biotech. Inc., Piscataway, N.J.) in E. coli strain XL-1 Blue (Stratagene Cloning Systems, La Jolla, Calif.). The strain is inoculated into LB medium (consisting of 10 g tryptone, 5 g yeast extract, 5 g NaCl, and 1 ml 1 N NaOH per liter) plus 100 mg/L ampicillin, 100 mg/l pyridoxine and 600 mg/L $MnCl_2$ and grown at 37° C. to a cell density of $OD_{550}$=1.0. At this point, the cells are induced with 1 mM isopropyl-1-thio-β-D-galactoside (IPTG). Three hours after induction the cells are harvested by centrifugation and cell pellets are frozen at −70° C. until needed for purification.

The HBGP cDNA can be expressed by several methodologies, for example, by the method described by Crerar, et al. (J. Biol. Chem. 270:13748–13756 (1995)). The method described by Crerar, et al. (J. Biol. Chem., 270:13748–13756 (1995)) for the expression of HBGP is as follows: the HBGP cDNA can be expressed from plasmid pTACTAC in E. coli strain 25A6. The strain is inoculated into LB medium (consisting of 10 g tryptone, 5 g yeast extract, 5 g NaCl, and 1 ml 1 N NaOH per liter) plus 50 mg/L ampicillin and grown overnight, then resuspended in fresh LB medium plus 50 mg/L ampicillin, and reinoculated into a 40× volume of LB/amp media containing 250 μM isopropyl-1-thio-β-D-galactoside (IPTG), 0.5 mM pyridoxine and 3 mM $MnCl_2$ and grown at 22° C. for 48–50 hours. The cells can then be harvested by centrifugation and cell pellets are frozen at −70° C. until needed for purification.

The HLGP cDNA is expressed from plasmid pBlueBac III (Invitrogen Corp., San Diego, Calif.) which is cotransfected with BaculoGold Linear Viral DNA (Pharmingen, San Diego, Calif.) into Sf9 cells. Recombinant virus is subsequently plaque-purified. For production of protein, Sf9 cells grown in serum-free medium (Sf-900 II serum free medium, Gibco BRL, Life Technologies, Grand Island, N.Y.) are infected at an moi of 0.5 and at a cell density of $2 \times 10^6$ cells/ml. After growth for 72 hours at 27° C., cells are centrifuged, and the cell pellets frozen at −70° C. until needed for purification.

Purification of Glycogen Phosphorylase Expressed in E. coli

The E. coli cells in pellets described above are resuspended in 25 mM β-glycerophosphate (pH 7.0) with 0.2 mM DTT, 1 mM $MgCl_2$, plus the following protease inhibitors:

| | |
|---|---|
| 0.7 μg/ml | Pepstatin A |
| 0.5 μg/ml | Leupeptin |
| 0.2 mM | phenylmethylsulfonyl fluoride (PMSF), and |
| 0.5 mM | EDTA, | lysed by pretreatment with 200 μg/ml lysozyme and 3 μg/ml DNAase followed by sonication in 250 ml batches for 5×1.5 minutes on ice using a Branson Model 450 ultrasonic cell disrupter (Branson Sonic Power Co., Danbury, Conn.). The E. coli cell lysates are then cleared by centrifugation at 35,000×g for one hour followed by filtration through 0.45 micron filters. GP in the soluble fraction of the lysates (estimated to be less than 1% of the total protein) is purified by monitoring the enzyme activity (as described in GPa Activity Assay section, below) from a series of chromatographic steps detailed below.

Immobilized Metal Affinity Chromatography (IMAC)

This step is based on the method of Luong et al (Luong et al. Journal of Chromatography 584: 77–84 (1992)). Five hundred ml of the filtered soluble fraction of cell lysates (prepared from approximately 160–250 g of original cell pellet) are loaded onto a 130 ml column of IMAC Chelating- Sepharose (Pharmacia LKB Biotechnology, Piscataway, N.J.) which has been charged with 50 mM $CuCl_2$ and 25 mM β-glycerophosphate, 250 mM NaCl and 1 mM imidazole at pH 7 (equilibration buffer). The column is washed with equilibration buffer until the $A_{280}$ returns to baseline. The sample is then eluted from the column with the same buffer containing 100 mM imidazole to remove the bound GP and other bound proteins. Fractions containing the GP activity are pooled (approximately 600 ml), and ethylenediaminetetraacetic acid (EDTA), DL-dithiothreitol (DTT), phenylmethylsulfonyl fluoride (PMSF), leupeptin and pepstatin A are added to obtain 0.3 mM, 0.2 mM, 0.2 mM, 0.5 µg/ml and 0.7 µg/ml concentrations respectively. The pooled GP is desalted over a Sephadex G-25 column (Sigma Chemical Co., St. Louis, Mo.) equilibrated with 25 mM Tris-HCl (pH 7.3), 3 mM DTT buffer (Buffer A) to remove imidazole and is stored on ice and subjected to a second chromatographic step (below) if necessary.

5'-AMP-Sepharose Chromatography

The desalted pooled GP sample (approximately 600 mL) is next mixed with 70 ml of 5'-AMP Sepharose (Pharmacia LKB Biotechnology, Piscataway, N.J.) which has been equilibrated with Buffer A (see above). The mixture is gently agitated for one hour at 22° C. then packed into a column and washed with Buffer A until the $A_{280}$ returns to baseline. GP and other proteins are eluted from the column with 25 mM Tris-HCl, 0.2 mM DTT and 10 mM adenosine 5'-monophosphate (AMP) at pH 7.3 (Buffer B). GP-containing fractions are pooled following identification by determining enzyme activity described below and visualizing the Mr approximately 97 kdal GP protein band by sodium dodecyl sulfate polyacrylamide gel electrophoresis (SDS-PAGE) followed by silver staining (2D-silver Stain II "Daiichi Kit", Daiichi Pure Chemicals Co., LTD., Tokyo, Japan) and then pooled. The pooled GP is dialyzed into 25 mM β-glycerophosphate, 0.2 mM DTT, 0.3 mM EDTA, 200 mM NaCl, pH 7.0 buffer (Buffer C) and stored on ice until use.

Prior to use of the GP enzyme, the enzyme is converted from the inactive form as expressed in *E. coli* strain XL-1 Blue (designated GPb) (Stragene Cloning Systems, La Jolla, Calif.), to the active form (designated GPa) by the procedure described in Section (A) Activation of GP below.

Purification of Glycogen Phosphorylase Expressed in Sf9 Cells

The Sf9 cells in pellets described above are resuspended in 25 mM β-glycerophosphate (pH 7.0) with 0.2 mM DTT, 1 mM MgCl2, plus the following protease inhibitors:

| | |
|---|---|
| 0.7 µg/ml | Pepstatin A |
| 0.5 µg/ml | Leupeptin |
| 0.2 mM | phenylmethylsulfonyl fluoride (PMSF), and |
| 0.5 mM | EDTA, | lysed by pretreatment with 3 µg/ml DNAase followed by sonication in batches for 3×1 minutes on ice using a Branson Model 450 ultrasonic cell disrupter (Branson Sonic Power Co., Danbury, Conn.). The Sf9 cell lysates are then cleared by centrifugation at 35,000×g for one hour followed by filtration through 0.45 micron filters. GP in the soluble fraction of the lysates (estimated to be 1.5% of the total protein) is purified by monitoring the enzyme activity (as described in GPa Activity Assay section, below) from a series of chromatographic steps detailed below.

Immobilized Metal Affinity Chromatography (IMAC)

Immobilized Metal Affinity Chromatography is performed as described in the section above. The pooled, desalted GP is then stored on ice until further processed.

Activation of GP

Before further chromatography, the fraction of inactive enzyme as expressed in Sf9 cells (designated GPb) is converted to the active form (designated GPa) by the following procedure described in Section (A) Activation of GP below.

Anion Exchange Chromatography

Following activation of the IMAC purified GPb to GPa by reaction with the immobilized phosphorylase kinase, as described below, the pooled GPa fractions are dialyzed against 25 mM Tris-HCl, pH 7.5, containing 0.5 mM DTT, 0.2 mM EDTA, 1.0 mM phenylmethylsulfonyl fluoride (PMSF), 1.0 µg/ml leupeptin and 1.0 µg/ml pepstatin A. The fraction is then loaded onto a MonoQ Anion Exchange Chromatography column (Pharmacia Biotech. Inc., Piscataway, N.J.). The column is washed with equilibration buffer until the $A_{280}$ returns to baseline. The sample is then eluted from the column with a linear gradient of 0–0.25 M NaCl to remove the bound GP and other bound proteins. GP-containing fractions elute between 0.1–0.2 M NaCl range, as detected by monitoring the eluant for peak protein absorbance at $A_{280}$. The GP protein is then identified by visualizing the $M_r$ approximately 97 kdal GP protein band by sodium dodecyl sulfate polyacrylamide gel electrophoresis (SDS-PAGE) followed by silver staining (2D-silver Stain II "Daiichi Kit", Daiichi Pure Chemicals Co., LTD., Tokyo, Japan) and then pooled. The pooled GP is dialyzed into 25 mM N,N-bis-(2-hydroxyethyl)-2-aminoethanesulfonic acid (BES), 1.0 mM DTT, 0.5 mM EDTA, 5 mM NaCl, pH 6.8 buffer and stored on ice until use.

Determination of GP Enzyme Activity
A) Activation of GP: Conversion of GPb to GPa Prior to the determination of GP enzyme activity, the enzyme is converted from the inactive form as expressed in *E. coli* strain XL-1 Blue (designated GPb) (Stragene Cloning Systems, La Jolla, Calif.), to the active form (designated GPa) by phosphorylation of GP using phosphorylase kinase as follows. The fraction of inactive enzyme as expressed in Sf9 cells (designated GPb) is also converted to the active form (designated GPa) by the follow procedure.

GP Reaction with Immobilized Phosphorylase Kinase

Phosphorylase kinase (Sigma Chemical Company, St. Louis, Mo.) is immobilized on Affi-Gel® 10 (BioRad Corp., Melvile, N.Y.) as per the manufacturer's instructions. In brief, the phosphorylase kinase enzyme (10 mg) is incubated with washed Affi-Gel® beads (1 ml) in 2.5 ml of 100 mM HEPES and 80 mM $CaCl_2$ at pH 7.4 for 4 hours at 4° C. The Affi-Gel® beads are then washed once with the same buffer prior to blocking with 50 mM HEPES and 1 M glycine methyl ester at pH 8.0 for one hour at room temperature. Blocking buffer is removed and replaced with 50 mM HEPES (pH 7.4), 1 mM β-mercaptoethanol and 0.2% $NaN_3$ for storage. Prior to use to convert GPb to GPa, the Affi-Gel® immobilized phosphorylase kinase beads are equilibrated by washing in the buffer used to perform the kinase reaction, consisting of 25 mM β-glycerophosphate, 0.3 mM DTT, and 0.3 mM EDTA at pH 7.8 (kinase assay buffer).

The partially purified, inactive GPb obtained from 5'-AMP-Sepharose chromatography above (from *E. coli*) or the mixture of GPa and GPb obtained from IMAC above (from Sf9 cells) is diluted 1:10 with the kinase assay buffer then mixed with the aforementioned phosphorylase kinase enzyme immobilized on the Affi-Gel® beads. NaATP is added to 5 mM and $MgCl_2$ to 6 mM. The resulting mixture is mixed gently at 25° C. for 30 to 60 minutes. The activated sample is removed from the beads and the percent activation of GPb by conversion to GPa is estimated by determining GP enzyme activity in the presence and absence of 3.3 mM AMP. The percentage of total GP enzyme activity due to GPa enzyme activity (AMP-independent) is then calculated as follows:

$$\% \text{ of total } HLGPa = \frac{HLGP \text{ activity} - AMP}{HLGP \text{ activity} + AMP}$$

Alternately, the conversion of GPb to GPa can be monitored by isoelectric focusing, based on the shift in electrophoretic mobility that is noted following conversion of GPb to GPa. GP samples are analyzed by isoelectric focusing (IEF) utilizing the Pharmacia PfastGel System (Pharmacia Biotech. Inc., Piscataway, N.J.) using precast gels (pI range 4–6.5) and the manufacturer's recommended method. The resolved GPa and GPb bands are then visualized on the gels by silver staining (2D-silver Stain II "Daiichi Kit", Daiichi Pure Chemicals Co., LTD., Tokyo, Japan). Identification of GPa and GPb is made by comparison to *E. coli* derived GPa and GPb standards that are run in parallel on the same gels as the experimental samples.

B) GPa Activity Assay

The disease/condition treating/preventing activities described herein of the compounds of the present invention can be indirectly determined by assessing the effect of the compounds of this invention on the activity of the activated form of glycogen phosphorylase (GPa) by one of two methods; glycogen phosphorylase a activity is measured in the forward direction by monitoring the production of glucose-1-phosphate from glycogen or by following the reverse reaction, measuring glycogen synthesis from glucose-1-phosphate by the release of inorganic phosphate. All reactions are run in triplicate in 96-well microtiter plates and the change in absorbance due to formation of the reaction product is measured at the wavelength specified below in a MCC/340 MKII Elisa Reader (Lab Systems, Finland), connected to a Titertech Microplate Stacker (ICN Biomedical Co, Huntsville, Ala.).

To measure the GPa enzyme activity in the forward direction, the production of glucose-1-phosphate from glycogen is monitored by the multienzyme coupled general method of Pesce et al. [Pesce, M. A., Bodourian, S. H., Harris, R. C. and Nicholson, J. F. *Clinical Chemistry* 23: 1711–1717 (1977)] modified as follows: 1 to 100 μg GPa, 10 units phosphoglucomutase and 15 units glucose-6-phosphate dehydrogenase (Boehringer Mannheim Biochemicals, Indianapolis, Ind.) are diluted to 1 mL in Buffer D (pH 7.2, 50 mM HEPES, 100 mM KCl, 2.5 mM ethyleneglycoltetraacetic acid (EGTA), 2.5 mM $MgCl_2$, 3.5 mM $KH_2PO_4$ and 0.5 mM dithiothreitol). Twenty μl of this stock is added to 80 μl of Buffer D containing 0.47 mg/mL glycogen, 9.4 mM glucose, 0.63 mM of the oxidized form of nicotinamide adenine dinucleotide phosphate (NADP+). The compound to be tested is added as 5 μl of solution in 14% dimethylsulfoxide (DMSO) prior to the addition of the enzymes. The basal rate of GPa enzyme activity in the absence of inhibitors, e.g., a compound of this invention, is determined by adding 5 μl of 14% DMSO and a fully-inhibited rate of GPa enzyme activity is obtained by adding 20 μl of 50 mM of the positive control test substance, caffeine. The reaction is followed at room temperature by measuring the conversion of oxidized NADP+ to reduced NADPH at 340 nm.

To measure the GPa enzyme activity in the reverse direction, the conversion of glucose-1-phosphate into glycogen plus inorganic phosphate is measured by the general method described by Engers et al. [Engers, H. D., Shechosky, S. and Madsen, N. B., *Can. J. Biochem.* 48: 746–754 (1970)] modified as follows: 1 to 100 ug GPa is diluted to 1 ml in Buffer E (pH 7.2, 50 mM HEPES, 100 mM KCl, 2.5 mM EGTA, 2.5 mM $MgCl_2$ and 0.5 mM dithiothreitol). Twenty μl of this stock is added to 80 μl of Buffer E with 1.25 mg/ml glycogen, 9.4 mM glucose, and 0.63 mM glucose-1-phosphate. The compound to be tested is added as 5 μl of solution in 14% DMSO prior to the addition of the enzyme. The basal rate of GPa enzyme activity in the absence of added inhibitors, e.g., a compound of this invention, is determined by adding 5 μl of 14% DMSO and a fully-inhibited rate of GPa enzyme activity is obtained by adding 20 μL of 50 mM caffeine. This mixture is incubated at room temperature for 1 hour and the inorganic phosphate released from the glucose-1-phosphate is measured by the general method of Lanzetta et al. [Lanzetta, P. A., Alvarez, L. J., Reinach, P. S. and Candia, O. A. *Anal. Biochem.* 100: 95–97 (1979)] modified as follows: 150 μl of 10 mg/ml ammonium molybdate, 0.38 mg/ml malachite green in 1 N HCl is added to 100 μl of the enzyme mix. After a 20 minute incubation at room temperature, the absorbance is measured at 620 nm.

The above assays carried out with a range of concentrations of test compound allows the determination of an $IC_{50}$ value (concentration of test compound required for 50% inhibition) for the in vitro inhibition of GPa enzyme activity by that test compound.

The compounds of this invention are readily adapted to clinical use as hypoglycemic agents. The hypoglycemic activity of the compounds of this invention can be determined by the amount of test compound that reduces glucose levels relative to a vehicle without test compound in male ob/ob mice. The test also allows the determination of an approximate minimal effective dose (MED) value for the in vivo reduction of plasma glucose concentration in such mice for such test compounds.

Since the concentration of glucose in blood is closely related to the development of diabetic disorders, the compounds of the present invention, by virtue of their hypoglycemic action, prevent, arrest and/or regress diabetic disorders.

Five to eight week old male C57BL/6J-ob/ob mice (obtained from Jackson Laboratory, Bar Harbor, Me.) are housed five per cage under standard animal care practices. After a one week acclimation period, the animals are weighed and 25 microliters of blood are collected from the retro-orbital sinus prior to any treatment. The blood sample is immediately diluted 1:5 with saline containing 0.025% sodium heparin, and held on ice for metabolite analysis. Animals are assigned to treatment groups so that each group has a similar mean for plasma glucose concentration. After group assignment, animals are dosed orally each day for four days with the vehicle consisting of either: (1) 0.25% w/v methyl cellulose in water without pH adjustment; or (2)

0.1% Pluronic® P105 Block Copolymer Surfactant (BASF Corporation, Parsippany, N.J.) in 0.1% saline without pH adjustment. On day 5, the animals are weighed again and then dosed orally with a test compound or the vehicle alone. All compounds are administered in vehicle consisting of either: (1) 0.25% w/v methyl cellulose in water; or 3) neat PEG 400 without pH adjustment; (2) 10% DMSO/0.1% Pluronic® in 0.1% saline without pH adjustment; or 3) neat PEG 400 without pH adjustment. The animals are then bled from the retro-orbital sinus three hours later for determination of blood metabolite levels. The freshly collected samples are centrifuged for two minutes at 10,000×g at room temperature. The supernatant is analyzed for glucose, for example, by the Abbott VP™ (Abbott Laboratories, Diagnostics Division, Irving, Tex.) and VP Super System® Autoanalyzer (Abbott Laboratories, Irving, Tex.), or by the Abbott Spectrum CCX™ (Abbott Laboratories, Irving, Tex.) using the A-Gen™ Glucose-UV Test reagent system (Abbott Laboratories, Irving, Tex.) (a modification of the method of Richterich and Dauwalder, *Schweizerische Medizinische Wochenschrift*, 101: 860 (1971)) (hexokinase method) using a 100 mg/dl standard. Plasma glucose is then calculated by the equation:

Plasma glucose (mg/dl)=Sample value×8.14 where 8.14 is the dilution factor, adjusted for plasma hematocrit (assuming the hematocrit is 44%).

The animals dosed with vehicle maintain substantially unchanged hyperglycemic glucose levels (e.g., greater than or equal to 250 mg/dl), animals treated with compounds having hypoglycemic activity at suitable doses have significantly depressed glucose levels. Hypoglycemic activity of the test compounds is determined by statistical analysis (unpaired t-test) of the mean plasma glucose concentration between the test compound group and vehicle-treated group on day 5. The above assay carried out with a range of doses of a test compound allows the determination of an approximate minimal effective dose (MED) value for the in vivo reduction of plasma glucose concentration.

The compounds of the present invention are readily adapted to clinical use as hyperinsulinemia reversing agents, triglyceride lowering agents and hypocholesterolemic agents. Such activity can be determined by the amount of test compound that reduces insulin, triglycerides or cholesterol levels relative to a control vehicle without test compound in male ob/ob mice.

Since the concentration of cholesterol in blood is closely related to the development of cardiovascular, cerebral vascular or peripheral vascular disorders, the compounds of this invention, by virtue of their hypocholesterolemic action, prevent, arrest and/or regress atherosclerosis.

Since the concentration of insulin in blood is related to the promotion of vascular cell growth and increased renal sodium retention, (in addition to the other actions, e.g., promotion of glucose utilization) and these functions are known causes of hypertension, the compounds of this invention, by virtue of their hypoinsulinemic action, prevent, arrest and/or regress hypertension.

Since the concentration of triglycerides in blood contributes to the overall levels of blood lipids, the compounds of this invention, by virtue of their triglyceride lowering and/or free fatty acid lowering activity prevent, arrest and/or regress hyperlipidemia.

Free fatty acids contribute to the overall level of blood lipids and independently have been negatively correlated with insulin sensitivity in a variety of physiologic and pathologic states.

Five to eight week old male C57BL/6J-ob/ob mice (obtained from Jackson Laboratory, Bar Harbor, Me.) are housed five per cage under standard animal care practices and fed standard rodent diet ad libitum. After a one week acclimation period, the animals are weighed and 25 microliters of blood are collected from the retro-orbital sinus prior to any treatment. The blood sample is immediately diluted 1:5 with saline containing 0.025% sodium heparin, and held on ice for plasma glucose analysis. Animals are assigned to treatment groups so that each group has a similar mean for plasma glucose concentration. The compound to be tested is administered by oral gavage as an about 0.02% to 2.0% solution (weight/volume (w/v)) in either (1) 10% DMSO/ 0.1% Pluronic® P105 Block Copolymer Surfactant (BASF Corporation, Parsippany, N.J.) in 0.1% saline without pH adjustment or (2) 0.25% w/v methylcellulose in water without pH adjustment. Alternatively, the compound to be tested can be administered by oral gavage dissolved in or in suspension in neat PEG 400. Single daily dosing (s.i.d.) or twice daily dosing (b.i.d.) is maintained for 1 to, for example, 15 days. Control mice receive the 10% DMSO/ 0.1% Pluronic® P105 in 0.1% saline without pH adjustment or the 0.25% w/v methylcellulose in water without pH adjustment, or the neat PEG 400 without pH adjustment.

Three hours after the last dose is administered, the animals are sacrificed by decapitation and trunk blood is collected into 0.5 ml serum separator tubes containing 3.6 mg of a 1:1 weight/weight sodium fluoride: potassium oxalate mixture. The freshly collected samples are centrifuged for two minutes at 10,000×g at room temperature, and the serum supernatant is transferred and diluted 1:1 volume/ volume with a 1 TIU/ml aprotinin solution in 0.1% saline without pH adjustment.

The diluted serum samples are then stored at −80° C. until analysis. The thawed, diluted serum samples are analyzed for insulin, triglycerides, free fatty acids and cholesterol levels. Serum insulin concentration is determined using Equate® RIA INSULIN kits (double antibody method; as specified by the manufacturer) available from Binax, South Portland, Me. The inter assay coefficient of variation is ≦10%. Serum triglycerides are determined using the Abbott VP™ and VP Super System® Autoanalyzer (Abbott Laboratories, Irving, Tex.), or the Abbott Spectrum CCX (Abbott Laboratories, Irving, Tex.) using the A-Gent™ Triglycerides Test reagent system (Abbott Laboratories, Diagnostics Division, Irving, Tex.) (lipase-coupled enzyme method; a modification of the method of Sampson, et al., *Clinical Chemistry* 21: 1983 (1975)). Serum total cholesterol levels are determined using the Abbott VP™ and VP Super System® Autoanalyzer (Abbott Laboratories, Irving, Tex.), and A-Gent™ Cholesterol Test reagent system (cholesterol esterase-coupled enzyme method; a modification of the method of Allain, et al. *Clinical Chemistry* 20: 470 (1974)) using 100 and 300 mg/dl standards. Serum free fatty acid concentration is determined utilizing a kit from Amano International Enzyme Co., Inc., as adapted for use with the Abbott VP™ and VP Super System® Autoanalyzer (Abbott Laboratories, Irving, Tex.), or the Abbott Spectrum CCX™ (Abbott Laboratories, Irving, Tex.). Serum insulin, triglycerides, free fatty acids and total cholesterol levels are then calculated by the equations, Serum insulin ($\mu$U/ml)=Sample value×2

Serum triglycerides (mg/dl)=Sample value×2

Serum total cholesterol (mg/dl)=Sample value×2

Serum free fatty acid ($\mu$Eq/l)=Sample value×2 where 2 is the dilution factor.

The animals dosed with vehicle maintain substantially unchanged, elevated serum insulin (e.g., 275 μU/ml), serum triglycerides (e.g., 235 mg/dl), serum free fatty acid (1500 mEq/ml) and serum total cholesterol (e.g., 190 mg/dl) levels, while animals treated with compounds of the present invention generally display reduced serum insulin, triglycerides, free fatty acid and total cholesterol levels. The serum insulin, triglycerides, free fatty acid and total cholesterol lowering activity of the test compounds are determined by statistical analysis (unpaired t-test) of the mean serum insulin, triglycerides, or total cholesterol concentration between the test compound group and the vehicle-treated control group.

What is claimed is:

1. A compound of Formula I:

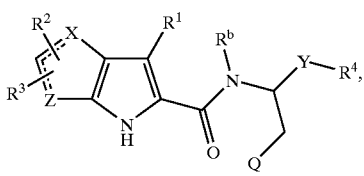

a stereoisomer, Pharmaceutically acceptable salt or prodrug thereof, or a Pharmaceutically acceptable salt of the prodrug,
wherein
Q is aryl, substituted aryl, heteroaryl, or substituted heteroaryl;
Z is C or OH and X is O;
$X^1$ is $NR^a$, —$CH_2$—, O or S;
each ———— is independently a bond or is absent, provided that both ———— are not simultaneously bonds;
$R^1$ is hydrogen, halogen, —$OC_1$-$C_8$alkyl, $SC_1$-$C_8$alkyl, —$C_1$-$C_8$alkyl, —$CF_3$, —$NH_2$, —$NHC_1$-$C_8$alkyl, —$N(C_1$-$C_8$alkyl)$_2$, —$NO_2$, —CN, —$CO_2H$, —$CO_2C_1$-$C_8$alkyl, —$C_2$-$C_8$alkenyl, or —$C_2$-$C_8$alkynyl;
each $R^a$ and $R^b$ is independently hydrogen or —$C_1$-$C_8$alkyl;

Y is ——C(OH)(H)—— or absent;

$R^2$ and $R^3$ are independently hydrogen, halogen, —$C_1$-$C_8$alkyl, —CN, —C≡C—$Si(CH_3)_3$, —$OC_1$-$C_8$alkyl, —$SC_1$-$C_8$alkyl, —$CF_3$, —$NH_2$, —$NHC_1$-$C_8$alkyl, —$N(C_1$-$C_8$alkyl)$_2$, —$NO_2$, —$CO_2H$, —$CO_2C_1$-$C_8$alkyl, —$C_2$-$C_8$alkenyl, or —$C_2$-$C_8$alkynyl;
$R^4$ is —C(=O)—A;
A is —$NR^dR^d$, —$NR^aCH_2CH_2COR^a$,

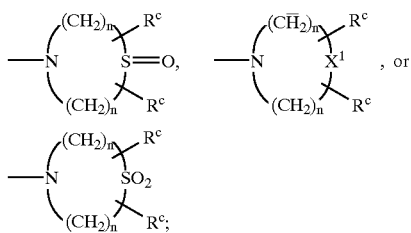

each $R^d$ is independently hydrogen, $C_1$-$C_8$alkyl, $C_1$-$C_8$alkoxy, aryl, substituted aryl, heteroaryl, or substituted heteroaryl;

each $R^c$ is independently hydrogen, —C(=O)$OR^a$, —$OR^a$, —$SR^a$, or —$NR^aR^a$; and
each n is independently 1–3.

2. A compound of claim 1 wherein $R^b$ and $R^1$ are hydrogen.

3. A compound of claim 1 wherein
$R^b$ is hydrogen;
$R^1$ is hydrogen;

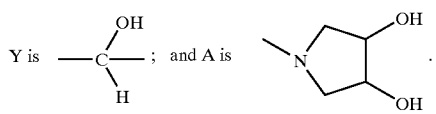

4. A compound of claim 1 wherein
$R^b$ is hydrogen;
$R^1$ is hydrogen;
Y is absent; and
A is

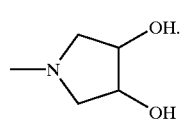

5. A compound of claim 1 wherein
$R^b$ is hydrogen;
$R^1$ is hydrogen;
Z is C;
Y is absent;
A is

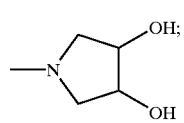

$R^2$ is hydrogen; and
$R^3$ is hydrogen, halogen or methyl.

6. A compound of claim 1 wherein Q is phenyl and A is

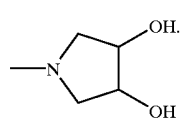

7. A pharmaceutical composition comprising a compound of claim 1, a stereoisomer, pharmaceutically acceptable salt or prodrug thereof, or a pharmaceutically acceptable salt of the prodrug.

8. A method of treating atherosclerosis, diabetes, insulin resistance, diabetic neuropathy, diabetic nephropathy, diabetic retinopathy, cataracts, hypercholesterolemia, hypertriglyceridemia, hyperlipidemia, hyperglycemia, hypertension, tissue ischemia, or myocardial ischemia, the method comprising the step of administering to a patient having or at risk of having atherosclerosis, diabetes, insulin resistance, diabetic neuropathy, diabetic nephropathy, diabetic retinopathy, cataracts, hypercholesterolemia, hypertriglyceridemia, hyperlipidemia, hyperglycemia, hypertension, tissue ischemia, or myocardial ischemia a therapeutically effective amount of a compound of claim 1, a stereoisomer, pharmaceutically acceptable salt or prodrug thereof, or a pharmaceutically acceptable salt of the prodrug.

9. A method of inhibiting glycogen phosphorylase, the method comprising the step of administering to a patient in need of glycogen phosphorylase inhibition, a glycogen phosphorylase inhibiting amount of a compound of claim 1, a stereoisomer, pharmaceutically acceptable salt or prodrug thereof, or a pharmaceutically acceptable salt of the prodrug.

10. A compound selected from the group consisting of:
(±)-2-bromo-4H-furo[3,2-b]pyrrole-5-carboxylic acid [1-benzyl-2-((3R,4S)-dihydroxy-pyrrolidin-1-yl)-2-oxo-ethyl]-amide;
2-bromo-4H-furo[3,2-b]pyrrole-5-carboxylic acid [(1S)-benzyl-3-((3R,4S)-dihydroxy-pyrrolidin-1-yl)-(2R)-hydroxy-3-oxo-propyl]-amide;
2-methyl-4H-furo[3,2-b]pyrrole-5-carboxylic acid [(1S)-benzyl-2-((3R,4S)-dihydroxy-pyrrolidin-1-yl)-2-oxo-ethyl]-amide;
2-cyano-4H-furo[3,2-b]pyrrole-5-carboxylic acid [(1S)-benzyl-2-(3-hydroxy-azetidin-1-yl)-2-oxo-ethyl]-amide;
2-chloro-4H-furo[3,2-b]pyrrole-5-carboxylic acid [(1S)-benzyl-2-((3R,4S)-dihydroxy-pyrrolidin-1-yl)-2-oxo-ethyl]-amide;
2-chloro-4H-furo[3,2-b]pyrrole-5-carboxylic acid [(1S)-benzyl-3-((3R,4S)-dihydroxy-pyrrolidin-1-yl)-(2R)-hydroxy-3-oxo-propyl]-amide;
2-cyano-4H-furo[3,2-b]pyrrole-5-carboxylic acid [(1S)-benzyl-3-((3R,4S)-dihydroxy-pyrrolidin-1-yl)-(2R)-hydroxy-3-oxo-propyl]-amide;
3-bromo-4H-furo[3,2-b]pyrrole-5-carboxylic acid [(1S)-benzyl-2-((3R,4S) -dihydroxy-pyrrolidin-1-yl)-2-oxo-ethyl]-amide;
3-bromo-4H-furo[3,2-b]pyrrole-5-carboxylic acid [(1S)-benzyl-3-((3R,4S)-dihydroxy-pyrrolidin-1-yl)-(2R)-hydroxy-3-oxo-propyl]-amide;
or a stereoisomer, pharmaceutically acceptable salt or prodrug of the compound, or a pharmaceutically acceptable salt of the prodrug.

11. A kit for the treatment of diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, or tissue ischemia in a patient having diabetes, hyperglycemia, hypercholesterolemia, hypertension, hyperinsulinemia, hyperlipidemia, atherosclerosis, or tissue ischemia, the kit comprising:
a) a first pharmaceutical composition comprising a compound in accordance with claim 1, or a stereoisomer, pharmaceutically acceptable salt or prodrug of the compound, or a pharmaceutically acceptable salt of the prodrug;
b) a second pharmaceutical composition comprising a second compound useful for the treatment of diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, or tissue ischemia; and
c) a container for containing the first and second compositions.

12. A method of treating diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, or tissue ischemia, the method comprising the step of administering to a patient having diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, or tissue ischemia, a therapeutically effective amount of a compound of claim 1, a stereoisomer, pharmaceutically acceptable salt or prodrug thereof, or a pharmaceutically acceptable salt of a prodrug in combination with at least one additional compound useful for the treatment of diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, or tissue ischemia.

13. A pharmaceutical composition comprising a compound of claim 1, a stereoisomer, pharmaceutically acceptable salt or prodrug thereof, or a pharmaceutically acceptable salt of the prodrug and at least one additional compound useful to treat diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, or tissue ischemia.

14. The pharmaceutical composition of claim 13 wherein the second compound is useful to treat diabetes and is selected from:
insulin and insulin analogs;
GLP-1 (7–37) (insulinotropin) and GLP-1 (7–36)-NH$_2$;
sulfonylureas and analogs;
biguanides;
α2-antagonists;
imidazolines;
glitazones (thiazolidinediones);
PPAR-gamma agonists fatty acid oxidation inhibitors;
α-glucosidase inhibitors;
β-agonists;
phosphodiesterase inhibitors;
lipid-lowering agents:
antiobesity agents vanadate, vanadium complexes and peroxovanadium complexes;
amylin antagonists;
glucagon antagonists;
gluconeogenesis inhibitors;
somatostatin analogs and antagonists; or
antilipolytic agents.

15. The pharmaceutical composition of claim 13 wherein the second compound is useful to treat diabetes and is selected from:
LysPro insulin, GLP-1 (7-37) (insulinotropin), GLP-1 (7-36) —NH$_2$, chlorpropamide, glibenclamide, tolbutamide, tolazamide, acetohexamide, glypizide, glimepiride, repaglinide, meglitinide;
metformin, phenformin, buformin, midaglizole, isaglidole, deriglidole, idazoxan, efaroxan, fluparoxan, linogliride, ciglitazone, pioglitazone, englitazone, troglitazone, darglitazone, rosiglitazone, clomoxir, etomoxir, acarbose, miglitol, emiglitate, voglibose, MDL-25,637, camiglibose, MDL-73,945, BRL 35135, BRL 37344, Ro 16-8714, ICT D7114, CL 316,243, L-386,398;
benfluorex, fenfluramine, bis(cysteinamide N-octyl) oxovanadium, acipimox, WAG 994, pramlintide acetate, AC2993 or nateglinide.

* * * * *